United States Patent [19]

Itoh et al.

[11] Patent Number: 5,495,024
[45] Date of Patent: Feb. 27, 1996

[54] OPTICALLY ACTIVE AZOLE COMPOUNDS AND THEIR PRODUCTION

[75] Inventors: Katsumi Itoh, Toyono-cho; Kenji Okonogi, Shimamoto-cho; Norikazu Tamura, Kobe, all of Japan

[73] Assignee: Takeda Chemical Industries Ltd., Osaka, Japan

[21] Appl. No.: 302,411

[22] Filed: Sep. 8, 1994

Related U.S. Application Data

[62] Division of Ser. No. 981,850, Nov. 24, 1992, Pat. No. 5,371,100.

[30] Foreign Application Priority Data

| Nov. 25, 1991 | [JP] | Japan | 3-309069 |
| Feb. 5, 1992 | [JP] | Japan | 4-019888 |
| Jun. 5, 1992 | [JP] | Japan | 4-145510 |

[51] Int. Cl.⁶ .................. C07D 249/08; C07D 405/06
[52] U.S. Cl. ............................................. 548/267.8
[58] Field of Search ........................... 548/267.8

[56] References Cited

U.S. PATENT DOCUMENTS

| 4,404,216 | 9/1983 | Richardson . |
| 4,416,682 | 11/1983 | Worthington . |
| 4,554,286 | 11/1985 | Richardson et al. . |
| 4,625,036 | 11/1986 | Boyle . |
| 4,925,863 | 5/1990 | Bayles et al. . |
| 4,957,934 | 9/1990 | Boyle . |
| 4,992,454 | 2/1991 | Richardson . |
| 5,011,850 | 4/1991 | Elbe et al. . |

FOREIGN PATENT DOCUMENTS

| 120276 | 10/1984 | European Pat. Off. . |
| 122693 | 10/1984 | European Pat. Off. . |
| 122056 | 10/1984 | European Pat. Off. . |
| 0131845 | 1/1985 | European Pat. Off. . |
| 174769 | 3/1986 | European Pat. Off. . |
| 0195557 | 9/1986 | European Pat. Off. . |
| 421210 | 4/1991 | European Pat. Off. . |
| 2159148 | 11/1985 | United Kingdom . |

*Primary Examiner*—David B. Springer
*Attorney, Agent, or Firm*—Foley & Lardner

[57] ABSTRACT

An optically active azole compound of the formula (I):

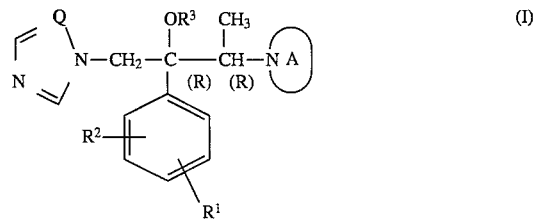

wherein $R^1$ and $R^2$ are independently a hydrogen atom, a halogen atom, a haloalkyl group, a haloalkoxy group or an optionally substituted nitrogen-containing heterocyclic group; $R^3$ is a hydrogen atom or an acyl group; Q is CH or N;

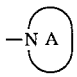

is a nitrogen-containing aromatic five-membered heterocyclic group having at least two adjacent nitrogen atoms as the ring-constituting atoms which may be substituted, or an aromatic condensed heterocyclic group having two or more nitrogen atoms as the ring-constituting atoms which may be substituted; and (R) shows that the carbon atom marked with (R) has R-configuration; provided that either of $R^1$ and $R^2$ is an optionally substituted nitrogen-containing heterocyclic group when

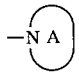

is an 1H-1,2,4-triazol-1-yl group, or a salt thereof, which is useful as an antifungal agent.

4 Claims, No Drawings

OPTICALLY ACTIVE AZOLE COMPOUNDS AND THEIR PRODUCTION

This application is a divisional of Ser. No. 07/981,850 filed Nov. 24, 1992 now U.S. Pat. No. 5,371,100.

BACKGROUND OF THE INVENTION

1. Field of the Invention

The present invention relates to optically active azole compounds useful as antifungal agents, their production and use thereof.

2. Prior Art

Various compounds have been known as antifungal agents. For example, azole derivatives were disclosed as compounds having antifungal activities, e.g., in GB 2,159,148, EPA-19,557 and U.S. Pat. No. 4,957,934. In particular, fluconazole[2-(2,4-difluorophenyl)-1,3-bis(1H-1,2,4-triazo-1 -1-yl)-2-propanol] is known as a typical commercially available product. These compounds are, however, not satisfactory in their therapeutic effects, because they have various problems such as potency of antifungal activities, antifungal spectrum, bioavailability, occurrence of side effects, superinfection and acquisition of drug-resistance.

It would be clear that compounds having higher safety and more potent antifungal activities are desired as therapeutic agents of fungal diseases.

SUMMARY OF THE INVENTION

The present invention is to provide an optically active azole compound represented by the formula (I):

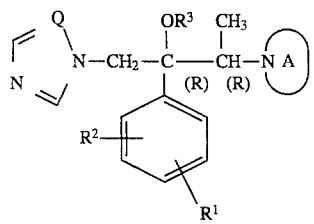

wherein $R^1$ and $R^2$ are each independently a hydrogen atom, a halogen atom, a haloalkyl group, a haloalkoxy group or an optionally substituted nitrogen-containing heterocyclic group; $R^3$ is a hydrogen atom or an acyl group; Q is CH or N;

is a nitrogen-containing aromatic five-membered heterocyclic group having at least two adjacent nitrogen atoms as the ring-constituting atoms which may be substituted, or an aromatic condensed heterocyclic group having two or more nitrogen atoms as the ring-constituting atoms which may be substituted; and (R) shows that the carbon atom marked with (R) has R-configuration; provided that either of $R^1$ and $R^2$ is an optionally substituted nitrogen-containing heterocyclic group when

is an 1H-1,2,4-triazol-1-yl group, or a salt thereof.

The present invention also provides an antifungal composition which comprises an effective amount of an optically active azole compound (I) or its salt and a carrier, excipient or diluent, and further provides a process for preparing an optically active azole compound (I), or its salt.

PREFERRED EMBODIMENTS OF THE INVENTION

In the formula (I), the nitrogen-containing aromatic five-membered heterocyclic group having at least two adjacent nitrogen atoms as the ring-constituting atoms shown by

is suitably an aromatic five-membered heterocyclic group having two to four nitrogen atoms as the ring-constituting atoms where at least two nitrogen atoms are adjacent to each other, such as 1-pyrazolyl, 1H-1,2,4-triazol-1-yl, 4H-1,2,4-triazol-4-yl, 1H-1,2,3-triazol-1-yl, 2H-1,2,3-triazol-2-yl, 1H-tetrazol-1-yl, 2H-tetrazol-2-yl or the like. More suitable examples are the groups where all of two to four nitrogen atoms as the ring-constituting atoms are adjacent to each other, such as 1-pyrazolyl, 1H-1,2,3-triazol-1-yl, 2H-1,2,3-triazol-2-yl, 1H-tetrazol-1-yl, 2H-tetrazol-2-yl or the like. Preferable examples are the groups where all of three or four nitrogen atoms as the ring-constituting atoms are adjacent to each other, such as 1H-1,2,3-triazol-1-yl, 2H-1,2,3-triazol-2-yl, 1H-tetrazol-1-yl or 2H-tetrazol-2-yl, among which 1H-1,2,3-triazol-1-yl and 1H-tetrazol-1-yl are especially preferred.

The aromatic condensed heterocyclic group having two or more nitrogen atoms as the ring-constituting atoms shown by

is preferably a bicyclic or tricyclic aromatic condensed heterocyclic group having two to six nitrogen atoms as the ring-constituting atoms, such as 1H-1-indazolyl, 2H-2-indazolyl, 1H-1-benzotriazolyl, 2H-2-benzotriazolyl, 7H-7-purinyl, 9H-9-purinyl, 9H-9-β-carbolinyl, 2H-2-β-carbolinyl, 3H-3-imidazo[4,5-b]pyridyl, 1H-1-imidazo[4,5-b]pyridyl, 1H-1-pyrazolo[3,4-b]pyrimidinyl, 2H-2-pyrazolo[3,4-b]pyrimidinyl, 1-perimidinyl or the like. More preferable examples are a bicyclic aromatic condensed heterocyclic group having two to four nitrogen atoms as the ring-constituting atoms, such as 7H-7-purinyl, 9H-9-purinyl, 3H-3-imidazo[4,5-b]pyridyl, 1H-1-imidazo[4,5-b]pyridyl or the like.

The groups shown by

in the compound of the formula (I) may be substituted. Examples of such substituents are an optionally halogenated lower alkyl group, an optionally halogenated, haloalkylated or haloalkoxylated aryl group, an optionally halogenated, haloalkylated or haloalkoxylated arylalkenyl group, a halogen, an optionally esterified or amidated carboxyl group, a formyl group, a lower alkoxy group, an azolyl group, an azolyl lower alkyl group, a hydroxy lower alkyl group and the like.

The lower alkyl group in the optionally halogenated lower alkyl group, the azolyl lower alkyl group and the hydroxy lower alkyl group is preferably a straight or branched-chain $C_{1-6}$ (especially $C_{1-4}$) alkyl group, such as methyl, ethyl, propyl, isopropyl, butyl, isobutyl, sec-butyl, tert-butyl, pentyl, isopentyl, neopentyl, tert-pentyl, hexyl, isohexyl or the like.

The aryl group in the optionally halogenated, haloalkylated or haloalkoxylated aryl group is exemplified by a $C_{6-14}$ aryl group such as phenyl, naphthyl, anthryl or phenanthryl, of which phenyl is especially preferred.

The arylalkenyl group in the optionally halogenated, haloalkylated or haloalkoxylated arylalkenyl group is exemplified by a $C_{8-12}$ arylalkenyl group such as styryl, phenylpropenyl or naphthylvinyl, of which styryl is especially preferred.

The halogen in the optionally halogenated lower alkyl group, the optionally halogenated aryl group and the halogen as the substituent on the group shown by

on the haloalkyl group or on the haloalkoxy group are preferably fluorine, chlorine, bromine or iodine, of which fluorine and chlorine are especially preferred.

The haloalkyl group in the optionally haloalkylated aryl group and the optionally haloalkylated arylalkenyl group is preferably a halogenated lower alkyl group as defined above. The preferable examples include trifluoromethyl, difluoromethyl, trichloromethyl, 2,2,2-trifluoroethyl, 2,2,2-trichloroethyl, 2,2,3,3-tetrafluoropropyl, 4,4,5,5-tetrafluoropentyl, 6,6,6-trifluorohexyl or the like. Trifluoromethyl and difluoromethyl are preferred.

The haloalkoxy group in the optionally haloalkoxylated aryl group and the optionally haloalkoxylated arylalkenyl group is preferably a halogenated lower alkoxy group (a lower alkoxy group is as defined below). The preferable examples include trifluoromethoxy, difluoromethoxy, trichloromethoxy, 2,2,2-trifluoroethoxy, 2,2,2-trichloroethoxy, 2,2,3,3-tetrafluoropropoxy, 4,4,5,5-tetrafluoropentyloxy, 6,6,6-trifluorohexyloxy and the like. Trifluoromethoxy, difluoromethoxy and 2,2,2-trifluoroethoxy and 2,2,3,3-tetrafluoropropoxy are preferred.

The optionally esterified or amidated carboxyl group is exemplified by carboxyl group, $C_{1-4}$ lower alkyloxycarbonyl group (e.g., methoxycarbonyl, ethoxycarbonyl, propoxycarbonyl or butoxycarbonyl), carbamoyl group and $C_{1-6}$ lower alkyl aminocarbonyl group (e.g., methylaminocarbonyl, dimethylaminocarbonyl, butylaminocarbonyl or dipropylaminocarbonyl), of which carboxyl, methoxycarbonyl, ethoxycarbonyl and carbamoyl are preferred.

The lower alkoxy group is preferably a straight or branched-chain $C_{1-6}$ (preferably $C_{1-3}$) alkoxy group such as methoxy, ethoxy, propoxy, isopropoxy, butoxy, isobutoxy pentyloxy or the like.

The azolyl group and that in the azolyl lower alkyl groups are preferably 1-imidazolyl or the nitrogen-containing aromatic heterocyclic group exemplified by

more preferably 1-imidazolyl or 1H-1,2,4-triazol-1-yl.

The halogen and that in the haloalkyl or haloalkoxy group with respect to $R^1$ or $R^2$ are exemplified by fluorine, chlorine, bromine or iodine, of which fluorine and chlorine are preferred and fluorine is more preferred.

The alkyl group in the haloalkyl group is suitably a straight or branched-chain $C_{1-6}$ alkyl group such as methyl, ethyl, propyl, isopropyl, butyl, isobutyl, sec-butyl, tert-butyl, pentyl, isopentyl, neo-pentyl, tert-pentyl, hexyl or isohexyl. More suitable examples are straight or branched-chain $C_{1-4}$ alkyl groups such as methyl, ethyl, propyl, isopropyl, butyl, isobutyl, sec-butyl or tert-butyl. Preferable examples are straight or branched-chain $C_{1-3}$ alkyl groups such as methyl, ethyl, propyl or isopropyl.

The haloalkyl group preferably has one to eight halogens, more preferably one to three halogens.

Preferable examples of the haloalkyl groups are trifluoromethyl, difluoromethyl, trichloromethyl, 2,2,2-trifluoroethyl, 2,2,2-trichloroethyl, 2,2,3,3-tetrafluoropropyl, 4,4,5,5-tetrafluoropentyl, 6,6,6-trifluorohexyl and the like. More preferable ones are trifluoromethyl, difluoromethyl, trichloromethyl, 2,2,2-trifluoroethyl, 2,2,2-trichloroethyl and 2,2,3,3-tetrafluoropropyl. Most preferable ones are trifluoromethyl and difluoromethyl.

The alkoxy group in the haloalkoxy group is suitably a straight or branched-chain $C_{1-6}$ alkoxy group such as methoxy, ethoxy, propoxy, isopropoxy, butoxy, isobutoxy, sec-butoxy, tert-butoxy, pentyloxy, isopentyloxy, neopentyloxy or hexyloxy. More suitable examples are straight or branched-chain $C_{1-4}$ alkoxy groups such as methoxy, ethoxy, propoxy, isopropoxy, butoxy, isobutoxy, sec-butoxy and tert-butoxy. Preferable examples are straight or branched-chain $C_{1-3}$ alkoxy groups such as methoxy, ethoxy, propoxy and isopropoxy.

The haloalkoxy group preferably has one to eight halogens, more preferably one to three halogens.

Preferable examples of the haloalkoxy groups are trifluoromethoxy, difluoromethoxy, trichloromethoxy, 2,2,2-trifluoroethoxy, 2,2,2-trichloroethoxy, 2,2,3,3-tetrafluoropropoxy, 4,4,5,5-tetrafluoropentyloxy, 6,6,6-trifluorohexyloxy and the like. More preferable ones are trifluoromethoxy, difluoromethoxy, trichloromethoxy, 2,2,2-trifluoroethoxy, 2,2,2-trichloroethoxy and 2,2,3,3-tetrafluoropropoxy. Most preferable ones are trifluoromethoxy and difluoromethoxy.

The nitrogen-containing heterocyclic group in the optionally substituted nitrogen-containing heterocyclic group shown by $R^1$ or $R^2$ is suitably a 5- or 6-membered heterocyclic group having one to four nitrogen atoms or an azetidinyl group, which may form a condensed ring together with an aromatic or non-aromatic 5- or 6-membered carbon ring (e.g., benzene, cyclohexane, cyclohexene, cyclopentane and cyclopentene). Examples of such heterocyclic groups are 1-benzimidazolyl, 1-indolinyl, 1H-indazol-1-yl, 3-azabicyclo[3.3.0]octo-1,4-dien-3-yl, 3-azabicyclo[4.3.0]nona-1, 4-dien-3-yl, 1-imidazolyl, 1-pyrrolyl, 1-pyrazolyl, 1H-1,2, 4-triazol-1-yl, 4H-1,2,4-triazol-4-yl, 2H-1,2,3-triazol-2-yl, 1H-1,2,3-triazol-1-yl, 1H-tetrazol-1-yl, 2H-tetrazol-2-yl and the like.

Preferable examples are 5- or 6-membered heterocyclic groups having one to four nitrogen atoms, which may form a condensed ring together with an aromatic or non-aromatic 6-membered carbon ring (e.g., benzene, cyclohexane, cyclohexene), specifically such as 1-benzimidazolyl, 1-indolyl, 1H-indazol-1-yl, 3-azabicyclo[4.3.0]nona-1,4-diene-3-yl, 1-imidazolyl, 1-pyrrolyl, 1-pyrazolyl, 1H-1,2,4-triazol-1-yl, 4H-1,2,4-triazol-4-yl, 1H-1,2,3-triazol-1-yl, 2H-1,2,3-triazol-2-yl, 1H-tetrazol-1-yl, 2H-tetrazol-2-yl and the like.

Most preferable examples are aromatic 5- or 6-membered heterocyclic groups having one to three nitrogen atoms, which may form a condensed ring together with a benzene ring, specifically such as 1-benzimidazolyl, 1-indolyl, 1H-indazol-1-yl, 1-imidazolyl, 1-pyrrolyl, 1-pyrazolyl, 1H-1,2,4-triazol-1-yl, 4H-1,2,4-triazol-4-yl, 1H-1,2,3-triazol-1-yl, 2H-1,2,3-triazol-2-yl, 1H-tetrazol-1-yl, 2H-tetrazol-2-yl and the like.

The substituent in the optionally substituted nitrogen-containing heterocyclic group shown by $R^1$ or $R^2$ is preferably an optionally halogenated lower alkyl group, an aryl group, a halogen and the like.

The lower alkyl group in the optionally halogenated lower alkyl group is preferably a straight or branched-chain $C_{1-6}$ (more preferably $C_{1-4}$) alkyl group, specifically such as methyl, ethyl, propyl, isopropyl, butyl, isobutyl, sec-butyl, tert-butyl, pentyl, isopentyl, neopentyl, tert-pentyl, hexyl, isohexyl and the like.

The halogen as the substituent on the nitrogen-containing heterocyclic group and that in the optionally halogenated lower alkyl group is preferably fluorine, chlorine, bromine or the like.

The halogenated lower alkyl group is preferably a lower alkyl group substituted with one to three halogens such as trifluoromethyl, difluoromethyl, 2,2,2-trifluoroethyl, trichloromethyl, bromomethyl or the like, more preferably a lower alkyl group substituted with one to three fluorine atoms such as trifluoromethyl, difluoromethyl, 2,2,2-trifluoroethyl or the like.

The aryl groups are preferably a $C_{6-14}$ aryl group such as phenyl, naphthyl, anthryl, phenanthryl or the like, more preferably a $C_{6-10}$ aryl group such as phenyl or naphthyl.

The substituent on the above-mentioned nitrogen-containing heterocyclic group is preferably a $C_{1-6}$ lower alkyl group.

The number of substituents in the nitrogen-containing heterocyclic group is one to four, preferably one to three.

Each of $R^1$ and $R^2$ is preferably a hydrogen atom, a halogen atom, a haloalkyl group or a haloalkoxy group. In particular, it is preferred that any one of $R^1$ and $R^2$ is a halogen atom and the other is a hydrogen atom or a halogen atom. The halogen atom is fluorine, chlorine, bromine or iodine, preferably fluorine or chlorine, more preferably fluorine. The halogen atom is preferably bonded at 2- and/or 4-position(s).

The acyl group shown by $R^3$ is an acyl group derived from an organic carboxylic acid, for example, an alkanoyl group, preferably a $C_{1-7}$ alkanoyl group (e.g., formyl, acetyl, propionyl, butyryl, isobutyryl, valeryl, isovaleryl, hexanoyl and heptanoyl), more preferably a $C_{1-3}$ alkanoyl group; an arylcarbonyl group, preferably a $C_{7-15}$ arylcarbonyl group (e.g., benzoyl and naphtoyl), more preferably a $C_{7-11}$ arylcarbonyl group; an alkoxycarbonyl group, preferably a $C_{2-7}$ alkoxycarbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl), more preferably a $C_{2-4}$ alkoxycarbonyl group; an aryloxycarbonyl, preferably a $C_{7-15}$ aryloxycarbonyl group (e.g., phenoxycarbonyl and naphtyloxycarbonyl), more preferably a $C_{7-11}$ aryloxycarbonyl group; an aralkylcarbonyl group, preferably a $C_{8-20}$ aralkylcarbonyl group (e.g., benzylcarbonyl, phenethylcarbonyl, phenylpropylcarbonyl and naphthylcarbonyl), more preferably a $C_{8-14}$ aralkylcarbonyl group. All these groups may be substituted with one to three appropriate substituents. Examples of such substituents include the lower alkyl group, the aryl group and the halogen atom in the above-mentioned nitrogen-containing heterocyclic group.

Preferred acyl groups are those which are hydrolyzable in vivo. Examples of such acyl groups are formyl, acetyl, benzoyl, benzylcarbonyl and the like.

The group shown by the formula:

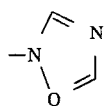

wherein the symbol is defined as above, is specifically exemplified by 1-imidazolyl and 1H-1,2,4-triazol-1-yl, the latter of which is preferable.

The present invention further provides a compound shown by the formula (I'):

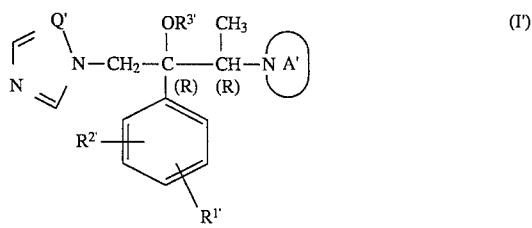

wherein $R^{1'}$ and $R^{2'}$ are a fluorine atom or an optionally substituted nitrogen-containing heterocyclic group, $R^{3'}$ is a hydrogen atom or an acyl group, $Q'$ is CH or N,

is an aromatic five-membered heterocyclic group having at least two adjacent nitrogen atoms as the ring-constituting atoms, and (R) shows that a carbon atom marked with (R) has R-configuration; provided that at least one of $R^{1'}$ and $R^{2'}$ is an optionally substituted nitrogen-containing heterocyclic ring when

is 1H-1,2,4-triazol-1-yl group, or a salt thereof.

The optionally substituted nitrogen-containing heterocyclic group shown by $R^{1'}$ and $R^{2'}$ has the same meaning as the above-mentioned corresponding group of $R^1$ and $R^2$. The acyl group shown by $R^{3'}$ has the same meaning as the above-mentioned corresponding group of $R^3$. The aromatic five-membered heterocyclic group having at least two adjacent nitrogen atoms as the ring-constituting atoms with respect to

has the same meaning as the above-mentioned corresponding group of

The above aromatic five-memebered heterocyclic group may possess the same substituent(s) as mentioned in the corresponding group of

The compound of the formula (I) or its salt is prepared according to the following by methods.

The compound of the formula (I) where $R^3$ is a hydrogen atom, or its salt can be prepared by reacting a compound of the formula (II):

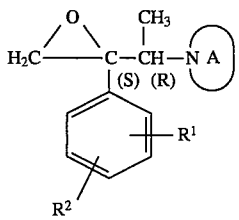

(II)

where (S) shows that the carbon atom marked with (S) has S-configuration, and the other symbols are defined as above, or its salt with a compound of the formula (III):

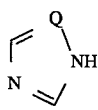

(III)

where the symbol is defined as above, or its salt.

The reaction can usually be conducted in a solvent which does not impede the reaction. Examples of the solvents are water, ketones (e.g., acetone), sulfoxides (e.g., dimethylsulfoxide), ethers (e.g., diethyl ether, tetrahydrofuran and dioxane), nitriles (e.g., acetonitrile), hydrocarbons (e.g., benzene, toluene, hexane and xylene), halogenated hydrocarbons (e.g., dichloromethane, chloroform and 1,2-dichloroethane), esters (e.g., ethyl acetate), amides (e.g., dimethylformamide, acetamide and dimethylacetamide), and ureylenes (e.g., 1,3-dimethyl-2-imidazolidinone).

These solvents can be used either alone or in two or more combination in an appropriate ratio.

The reaction is preferably performed in the presence of a base such as an alkali metal hydroxide (e.g., sodium hydroxide or potassium hydroxide), alkali metal hydride (e.g., sodium hydride or potassium hydride), alkali metal carbonate (e.g., lithium carbonate, sodium hydrogencarbonate, cesium carbonate, potassium carbonate or sodium carbonate), organic acid salt (e.g., sodium acetate), alkali metal alcoholate (e.g., sodium methylate or potassium tert-butylate), tetrabutyl ammonium fluoride, bis(tri-n-butyltin)oxide and the like.

The desired compound can also be obtained by using a metal salt (e.g., sodium or potassium salt) of the compound (III) instead of the compound (III) itself and conducting the reaction in the above-mentioned solvent.

The amount of the base to be used is about 0.001 to 100 equivalents, preferably about 0.01 to 50 equivalents, to the compound (II).

The amount of the compound (III) or its salt is generally about 1 to 100 equivalents, preferably about 1 to 50 equivalents, to the compound (II) or its salt.

The reaction temperature is not particularly limited but ranges usually from about 0° C. to about 150° C., preferably from about 10° C. to about 120° C.

The reaction time is about several minutes to several ten hours, for example, 5 minutes to 50 hours.

A compound of the formula (I) where $R^3$ is a hydrogen atom, or its salt can also be prepared by reacting a compound of the formula (IV):

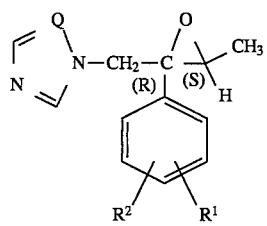

(IV)

where the symbols have the same meanings as above, or its salt with a compound of the formula (V):

(V)

where the symbol has the same meaning as above, or its salt.

The reaction can usually be conducted in a solvent which does not impede the reaction. Examples of such solvents are water, ketones (e.g., acetone), sulfoxides (e.g., dimethylsulfoxide), ethers (e.g., tetrahydrofuran, dioxane or diethylether), nitriles (e.g., acetonitrile), hydrocarbons (e.g., benzene, toluene, hexane or xylene), halogenated hydrocarbons (e.g., dichloromethane, chloroform or 1,2-dichloroethane), esters (e.g., ethyl acetate), amides (e.g., acetamide, dimethylformamide or dimethylacetamide), ureylenes (e.g., 1,3-dimethyl-2-imidazolidinone) and the like.

These solvents can be used either alone or in two or more combination in an appropriate ratio.

The reaction is preferably performed in the presence of a base such as an alkali metal hydroxide (e.g., sodium hydroxide or potassium hydroxide), alkali metal hydride (e.g., sodium hydride or potassium hydride), alkali metal carbonate (e.g., lithium carbonate, sodium hydrogencarbonate, cesium carbonate, potassium carbonate or sodium carbonate), organic salt (e.g., sodium acetate), alkali metal alcoholate (e.g., sodium methylate or potassium tert-butylate), tetrabutylammonium fluoride or bis(tri-n-butyltin)oxide.

The amount of the base to be used is usually about 0.001 to 100 equivalents, preferably about 0.01 to 50 equivalents, to the compound (IV).

The amount of the compound (V) or its salt is about 1 to 100 equivalents, preferably about 1 to 50 equivalents, to the compound (IV) or its salt.

The reaction temperature is not particularly limited but ranges usually from about 0° C. to about 150° C., preferably from about 10° C. to about 120° C.

The reaction time is about several minutes to several hundred hours, preferably, for example, 5 minutes to 50 hours.

The compound of the formula (I) where at least one of $R^1$ and $R^2$ is an optionally substituted aromatic heterocyclic group which bonds to the phenyl group by means of a nitrogen atom, or its salt can be prepared by reacting a compound of the formula (VI):

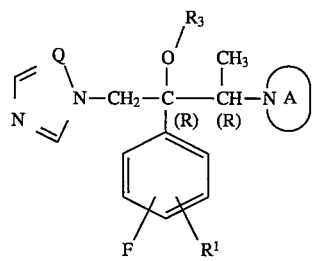

(VI)

where the symbols have the same meanings as defined above, or its salt, with a compound of by the formula (VII):

(VII)

where —NB is an optionally substituted nitrogen-containing heterocyclic group, or its salt.

An optionally substituted nitrogen-containing heterocyclic group is as defined in $R^1$ and $R^2$.

The reaction can usually be conducted in a solvent which does not impede the reaction. Examples of such solvents are ketones (e.g., acetone), sulfoxides (e.g., dimethylsulfoxide), ethers (e.g., dioxane, tetrahydrofuran or diethylether), nitriles (e.g., acetonitrile), hydrocarbons (e.g., benzene, toluene, hexane or xylene), halogenated hydrocarbons (e.g., dichloromethane, chloroform or 1,2-dichloroethane), esters (e.g., ethyl acetate), amides (e.g., acetamide, dimethylformamide or dimethylacetamide), and ureylenes (e.g., 1,3-dimethyl-2-imidazolidinone).

These solvents can be used either alone or in two or more combination in an appropriate ratio.

The reaction is effectively conducted in the presence of a base such as an alkali metal hydride (e.g., sodium hydride or potassium hydride), alkali metal carbonate (e.g., lithium carbonate, sodium hydrogencarbonate, cesium carbonate, potassium carbonate or sodium carbonate), organic acid salt (e.g., sodium acetate) or alkali metal alcoholate (e.g., sodium methylate or potassium tert-butylate).

The amount of the base to be used is usually about 0.1 to 10 equivalents, preferably about 1 to 5 equivalents, to the compound (VI).

The amount of the compound (VII) or its salt to be used is about 1 to 100 equivalents, preferably about 1 to 50 equivalents, to the compound (VI) or its salt.

The reaction temperature is not particularly limited but ranges usually from about 0° C. to about 200° C., preferably from about 10° C. to about 150° C.

The reaction time is about several minutes to several ten hours, preferably, for example, 5 minutes to 50 hours.

The compound of the formula (I) where $R^3$ is an acyl group, or its salt can be prepared by reacting a compound of the formula (I) where $R^3$ is a hydrogen atom, i.e., a compound of the formula (VIII):

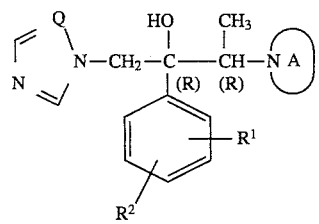
(VIII)

where the symbols have the same meanings as defined above, or its salt, with a compound shown by the formula (IX):

$$R^3—W \qquad (IX)$$

where $R^3$ is defined as above, and W is a halogen (e.g., chlorine or bromine), or $OR^4$ [where $R^4$ is an acyl group, preferably an alkanoyl group such as acetyl or propionyl], or its salt.

The reaction can usually be conducted, using no solvent or a solvent which does not impede the reaction. Examples of such solvents are ketones (e.g., acetone), sulfoxides (e.g., dimethylsulfoxide), ethers (e.g., dioxane, tetrahydrofuran or diethylether), nitriles (e.g., acetonitrile), hydrocarbons (e.g., benzene, toluene, hexane or xylene), halogenated hydrocarbons (e.g., dichloromethane, chloroform or 1,2-dichloroethane), esters (e.g., ethyl acetate), amides (e.g., acetamide, dimethylformamide or dimethylacetamide), and ureylenes (e.g., 1,3-dimethyl-2-imidazolidinone) and the like.

These solvents can be used either alone or in two or more combination in an appropriate ratio.

The reaction is preferably performed in the presence of a base such as a tertiary amine (e.g., an aliphatic tertiary amine such as triethylamine, or an aromatic tertiary amine such as pyridine or 4-dimethylaminopyridine or α-, β- or γ-picoline).

The amount of the base to be used is usually about 0.001 to 100 equivalents, preferably about 0.01 to 5 equivalents, to the compound (VIII).

The amount of the compound (IX) or its salt to be used is about 1 to 100 equivalents, preferably about 1 to 50 equivalents, to the compound (VIII) or its salt.

The reaction temperature is not particularly limited but ranges usually from about −20° C. to about 200° C., preferably from about −10° C. to about 150° C.

The reaction time is about several minutes to several ten hours, preferably, for example, 5 minutes to 50 hours.

The compound of the formula (I) or its salt can be prepared by subjecting a compound of the formula (X):

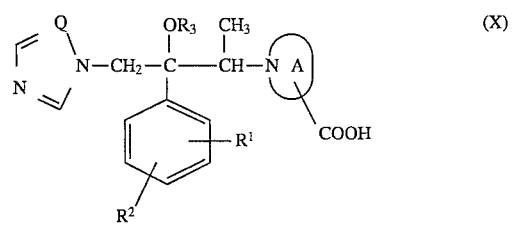
(X)

where the symbols have the same meanings as above, or its salt to decarboxylation.

The reaction can usually be conducted, using no solvent or a solvent which does non impede the reaction. Examples of such solvents are water, ketones (e.g., acetone), sulfoxides (e.g., dimethylsulfoxide), ethers (e.g., dioxane), nitriles (e.g., acetonitrile), hydrocarbons (e.g., toluene, xylene or mesitylene), halogenated hydrocarbons (e.g., tetrachloroethane), amides (e.g., dimethylacetamide), ureylenes (e.g., 1,3-dimethyl-2-imidazolidinone) and the like.

The reaction temperature is not particularly limited but ranges usually from about 80° C. to about 300° C., preferably from about 100° C. to about 250° C.

The reaction time is about several minutes to several ten hours, preferably, for example, 5 minutes to 50 hours.

The compound of the formula (I), where

is an optionally substituted 1H-1,2,3-triazol-1-yl group, or its salt can be prepared by reacting a compound of the formula (XI):

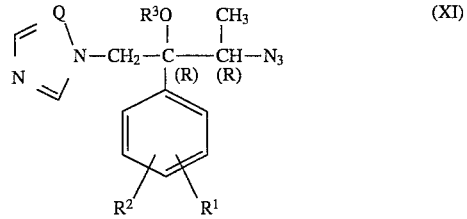
(XI)

where the symbols have the same meanings as defined above, or its salt, with a compound shown by the formula (XII):

 (XII)

where $R^5$ is a hydrogen atom or a substituent which

may have, or its salt.

The reaction can usually be conducted, using no solvent or a solvent which does not impede the reaction. Examples of such solvents are ketones (e.g., acetone), sulfoxides (e.g., dimethylsulfoxide), ethers (e.g., dioxane or tetrahydrofuran), hydrocarbons (e.g., benzene, toluene, xylene or mesitylene), esters (e.g., ethyl acetate), amides (e.g., acetamide, dimethylformamide or dimethylacetamide), ureylenes (e.g., 1,3-dimethyl-2-imidazolidinone) and the like.

These solvents can be used either alone or in two or more combination in an appropriate ratio.

The amount of the compound (XII) to be used is about 1 to 100 equivalents, preferably about 1 to 50 equivalents, to the compound (XI) or its salt.

The reaction temperature is not particularly limited but it ranges usually from about 20° C. to about 200° C., preferably from about 80° C. to about 150° C.

The reaction time is about 1 hour to several ten hours, preferably, for example, 1 hour to 50 hours.

The compound of the formula (I), where

is 1H-1,2,3-triazol-1-yl group which is substituted with an optionally halogenated, haloalkylated or haloalkoxylated arylalkenyl group, or its salt can be prepared by reacting compound of the formula (XIII):

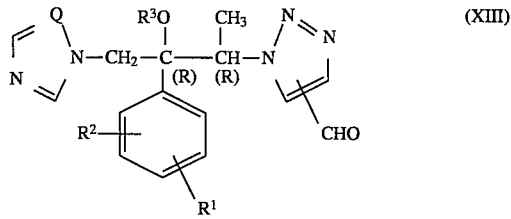 (XIII)

where the symbols have the same meanings as defined above, or its salt, with a compound shown by the formula (XIV):

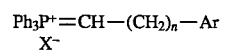 (XIV)

where n is an integer of 0 to 2, Ar is an optionally halogenated, haloalkylated or haloalkoxylated aryl group as defined above, Ph is a phenyl group and X is a halogen (e.g., chlorine, bromine or iodine) in the presence of a base.

The reaction can usually be conducted in a solvent which does not impede the reaction. Examples of such solvents are sulfoxides (e.g., dimethylsulfoxide), ethers (e.g., dioxane or tetrahydrofuran), hydrocarbons (e.g., benzene or toluene) and the like.

These solvents can be used either alone or in two or more combination in an appropriate ratio.

Examples of the bases to be used are alkali metal hydrides (e.g., sodium hydride or potassium hydride), alkali metal alcoholates (e.g., potassium tert-butylate), alkyl metals (e.g., buryl lithium), alkyl metal amides (e.g., lithium diisopropylamide) and the like.

The amount of the base to be used is usually about 0.5 to 10 equivalents, preferably about 1 to 2 equivalents, to the compound (XIV).

The amount of the compound (XIV) or its salt to be used is about 1 to 10 equivalents, preferably about 1 to 2 equivalents, to the compound (XIII) or its salt.

The reaction temperature is not particularly limited but ranges usually from about −78° C. to about 100° C., preferably from about −78° C. to about 40° C.

The reaction time is about several minutes to several ten hours, preferably, for example, 15 minutes to 1 hour.

The compound of formula (I) can also be used in the form of a salt, preferably a physiologically acceptable salt. Examples of the salts include inorganic acid salts such as hydrochloride, hydrobromide, sulfate, nitrate or phosphate; organic acid salts such as acetate, tartarate, citrate, fumarate, maleate, toluenesulfonate or methanesulfonate.

The salts of the compounds (II) to (XIII) are the same as those of the compound (I).

The resultant compound (I) or its salt can be isolated and purified from the reaction mixture by a conventional isolation and purification procedure such as extraction, concentration, neutralization, filtration, crystallization, recrystallization, column chromatography and thin-layer chromatography.

The salt of the compound (I) can be prepared by reacting the compound (I) in a suitable solvent with the aforementioned inorganic acid or organic acid according to per se known procedures.

The compound of the formula (II) as an intermediate product in the present invention, or its salt can be prepared with the method shown by the following reaction scheme.

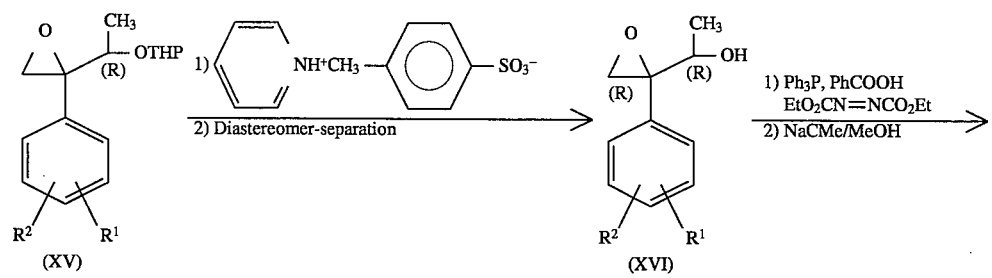

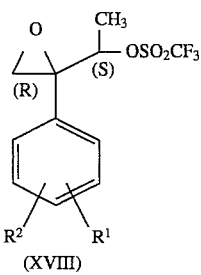
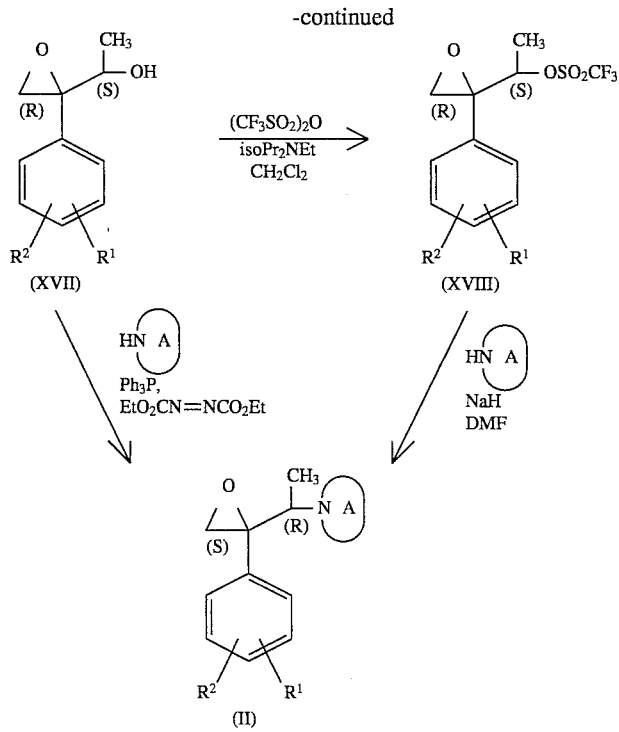

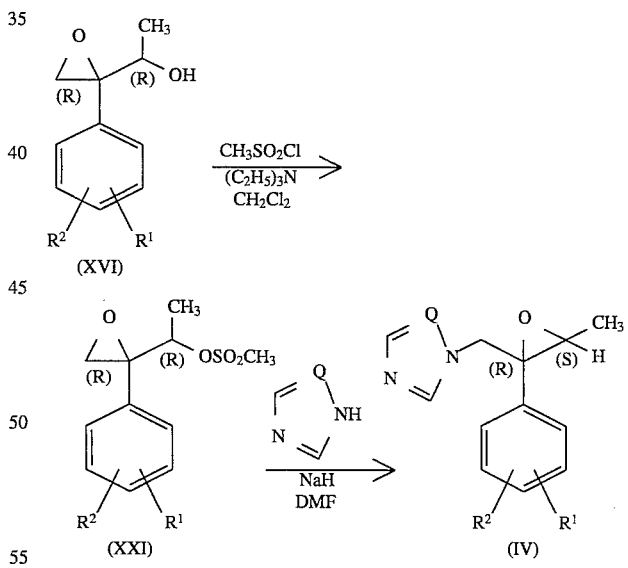

where THP is tetrahydropyranyl group, Me is methyl group, Et is ethyl group, Pr is propyl group, Ph is phenyl group, and $R^1$, $R^2$,

(R) and (S) are defined as above.

The starting compound (XV) in the above reaction can be prepared by the method disclosed in EP 421 210 A2, or it similar method as shown by the following reaction scheme.

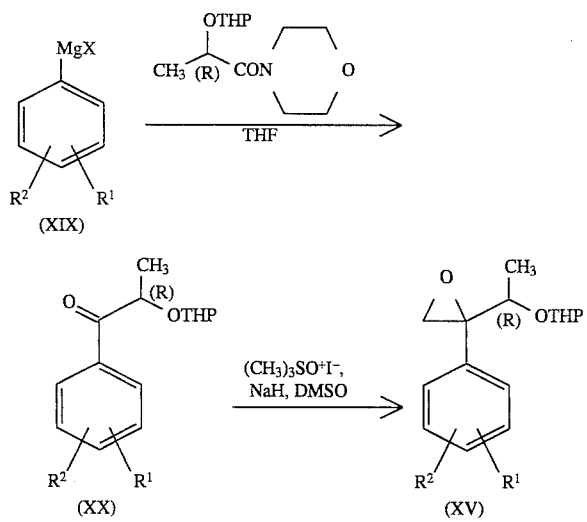

where X is a halogen (e.g., bromine or iodine), the other symbols have the same meanings as defined above.

The compound of the formula (IV) as an intermediate in the present invention, or its salt can be prepared with the method shown by the following reaction scheme.

where the symbols have the same meanings as defined above.

The compound of the formula (XVI) as an intermediate in the above reaction scheme, or its salt can easily be prepared with the method shown by the following reaction scheme.

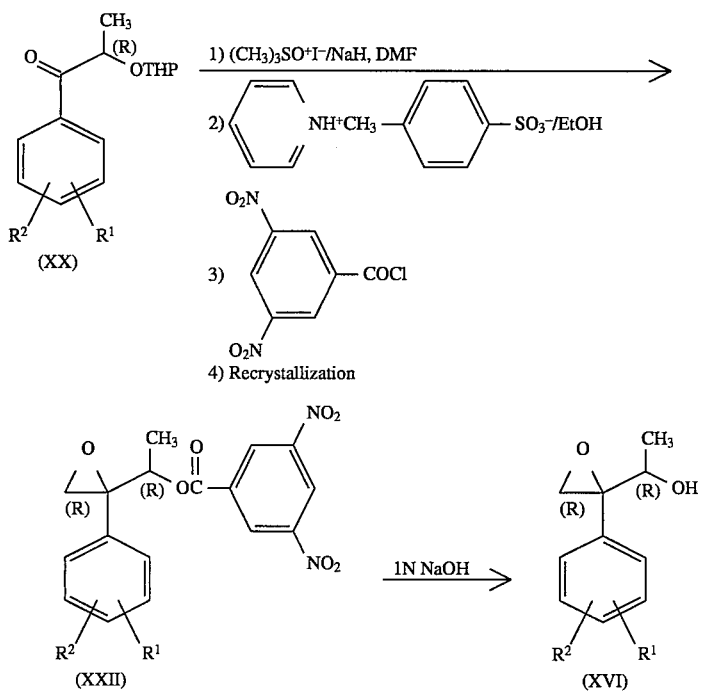

where the symbols have the same meanings as defined above.

The compounds of the formula (IV) can also be prepared with the method shown by the following reaction scheme.

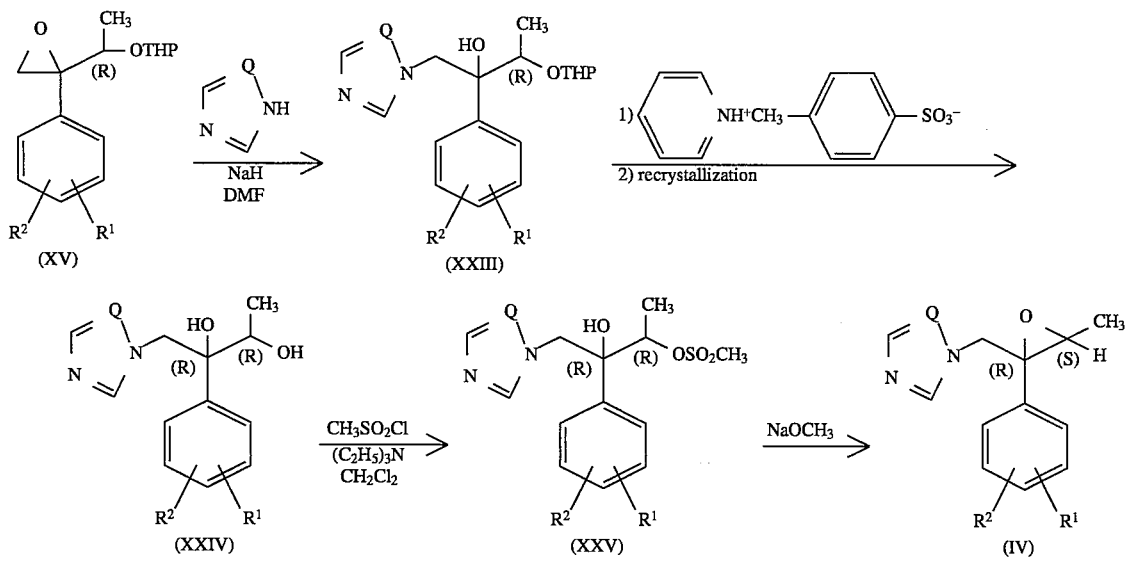

where each symbol is defined as above.

The compound of formula (VI'), which is a compound of the formula (VI) where

is 1H-1,2,4-triazol-1-yl group, and $R^3$ is a hydrogen atom, or its salt can be prepared by the method shown by the following reaction scheme.

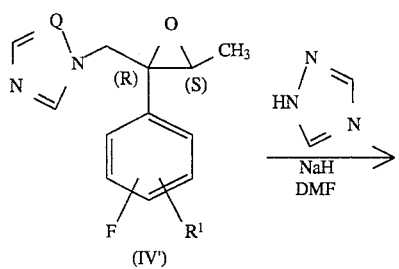
(IV')

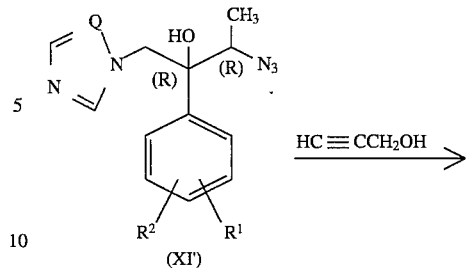
(XI')

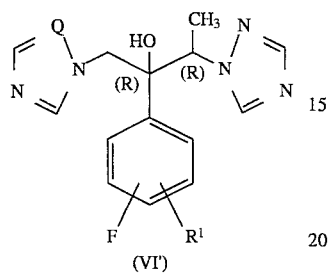
(VI')

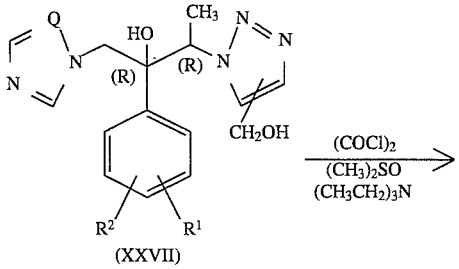
(XXVII)

The compound of the formula (X'), which is a compound of the formula (X) where

is an 1H-1,2,3-triazol-1-yl group, and $R^3$ is a hydrogen atom, or its salt can be prepared by the method shown by the following reaction scheme.

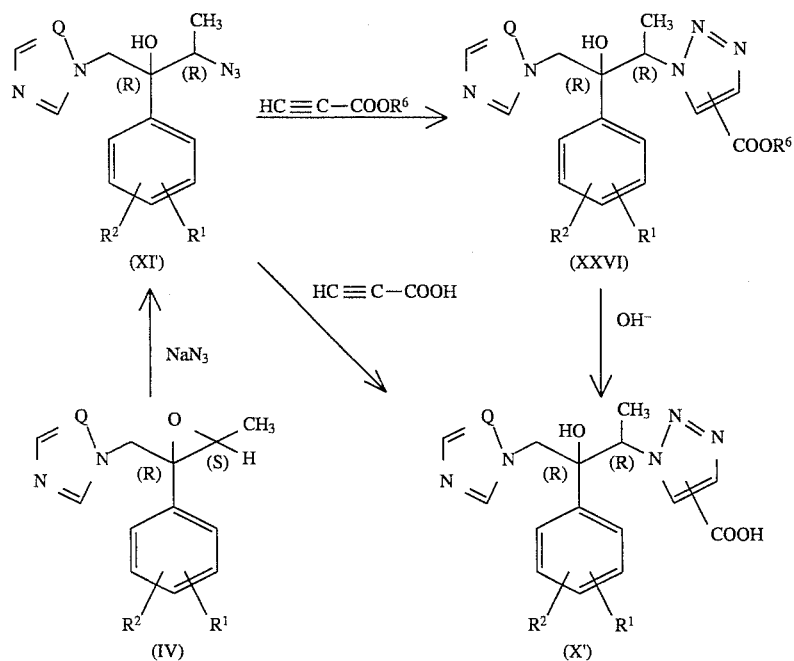

where $R^6$ is a $C_{1-6}$ lower alkyl group (e.g., methyl, ethyl or propyl).

The compound of the formula (XIII) as an intermediate in the present invention, or its salt can be prepared by the method shown by the following reaction scheme.

-continued

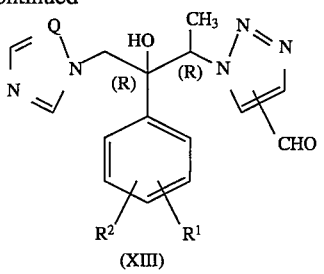

(XIII)

The compound (I) has at least two asymmetric carbon atoms in the molecule; hence there are at least further three kinds of stereoisomers (XXVIII a–c, see the following formulas) besides the compound (I).

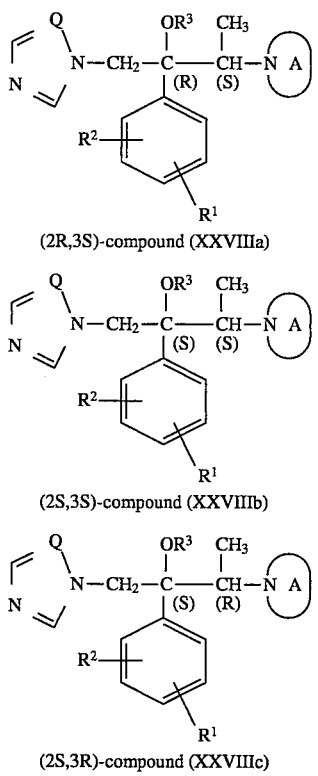

(2R,3S)-compound (XXVIIIa)

(2S,3S)-compound (XXVIIIb)

(2S,3R)-compound (XXVIIIc)

Of these four stereoisomers, the compound (I) of (2R, 3R)-configuration that the present invention is to provide is optically active and most effective as an antifungal agent.

The compound (I), and its salt, having low toxicity and potent antifungal activities with broad spectra can be used for prevention and treatment of fungal infections in human beings, domestic animals and fowls. The compound (I) or its salt is effective particularly for Candida infection, Aspergillus infection, and Cryptococcus infection. The compound (I) and its salt can also be used as antifungal preparations for agricultural use.

The compound (I) or its salt can safely be administered to human beings, e.g., orally or parenterally, in per se or in the form of a pharmaceutically acceptable preparation [e.g., injectable preparations, oral preparations (e.g., tablets, capsules, granules, powders, etc.) external (e.g., nasal, dermatological) preparations, suppositories (e.g., rectal, vaginal), and so on] in admixture with a pharmaceutically acceptable carrier, excipient or diluent.

These preparations can be manufactured by using per se known method in the field of pharmaceutics.

When the compound (I) or its salt is to be processed into an injectable preparation, the injectable preparations may be in the form of oily or aqueous suspension, solution or emulsion, and may contain per se known various additives. Examples of the additives are a dispersing agent [e.g., Tween 80 (Atlas Powder, U.S.A.), HCO-60 (Nikko Chemicals, Japan), carboxymethylcellulose, sodium alginate, etc], a preservative (e.g., methyl-paraben, propyl-paraben, benzyl alcohol, chlorobutanol, etc.), an isotonizing agent (e.g., sodium chloride, glycerin, sorbitol, glucose, etc.), a vegetable oil (e.g., olive oil, sesame oil, peanut oil, cottonseed oil, corn oil, etc.), propylene glycol or the like.

When the compound (I) or its salt is processed into an oral preparation by a per se known method, the compound (I) or its salt is mixed with an excipient (e.g., lactose, sucrose, starch, etc.), disintegrating agent (e.g., starch, calcium carbonate, etc.), binder (e.g., starch, gum arabic, carboxymethylcellulose, polyvinylpyrrolidone, hydroxypropylcellulose, etc.) or/and lubricant (e.g., talc, magnesium stearate, polyethyleneglycol 6000, etc.), and the mixtures are compressed in molds, and then if necessary, the preparations may be coated by a per se known method for the purpose of masking of the taste or providing them with enteric or sustained release property. Usable as coating agents are, for example, hydroxypropylmethylcellulose, ethylcellulose, hydroxymethylcellulose, hydroxypropylcellulose, polyoxyethylene glycol, tween 80, Pluornic F68, cellulose acetate phthalate, hydroxypropylmethylcellulose phthalate, hydroxymethylcellulose acetate succinate, Eudragit (Roehm, Germany; methacrylic acid-acrylic acid copolymer) and pigments such as titanium oxide and ferric oxide.

To manufacture external preparations from the compound (I) or its salt, they are provided solid, semi-solid or liquid state in the conventional manner. To manufacture the solid external preparation for instance, the compound (I) or its salt either as they are or together with an excipient (e.g., glucose, mannitol, starch, microcrystalline cellulose, etc.) and/or thickener (e.g., natural mucilages, cellulose derivatives, polyacrylates, etc.) are processed into a powdery composition. To make a liquid external preparation, the compound (I) or its salt is processed into an oily or aqueous suspension, solution or emulsion in substantially the same manner as in the case of injections. The semi-solid preparation may be an aqueous or oily gel or ointment. In any case, there may be added a pH adjusting agent (e.g., carbonic acid, phosphoric acid, citric acid, hydrochloric acid, sodium hydroxide, etc.), a preservative (e.g., p-hydroxybenzoic acid esters, chlorobutanol, benzalkonium chloride, etc.), etc.

A suppository of the compound (I) or its salt, whether in oily or aqueous solid or semi-solid state or in liquid state, can be produced in the per se conventional manner. The kind of oleagenous base for such composition is optional only if it will not dissolve the compound (I) or its salt. Thus, for example, higher fatty acid glycerides [e.g., cacao butter, Witepsol (Dynamit-Novel, Germany), etc.], intermediate fatty acids [e.g., Miglyol (Dynamit-Novel), etc.] and vegetable oils (e.g., sesame oil, soybean oil, cottonseed oil, etc.) may be mentioned. The aqueous base is exemplified by polyethylene glycol and propylene glycol, while the aqueous gel base may be selected from among natural mucilages, cellulose derivatives, vinyl polymers, polyacrylates, etc.

A daily dosage of the present compound (I) or its salt is not specifically limited, since it depends upon the state of infection, administration route and the like. In the case of the oral dose for treatment of Candida infection for an adult (50 kg weight), the daily dosage lies in the range of about 0.01 to 100 mg/kg per day, preferably about 0.1 to 50 mg/kg per day, more preferably about 0.1 to 20 mg/kg per day.

The compound (I) or its salt can be used in an amount of about 0.1 to 100 mg per 1 g of the external preparation, which can be used for sterilization or disinfection of skin and mucous membrane.

In case of using the compound (I) or its salt as an agricultural antifungal preparation, examples of the preparations include emulsions, wettable powders, powders, granules and the like. These preparations can be formulated in accordance with a conventional method, e.g., by dissolving or dispersing the compound (I) or its salt in a suitable liquid carrier (e.g., solvent) or mixing it with or being adsorbing to a suitable solid carrier (e.g., diluent or dust diluent), and optionally adding an emulsifying agent, suspending agent, spreader, penerating agent, wetting agent, mucilage or stabilizing agent.

Examples of the liquid carriers to be used are water, alcohols (e.g., methyl alcohol, ethyl alcohol, n-propyl alcohol, isopropyl alcohol or ethylene glycol), ethers (e.g., dioxane or tetrahydrofuran), aliphatic hydrocarbons (e.g., kerosene or fuel oil), aromatic hydrocarbons (e.g., benzene or toluene), halogenated hydrocarbons (e.g., methylene chloride or chloroform), acid amides (e.g., dimethylformamide or dimethylacetoamide), esters (e.g., ethyl acetate or butyl acetate), nitriles (e.g., acetonitrile or propionitrile). These carriers can be used singly or as a mixture thereof in which two or more carriers are mixed in a suitable ratio.

Examples of the solid carriers are vegetable powders (e.g., soybean flour, tobacco flour or wheat flour), mineral powders (e.g., kaolin or bentonite), alumina, sulfur powders, activated charcoals or the like. These carriers may be used singly or as a mixture thereof in which two or more carriers are mixed in a suitable ratio.

The amount of the compound (I) or its salt is, for example, about 25 to 150 g per 1 are, preferably about 40 to 80 g per are for prevention of blast.

The present invention will be explained herebelow with reference to the following Reference Examples, Examples, Preparations and Experiments.

$^1$H-NMR spectra were measured with a 200 MHz spectrometer using tetramethylsilane as an internal standard. All the spectra are expressed in the unit ppm.

The ratio of the solvent in the chromatography is a volume ratio. The symbol "%" represents parts by weight if not specified.

The symbols as stated below in Reference Examples, Examples each have a meaning as follows:

s: singlet, d: doublet, t: triplet, q: quartet, dd: double doublet, m: multiplet, br: broad, J: coupling constant

REFERENCE EXAMPLE 1

To a solution of (1R)-1-[(2R)-2-(2,4-difluorophenyl)-2-oxiranyl]ethanol (16.1 g) in tetrahydrofuran (320 ml) were added triphenylphosphine (63.3 g), benzoic acid (29.5 g) and diethyl azodicarboxylate (42.0 g) under ice-cooling. The mixture was stirred for 6 hours at room temperature under argon atmosphere. To the reaction mixture were added ethyl acetate (800 ml) and water (500 ml). The separated aqueous layer was extracted with ethyl acetate (200 ml). The combined organic layers were washed with water and a saturated saline, dried over magnesium sulfate and concentrated. The residue was subjected to silica gel column chromatography (eluent: hexane/ethyl acetate=15:1→7:1) for purification to give [(1S)-1-[(2R)-2-(2,4 -difluorophenyl)-2-oxiranyl]ethyl] benzoate (19.2 g) as a colorless oily substance.

$^1$H-NMR(CDCl$_3$) δ: 1.37 (3H,d,J=6.6 Hz), 2.90 (1H,d,J=5.2 Hz), 3.28 (1H,d,J=5.2 Hz), 5.36 (1H,q,J=6.6 Hz), 6.74–6.94 (2H,m), 7.38–7.60 (4H,m), 7.94–8.01 (2H,m)

IR $v_{max}^{neat}$ cm$^{-1}$: 1725, 1615, 1600, 1505, 1450, 1425

This product (15.9 g) was dissolved in methanol (800 ml). To the solution was added 28% sodium methylate-methanol solution (12.9 ml) under ice-cooling. The mixture was stirred for six hours at room temperature. After addition of 1N hydrochloric acid (63.2 ml), the reaction mixture was distilled under reduced pressure. The residue was subjected to silica gel chromatography (eluent: hexane/ethyl acetate= 6:1→2:1) to give (1S)-1-[(2R)-2 -(2,4-difluorophenyl)-2-oxiranyl]ethanol (9.7 g) as a colorless oily substance.

$^1$H-NMR(CDCl$_3$) δ: 1.20 (3H,dd,J=6.4,2.2 Hz), 2.24 (1H, d,J=1 Hz), 2.92 (1H,d,J=5 Hz), 3.28 (1H,d,J=5 Hz), 4.12 (1H,q,J=6.4 Hz), 6.77–6.95 (2H,m), 7.34 (1H,m)

IR $v_{max}^{neat}$ cm$^{-1}$: 3420, 2980, 1615, 1600, 1500, 1425

REFERENCE EXAMPLE 2

To a solution of (1S)-1-[(2R)-2-(2,4-difluorophenyl)-2-oxiranyl]ethanol (1.06 g) in dichloromethane (30 ml) was added diisopropylethylamine (1.01 ml) at −78° C. under nitrogen atmosphere, to which trifluoromethanesulfonic anhydride (0.97 ml) was added dropwise over the period of 3 minutes. After stirring for 20 minutes at −78° C. and for 20 minutes at −20° C., the mixture was concentrated to about 5 ml at −10° C. The concentrate was subjected to silica gel flash column chromatography (4×5 cm), eluting with dichloromethane-hexane (1:1). The fraction containing the product was concentrated to about 5 ml. The residue was added at −10° C. to a solution of sodium salt of tetrazole prepared from tetrazole (371 mg), dimethylformamide (4.2 ml) and 60% sodium hydride in oil (136 mg), and the mixture was stirred for 10 minutes at −10° C. and for 20 minutes at 0° C. After addition of water (50 ml), the mixture was extracted four times with ethyl acetate (50 ml). The extract was washed twice with water (30 ml) and once with a saturated saline, dried over anhydrous magnesium sulfate and distilled under reduced pressure to give a colorless oily substance. The substance was purified by silica gel column chromatography (eluent: hexane/ethyl acetate=4:1→1:1→2:1) to give (2S)-2-(2,4-difluorophenyl)-2-[(1R)-1-(2H-tetrazol-2-yl)ethyl]oxirane (0.42 g) and (2S)-2-(2,4-difluorophenyl)-2-[(1R)-1-(1H-tetrazol-1-yl)ethyl]oxirane (0.25 g), respectively.

(2S)-2-(2,4-difluorophenyl)-2-[(1R)-1-(2H-tetrazol-2-yl) ethyl]oxirane: a colorless oily substance $^1$H-NMR(CDCl$_3$) δ: 1.76 (3H,dd,J=7.2,1.2 Hz), 2.93 (1H, d,J=4.6 Hz), 2.98 (1H,d,J=4.6 Hz), 5.41 (1H,q,J=7.2 Hz), 6.72–7.15 (3H,m), 8.52 (1H,s)

EI-MS (m/z): 252 (M$^+$)

IR $v_{max}^{neat}$ cm$^{-1}$: 3150, 3060 1620 1600 1506, 1480

(2S)-2-(2,4-difluorophenyl)-2-[(1R)-1-(1H-tetrazol-1-yl) ethyl]oxirane: colorless prisms mp: 118°–122° C.

$^1$H-NMR(CDCl$_3$) δ: 1.69 (3H,dd,J=7.2,1–2 Hz), 2.58 (1H,d,J=4.0 Hz), 2.84 (1H,d,J=4.0 Hz), 5.27 (1H,q,J=7.2 Hz), 6.75–7.20 (3H,m), 8.71 ( 1H,s )

IR $v_{max}^{neat}$ cm$^{-1}$: 3150, 3060, 1620, 1600, 1506, 1489

EI-MS (m/z): 252 (M$^+$)

REFERENCE EXAMPLE 3

Using (1S)-1-[(2R)-2-(2,4-difluorophenyl)-2-oxiranyl] ethanol (569 mg) and pyrazole, (2S)-2-(2,4-difluorophenyl)-2 -[(1R)-1-(1H-pyrazol-1-yl)ethyl]oxirane (166 mg) was obtained by the same way as in Reference Example 2.

¹H-NMR(CDCl₃) δ: 1.57 (3H,dd,J=7.2,1.2 Hz), 2.43 (1H, d,J=4.8 Hz), 2.71 (1H,d,J=4.8 Hz), 4.91 (1H,q,J=7.2 Hz), 6.26 (1H,t,J=2 Hz), 6.74–6.90 (2H,m), 7.01–7.18 (1H,m), 7.44 (1H,d,J=2 Hz), 7.50 (1H,d,J=2 Hz)

IR $v_{max}^{neat}$ cm⁻¹: 3081, 3025, 1618, 1600, 1508, 1480

REFERENCE EXAMPLE 4

Using (1S)-1-[(2R)-2-(2,4-difluorophenyl)-2-oxiranyl]ethanol (497 mg) and 1H-1,2,3-triazole, (2S)-2-(2,4-difluorophenyl)-2-[(1R)-1-(2H-1,2,3-triazol-2-yl)ethyl]oxirane (150 mg) and (2S)-2-(2,4-difluorophenyl)-2-[(1 R)-1-(1H-1,2,3-triazol-1-yl)ethyl]oxirane (204 mg) were obtained by the same way as in Reference Example 2.

(2S)-2-(2,4-difluorophenyl)-2-[(1R)-1-(2H-1,2,3-triazol-2-yl)ethyl]oxirane: colorless prisms ¹H-NMR(CDCl₃) δ: 1.68 (3H,dd,J=7.2,1.2 Hz), 2.83 (1H, d, J=4.6 Hz), 2.86 (1H, d, J=4.6 Hz), 5.17 (1H,q,J=7.2 Hz), 6.69–6.86 (2H,m), 6.94–7.10 (1H,m), 7.61 (2H,s)

IR $v_{max}^{KBr}$ cm⁻: 3056, 2993, 1621, 1603, 1508, 1479

(2S)-2-(2,4-difluorophenyl)-2-[(1R)-1-(1H-1,2,3-triazol-1-yl)ethyl]oxirane: a colorless oily substance ¹H-NMR(CDCl₃) δ: 1.64 (3H,dd,J=7.2,1.2 Hz), 2.46 (1H, d,J=4.4 Hz), 2.76 (1H,d,J=4.4 Hz), 5.32 (1H, q, J=7.2 Hz), 6.80–6.95 (2H,m), 7.08–7.25 (1H,m), 7.67 (1H,d,J=1.2 Hz), 7.77 (1H,d,J=1.2 Hz)

IR $v_{max}^{neat}$ cm⁻¹: 3050, 2944, 1621, 1616, 1601, 1457

REFERENCE EXAMPLE 5

To a solution of (1R)-1-[(2R)-2-(2,4-difluorophenyl)-2-oxiranyl]ethanol (15.43 g) in methylene chloride was added dropwise triethylamine (11.72 ml) under ice-cooling. To the mixture was added dropwise methanesulfonyl chloride (6.8 ml). The mixture was stirred for 45 minutes at room temperature, washed with water and a saturated aqueous sodium hydrogen carbonate solution and dried. The solvent was removed under reduced pressure. The residue was dissolved in N,N-dimethylformamide (50 ml) and used in the following reaction.

Imidazole (7.4 g) was added portionwise to a dispersion of 60% sodium hydride in oil (4.3 g) in N,N-dimethylformamide (150 ml) under nitrogen atomosphere and ice-cooling. The mixture was stirred for 15 minutes. To the mixture which terminated hydrogen evolution was added the solution of the crude product in N,N-dimethylformamide obtained above. Then the mixture was stirred for 6 hours at room temperature. The reaction mixture was poured into ice water, and then extracted with ethyl acetate. The extract was washed with water, dried and distilled under reduced pressure. The residue was purified by silica gel column chromatography (silica gel 150 g, eluent: ethyl acetate/hexane= 3:1→ethyl acetate/methanol=19:1). The fraction containing the product was concentrated, followed by crystallization of the residne from hexane to give [(2R,3S)-2-(2,4-difluorophenyl)-3 -methyl-2-[(1-imidazolyl)methyl]oxirane (15.1 g) as colorless needles.

mp: 76°–78° C.

¹H-NMR(CDCl₃) δ: 1.61 (3H,d,J=5.2 Hz), 3.15 (1H,q,J= 5.2 Hz), 4.17 (1H,d,J=14 Hz), 4.64 (1H,d,J=14 Hz), 6.66–6.83 (3H,m), 6.93–7.04 (2H,m), 7.29 (1H,s)

REFERENCE EXAMPLE 6

1H-1,2,4-Triazole (5.4 g) was added portionwise to a stirred dispersion of 60% sodium hydride in oil (2.86 g) in N,N-dimethylformamide (120 ml) under ice-cooling in a stream of nitrogen, followed by further stirring for 15 minutes. To the mixture which terminated evolution of hydrogen was added (2R,3S)-2-(2,4-difluorophenyl)-3-methyl-2 -[(1H-1,2,4-triazol-1-yl)methyl]oxirane (9 g). The mixture was stirred for 12 hours at 80° C. After cooling, the reaction mixture was poured into ice water, and then extracted twice with ethyl acetate. The extract was washed with water and a saturated saline, dried and distilled under reduced pressure. To the residue was added diethyl ether. The precipitated crystals were collected by filtration, washed with a little amount of diethyl ether and dried to give (2R,3R)-1,3-bis(1H-1,2,4-triazol-1-yl)-2-(2,4-difluorophenyl)butan-2-ol (7.2 g) as colorless needles.

mp: 115°–116° C.

¹H-NMR(CDCl₃) δ: 1.39 (3H,d,J=7.2 Hz), 3.71 (1H, d, J=14 Hz), 4.90 (1H, d, J=14 Hz), 5.19 (1H, q, J=7.2 Hz), 5.49 (1H,s), 6.75–6.86 (1H,m), 7.43–7.55 (2H,m), 7.73 (1H,s), 7.78 (1H,s), 8.00 (1H,s), 8.43 (1H,s)

REFERENCE EXAMPLE 7

Using (1S)-1-[(2R)-2-(2,4-difluorophenyl)-2-oxiranyl]ethanol (1.03 g) and purine (500 mg), (2S)-2-(2,4 -difluorophenyl)-2-[(1R)-1-(9H-9-purinyl)ethyl]oxirane (600 mg) was obtained by the same way as in Reference Example 2.

IR $v_{max}^{neat}$ cm⁻¹: 3090, 3000, 1618, 1595, 1506

¹H-NMR (CDCl₃) δ: 1.68 (3H,d,J=7.2 Hz), 2.39 (1H,d, J=4.4 Hz), 2.71 (1H,d,J=4.4 Hz), 5.58 (1H,q,J=7.2 Hz), 6.82–6.99 (2H,m), 7.25–7.40 (1H,m), 8.15 (1H,s), 9.03 (1H,s), 9.17 (1H,s)

REFERENCE EXAMPLE 8

Using (1S)-1-[(2R)-2-(2,4-difluorophenyl)-2-oxiranyl]ethanol (981 mg) and 1H-imidazo[4,5-b]pyridine (472 mg), (2S)-2-(2,4-difluorophenyl)-2-[(1R)-1-(3H-3-imidazo[4,5-b]pyridyl)ethyl]oxirane (501 mg) and (2S)-2-(2,4-difluorophenyl)-2-[(1R)-1-(1H-1-imidazo[4,5 -b]pyridyl)ethyl]oxirane (271 mg) were obtained by the same way as in Reference Example 2.

(2S)-2-(2,4-difluorophenyl)-2-[(1R)-1-(3H-3-imidazo [4,5 -b]pyridyl)ethyl]oxirane (501 mg)

IR $v_{max}^{neat}$ cm⁻¹: 3100, 1699, 1685, 1558

¹H-NMR(CDCl₃) δ: 1.65 (3H,d,J=7.4 Hz), 2.36 (1H,d,J= 4.6 Hz), 2.66 (1H,d,J=4.6 Hz), 5.66 (1H, q, J=7.4 Hz), 6.81–6.98 (2H,m), 7.23–7.44 (2H,m), 8.09 (1H,dd,J=8.6, 1.4 Hz), 8.11 (1H,s), 8.44 (1H,dd,J=4.8,1.4 Hz)

(2S)-2-(2,4-difluorophenyl)-2-[(1R)-1-(1H-1-imidazo [4,5 -b]pyridyl)ethyl]oxirane (271 mg)

IR $v_{max}^{neat}$ cm⁻¹: 3100, 3000 1616, 1608, 1558

¹H-NMR(CDCl₃) δ: 1.73 (3H,dd,J=7.2,1.2 Hz), 2.40 (1H, d, J=4.6 Hz), 2.71 (1H,d,J=4.6 Hz), 4.95 (1H,q,J=7.2 Hz), 6.85–6.98 (2H,m) , 7.04–7.33 (2H,m), 7.93 (1H,dd,J=8.2, 1.6 Hz), 8.09 (1H,s), 8.62 (1H,dd,J=4.8,1.6 Hz)

REFERENCE EXAMPLE 9

Using (1S)-1-[(2R)-2-(2,4-difluorophenyl)-2-oxiranyl]ethanol (1.17 g) and 1H-1,2,4-triazole (404 mg), (2S)-2-(2,4 -difluorophenyl)-2-[(1R)-1-(1H-1,2,4-triazol-1-yl)ethyl]oxirane (830 mg) was obtained by the same way as in Reference Example 2.

IR $v_{max}^{neat}$ cm⁻¹: 3100, 3000, 1618, 1506

¹H-NMR(CDCl₃) δ: 1.62 (3H,d,J=7.2 Hz), 2.64 (1H,d,J= 4.4 Hz), 2.80 (1H,d,J=4.4 Hz), 4.92 (1H,q,J=7.2 Hz), 6.76–6.91 (2H,m), 7.01–7.18 (1H,m), 7.93 (1H,s), 8.11 (1H,s)

REFERENCE EXAMPLE 10

To a solution of (1S)-1-[(2R)-2-(2,4-difluorophenyl)-2-oxiranyl]ethanol (200 mg) in tetrahydrofuran (5 ml) were added triphenylphosphine (787 mg), tetrazole (210 mg) and diethyl azodicarboxylate (0.47 ml) at 0° C. under argon atmosphere. The mixture was stirred for 16 hours at room temperature. To the reaction mixture were added ethyl acetate (30 ml) and water (15 ml). The separated aqueous layer was extracted with ethyl acetate (20 ml). The combined organic layers were washed with water and saturated saline, dried (MgSO₄) and concentrated. The residue was purified by silica gel column chromatography (eluent: hexane/ethyl acetate=4:1→3:1→2:1) to give (2S)-2-(2,4-difluorophenyl)-2-[(1R)-1-(2H-tetrazol-2-yl)ethyl]oxirane (176 mg).

REFERENCE EXAMPLE 11

Using (1S)-1-[(2R)-2-(2,4-difluorophenyl)-2-oxiranyl] ethanol (202 mg) and 1H-1,2,3-triazole (0.17 ml), (2S)-2-(2,4-difluorophenyl)-2-[(1R)-1-(2H-1,2,3-triazol-2-yl) ethyl]oxirane (172 mg) was obtained by the same way as in Reference Example 10.

REFERENCE EXAMPLE 12

A solution of 2-[(1R)-1-(3,4,5,6-tetrahydro-2H-pyran-2-yloxyethyl]-2-(2,4-difluorophenyl)oxirane (82 g: prepared by a method disclosed in Japanese Unexamined Patent Publication No. 74168(1992)) and pyridinium p-toluenesulfonate (6.3 g) in ethanol (600 ml) was stirred for an hour at 55° C. The reaction mixture was concentrated under reduced pressure. The residue was dissolved in ethyl acetate (1 liter) and washed twice with water (200 ml). The aqueous layer was extracted twice with ethyl acetate (200 ml). The combined organic layers were washed with saturated saline, dried over magnesium sulfate and distilled under reduced pressure. The residue was purified by silica gel column chromatography (eluent: hexane/ethyl acetate=10:1→8:1→3:1) to give (1R)-1-[2-(2,4-difluorophenyl)-2-oxiranyl]ethanol (31.5 g) as a pale yellow oily substance.

¹H-NMR(CDCl₃) δ: 1.14–1.23 (3H,m), 1.77,2.22 (1H, OH), 2.80,2.92 (1H), 3.2.7–3.32(1H), 4.00–4.20 (1H,m), 6.75–6.94 (2H,m), 7.36–7.48 (1H,m)

This product (31.5 g) and 3,5-dinitrobenzoyl chloride (40 g) were dissolved in methylene chloride (500 ml). To the solution was added dropwise triethylamine (24.1 ml) under ice-cooling. After stirring for 3.5 hours at room temperature, the mixture was washed with water (150 ml) and 5% aqueous sodium hydrogen carbonate solution (150 ml), dried over magnesium sulfate and concentrated under reduced pressure. The precipitated crystals were collected by filtration and washed with methylene chloride. The mother liquor and washings were combined and distilled under reduced pressure. To the residue were added ethyl acetate (25 ml) and methanol (300 ml). The mixture was ice-cooled. The precipitate was collected by filtration and recrystallized from a mixture of ethyl acetate (25 ml) and methanol (250 ml) to give [(1R)-1-[(2R)-2-(2,4-difluorophenyl)-2-oxiranyl]ethyl]3,5-dinitrobenzoate (28.7 g) as colorless needles.

mp: 104°–107° C. (recrystallized from ethyl acetate-hexane)

¹H-NMR(CDCl₃) δ: 1.46 (3H,dd,J=6.6 Hz,J=1.2 Hz), 3.01 (1H,d,J=4.6 Hz), 3.23 (1H,d,J=4.6 Hz), 5.33 (1H,q,J= 6.6 Hz), 6.85–7.07 (2H,m), 7.54 (1H,m), 9.13 (2H,d,J=2.2 Hz), 9.25 (1H,t,J=2.2 Hz)

REFERENCE EXAMPLE 13

[(1R)-1-[(2R)-2-(2,4-Difluorophenyl)-2-oxiranyl]ethyl]3, 5-dinitrobenzoate (50 g) was dissolved in methanol (2 liters). To the solution was added dropwise 1N sodium hydroxide aqueous solution (255 ml) at room temperature. The mixture was stirred for an hour at room temperature and neutralized with 1N hydrochloric acid (127 ml). Methanol was distilled off under reduced pressure. To the residue were added ethyl acetate (1 liter) and water (200 ml). The mixture was extracted with ethyl acetate. The organic layer was washed with saturated saline (200 ml), dried over magnesium sulfate and distilled under reduced pressure to remove the solvent. The residue was purified by silica gel column chromatography (eluent: ethyl acetate/hexane=1:3) to give (1R)-1-[(2R)-2-(2,4-difluorophenyl)-2-oxiranyl]ethanol (25 g) as a pale yellow oily substance.

¹H-NMR(CDCl₃) δ: 1.17 (3H,dd,J=6.6,1.2 Hz), 2.05 (1H, bs), 2.80 (1H,d,J=5.2 Hz), 3.30 (1H,d,J=5.2 Hz), 4.01–4.17 (1H,m), 6.75–6.93 (2H,m), 7.36–7.48 (1H,m)

REFERENCE EXAMPLE 14

To a solution of 1-bromo-4-chlorobenzene (20 g) in tetrahydrofuran (260 ml) was added magnesium (turnings, 7.47 g). The mixture was vigorously stirred at room temperature. When the temperature of the mixture reached 40° C., the reaction vessel was cooled in a water bath. A solution of 1-bromo-4-chlorobenzene (38.9 g) in tetrahydrofuran (90 ml), was added dropwise to the mixture at 34°–40° C., followed by stirring for an hour at 30° C. To the mixture was added dropwise a solution of 4-[(2R)-2-(3,4,5,6-tetrahydro-2H-pyran-2-yloxy)propionyl]morpholine (60 g) in tetrahydrofuran (60 ml) over the period of 15 minutes at 0° C. The mixture was stirred for 3 hours at room temperature. To the reaction mixture were added a saturated aqueous ammonium chloride solution (120 ml) and water (100 ml). The mixture was extracted with ethyl acetate (500 ml). The organic layer was washed with water, dried over magnesium sulfate and distilled under reduced pressure. The residue was purified by silica gel column chromatography (silica gel 900 g, eluent: hexane/ethyl acetate=30:1→10:1) to give (2R)-4'-chloro-2-(3,4,5,6-tetrahydro-2H-pyran-2-yloxy)propiophenone (66 g) as a pale yellow oily substance.

¹H-NMR(CDCl₃) δ: 1.46, 1.52 (3H,d,J=7 Hz), 1.1–2.1 (6H,m), 3.30–4.02 (2H,m), 4.57–4.76 (1H,m), 4.90,5.15 (1H,q,J=7 Hz), 7.30–7.60 (2H,m), 7.85–8.20 (2H,m),

REFERENCE EXAMPLES 15–18

The compounds shown in Table 1 were also prepared by a procedure similar to that described in Reference Example 14.

TABLE 1

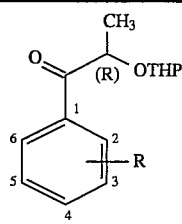

| Reference Example No. | R | |
|---|---|---|
| 15 | 4-F | pale yellow oily substance<br>$^1$H-NMR(CDCl$_3$)δ: 1.46, 1.53(3H, d, J=7.0Hz), 1.40–1.92(6H, m), 3.31–3.58(1H, m), 3.63–3.96(1H, m), 4.55–4.80(1H, m), 4.92, 5.17(1H, q, J=7.0Hz), 7.06–7.18(2H, m), 8.03–8.17(2H, m) |
| 16 | 4-CF$_3$ | pale yellow oily substance<br>$^1$H-NMR(CDCl$_3$)δ: 1.48, 1.54(3H, d, J=7.0Hz), 1.36–1.92(6H, m), 3.31–3.58(1H, m), 3.63–3.97(1H, m), 4.58–4.78(1H, m), 4.92, 5.18(1H, q, J=7.0Hz), 7.70–7.76(2H, m), 8.14(1H, d, J=8.2Hz), 8.21(1H, d, J=8.2Hz) |
| 17 | 4-OCF$_3$ | pale yellow oily substance<br>$^1$H-NMR(CDCl$_3$)δ: 1.47, 1.52(3H, d, J=7Hz), 1.33–2.0(6H, m), 3.30–4.00(2H, m), 4.55–4.85(1H, m), 4.91, 5.16(1H, q, J=7Hz), 7.20–7.38(2H, m), 8.07–8.24(2H, m), IRν$_{max}^{neat}$ cm$^{-1}$: 1699 |
| 18 | 2-Cl | pale yellow oily substance<br>$^1$H-NMR(CDCl$_3$)δ: 1.42, 1.51(3H, d, J=7Hz), 1.30–1.88(6H, m), 3.48–3.62(1H, m), 3.85–3.96(1H, m), 4.69–4.90(1H, m), 5.02, 5.14(1H, q, J=7Hz), 7.24–7.53(4H, m), |

REFERENCE EXAMPLE 19

In tetrahydrofuran (100 ml) were dissolved 1-bromo-2-fluorobenzene (5.6 ml), ethyl bromide (0.37 ml) and 4-[(2R)-2-(3,4,5,6-tetrahydro-2H-pyran-2-yloxy)propionyl] morpholine (11.3 g). To the mixture was added magnesium (turnings, 1.33 g). The mixture was stirred for 2 hours at room temperature. To the reaction mixture were added a saturated aqueous ammonium chloride solution (40 ml) and water (40 ml). The mixture was extracted with ethyl acetate (200 ml). The organic layer was washed with water, dried over magnesium sulfate and distilled under reduced pressure. The residue was purified by silica gel column chromatography (eluent: hexane/ethyl acetate=10:1→8:1) to give (2R)-2'-fluoro-2-(3,4,5,6-tetrahydro-2H-pyran-2-yloxy)propiophenone (8.7 g) as a pale yellow oily substance.

$^1$H-NMR(CDCl$_3$) δ: 1.43, 1.56 (3H,d,J=7 Hz), 1.39–2.01 (6H,m), 3.32–3.61 (1H,m), 3.71–3.98 (1H,m), 4.65–4.88 (1H,m), 4.97,5.19, (1H,q,J=7 Hz), 7.08–7.29 (2H,m), 7.46–7.57 (1H,m), 7.83–7.88 (1H,m)

REFERENCE EXAMPLE 20

Trimethylsulfoxonium iodide (67.8 g) was added portionwise to an ice-cooled dispersion of 60% sodium hydride in oil (11.8 g) in dimethyl sulfoxide (450 ml) under nitrogen atmosphere. After stirring for 45 minutes at room temperature, the mixture was again cooled in an ice-water bath. To the mixture was added dropwise a solution of (2R)-4'-chloro-2-(3,4,5,6-tetrahydro-2H-pyran-2-yloxy)propiophenone (69 g) in dimethylsulfoxide (100 ml) over the period of 45 minutes, followed by stirring for 2 hours at room temperature. Cold water (600 ml) was added to the reaction mixture, which was then extracted three times with ethyl acetate (400 ml, 300 ml and 300 ml). The combined extracts were washed twice with water (100 ml) and once a saturated aqueous saline solution (100 ml), dried over anhydrous magnesium sulfate and distilled under reduced pressure, thereby affording a crude product of 2-(4-chlorophenyl)-2-[(1R)-1-(3,4,5,6-tetrahydro-2H-pyran-2-yloxy)ethyl]oxirane (74.5 g) as a pale yellow oily substance.

REFERENCE EXAMPLES 21–25

The following compounds shown in Table 2 were also prepared by a procedure similar to that described in Reference Example 20.

TABLE 2

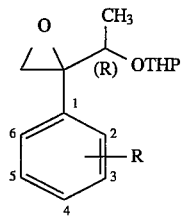

| Reference Example No. | R | |
|---|---|---|
| 21 | 4-F | pale yellow oily substance<br>$^1$H-NMR(CDCl$_3$)δ: 1.10–1.92(9H, m), 2.71–2.80(1H, m), 3.00, 3.34(1H, d, J=6Hz), 3.40–3.60(1H, m), 3.76–3.95(1H, m), 4.07, 4.23(1H, q, J=6.6Hz), 4.69–4.92(1H, m), 6.95–7.08(2H, m), 7.32–7.60(2H, m) |
| 22 | 4-CF$_3$ | pale yellow oily substance<br>$^1$H-NMR(CDCl$_3$)δ: 1.10–1.90(9H, m), 2.72–2.82(1H, m), 3.04–3.60(2H, m), 3.75–3.93(1H, m), 4.15, 4.31(1H, q, J=6.6Hz), 4.68–4.92(1H, m), 7.45–7.75(4H, m), |
| 23 | 4-CCF$_3$ | pale yellow oily substance |
| 24 | 2-Cl | pale yellow oily substance |
| 25 | 2-F | pale yellow oily substance<br>$^1$H-NMR(CDCl$_3$)δ: 1.11–1.26(3H, m), 1.51–1.91(6H, m), 2.82–2.88(1H, m), 3.08, 3.04(1H, d, J=5.4Hz), 3.45–3.55(1H, m), 3.78–4.19(2H, m), 4.76–4.93(1H, m), 6.98–7.58(4H, m) |

REFERENCE EXAMPLE 26

1H-1,2,4-Triazole (42.1 g) was added portionwise to a dispersion of 60% sodium hydride in oil (22.2 g) in dimethylformamide (300 ml) under ice-cooling, followed by stirring for 15 minutes. To the mixture was added a solution of the crude product of 2-(4-chlorophenyl)-2-[(1R)-1-(3,4,5,6-tetrahydro-2H-pyran-2-yloxy)ethyl]oxirane (52 g) in dimethylformamide (50 ml), followed by stirring for 4 hours at 80° C. After cooling, the reaction mixture was poured into ice water (400 ml) and extracted three times with ethyl acetate (200 ml). The organic layer was washed with water and saturated saline, dried over anhydrous magnesium sulfate and distilled under reduced pressure. The residue was subjected to silica gel column chromatography (eluent: hexane/ethyl acetate=3:2→ethyl acetate/acetone=4:1) to give (3R)-2-(4-chlorophenyl)-3-(3,4,5,6-tetrahydro-2H-pyran-2-yloxy)-1-(1H-1,2,4-triazol-1-yl)-2-butanol (53 g) as a colorless amorphous substance.

This product was dissolved in methanol (500 ml), to which p-toluene sulfonic acid hydrate (28.6 g) was added. The mixture was stirred for an hour at room temperature, neutralized with a saturated sodium bicarbonate solution and concentrated. The residue was extracted three times with ethyl acetate (400 ml). The combined organic layers were washed with saturated saline, dried over anhydrous magnesium sulfate, and distilled under reduced pressure. The precipitate was recrystallized from ethyl acetate to give (2R,3R)-2-(4-chlorophenyl)-1-(1H-1,2,4-triazol-1-yl)-2,3-butanediol (12.5 g) as a colorless powder. The mother liquor was concentrated and purified by silica gel column chromatography (eluent: ethyl acetate/methanol=50:1→10:1) to give (2S,3R)-2-(4-chlorophenyl)-1-(1H-1,2,4-triazol-1-yl)-2,3-butanediol (3.56 g) from the first eluate and (2R,3R)-2-(4-chlorophenyl)-1-(1H-1,2,4-triazol-1-yl)-2,3-butanediol (11.5 g) from a second eluate.

(2R,3R)-2-(4-chlorophenyl)-1-(1H-1,2,4-triazol-1-yl)-2,3-butanediol $^1$H-NMR(CDCl$_3$) δ: 0.97 (3H,d,J=7 Hz), 3.48 (1H,s), 4.12 (1H, q, J=7 Hz), 4.36 (1H, br), 4.54 (1H,d,J=14.2 Hz), 4.71 (1H,d,J=14.2 Hz), 7.16 (2H,d,J=8.8 Hz), 7.23 (2H,d, J=8.8 Hz), 7.87 (1H,s), 7.95 (1H,s)

IR $v_{max}^{KBr}$ cm$^{-1}$: 3380, 1600, 1512, 1493, 1365, 1277, 1203 mp: 90°–91° C.

(2S,3R)-2-(4-chlorophenyl)-1-(1H-1,2,4-triazol-1-yl)2,3-butanediol $^1$H-NMR(CDCl$_3$) δ: 1.04 (3H,d,J=6.4 Hz), 2.72 (1H,d, J=5 Hz), 3.69 (1H,m), 4.44 (1H,s), 4.54 (1H,d,J=14 Hz), 4.75 (1H,d,J=14 Hz), 7.32 (2H,d,J=8.8 Hz), 7.51 (2H,d,J= 8.8 Hz), 7.85 (1H,s), 8.03 (1H,s)

mp: 112°–115° C. (colorless needles: recrystallized from diisopropyl ether)

REFERENCE EXAMPLES 27–31

The following compounds shown in Table 3 were also prepared by a procedure similar to that described in Reference Example 26.

TABLE 3

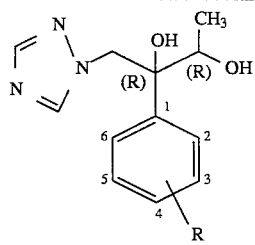

| Reference Example No. | R | |
|---|---|---|
| 27 | 4-F | $^1$H-NMR(CDCl$_3$)δ: 0.97(3H, d, J=6.4Hz), 2.87(1H, d, J=8.2Hz), 4.12(1H, q, J=6.4Hz), 4.33(1H, s), 4.54(1H, d, J=14Hz), 4.72(1H, d, J=14Hz), 6.92–7.03(2H, m), 7.15–7.24(2H, m), 7.72(1H, s), 7.87(1H, s) mp: 102–103° C. (colorless prisms) |
| 28 | 4-CF$_3$ | $^1$H-NMR(CDCl$_3$)δ: 0.97(3H, d, J=6.4Hz), 2.98(1H, d, J=8.0Hz), 4.17(1H, q, J=6.4Hz), 4.49(1H, s), 4.59(1H, d, J=14Hz), 4.75(1H, d, J=14Hz), 7.37(2H, d, J=9Hz), 7.55(2H, d, J=9Hz), 7.75(1H, s), 7.87(1H, s) |

TABLE 3-continued

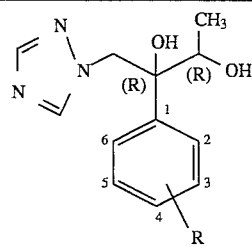

| Reference Example No. | R | |
|---|---|---|
| 29 | 4-OCF$_3$ | mp: 133–135° C. (colorless prisms) $^1$H-NMR(CDCl$_3$)δ: 0.98(3H, d, J=6.4Hz), 2.90(1H, d, J=7.6Hz), 4.14(1H, m), 4.38(1H, s), 4.56(1H, d, J=14.4Hz), 4.73(1H, d, J= 14.4Hz), 7.14(2H, d, J=8.4Hz), 7.20–7.32 (2H, m), 7.75(1H, s), 7.88(1H, s)<br><br>IR$v_{max}^{KBR}$ cm$^{-1}$: 1371, 1279, 1213, 1153<br>1371, 1279, 1213, 1153 |
| 30 | 2-Cl | mp: 103–104° C. (colorless prisms) $^1$H-NMR(CDCl$_3$)δ: 0.94(3H, d, J=6.4Hz), 2.59(1H, d, J=10Hz), 4.82(1H, d, J=14Hz), 4.81–4.92(1H, m), 4.90(1H, s), 5.38(1H, d, J=14Hz), 7.12–7.32(3H, m), 7.56–7.61(1H, m), 7.81(1H, s), 7.82(1H, s) colorless powder |
| 31 | 2-F | $^1$H-NMR(CDCl$_3$)δ: 0.98(3H, d, J=6.4Hz), 2.54(1H, d, J=9.8Hz), 4.32–4.42(1H, m), 4.72 (1H, m), 4.80(1H, d, J=14Hz), 4.89(1H, d, J=14Hz), 6.92–7.03(2H, m), 7.19–7.45(2H, m), 7.80(1H, s), 7.82(1H, s) mp: 65–66° C. (colorless prisms) |

REFERENCE EXAMPLE 32

To a solution of (2R,3R)-2-(4-chlorophenyl)-1-(1H-1,2,4-triazol-1-yl)-2,3-butanediol (12.4 g) and triethylamine (7.6 ml) in ethyl acetate (200 ml) was added dropwise methanesulfonyl chloride (6.25 g) under ice-cooling. After stirring for 45 minutes at room temperature, the reaction mixture was washed with water and saturated saline, dried over magnesium sulfate and distilled under reduced pressure to give (2R,3R)-2-(4-chlorophenyl)-2-hydroxy-1-(1H-1,2,4-triazol-1-yl)-3-butyl methanesulfonate.

This product was dissolved in methanol (150 ml), to which 28% sodium methylate methanolic solution (10.5 g) was added under ice-cooling. After stirring for 15 minutes under ice-cooling, the mixture was concentrated. The residue was extracted with ethyl acetate. The organic layer was washed with water and saturated saline, dried over anhydrous magnesium sulfate and distilled under reduced pressure. The residue was purified by silica gel column chromatography (eluent: ethyl acetate/dichloromethane/methanol=16:4:1), and recrystallized from diisopropyl ether to give (2R,3S)-2-(4-chlorophenyl)-3-methyl-2-(1H-1,2,4-triazol-1-ylmethyl)oxirane (10.2 g) as colorless needles.

$^1$H-NMR(CDCl$_3$) δ: 1.63 (3H,d,J=5.8 Hz), 3.15 (1H,q,J= 5.8 Hz), 4.44 (1H,d,J=14.8 Hz), 4.87 (1H,d,J=14.8 Hz), 7.10 (1H,dt,J=6.6 Hz,J=2.2 Hz), 7.24 (1H,dt,J=6.6 Hz,J=2.2 Hz), 7.87 (1H,s), 7.95 (1H,s)

IR $v_{max}^{KBr}$ cm$^{-1}$: 1597, 1508, 1484, 1344, 1273 mp: 51°–53° C.

REFERENCE EXAMPLES 33–37

The following compounds shown in Table 4 were also prepared by a procedure similar to that described in Reference Example 32.

TABLE 4

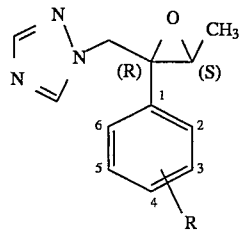

| Reference Example No. | R | |
|---|---|---|
| 33 | 4-F | $^1$H-NMR(CDCl$_3$)δ: 1.64(3H, d, J=5.6Hz), 3.16(1H, q, J=5.6Hz), 4.45(1H, d, J=15Hz), 4.84(1H, d, J=15Hz), 6.89–7.00(2H, m), 7.09–7.19(2H, m), 7.87(1H, s), 7.93(1H, s) mp: 54–55° C. (colorless prisms) |
| 34 | 4-CF$_3$ | $^1$H-NMR(CDCl$_3$)δ: 1.65(3H, d, J=5.6Hz), 3.17(1H, q, J=5.6Hz), 4.47(1H, d, J=15Hz), 4.94(1H, d, J=15Hz), 7.30(2H, d, J=8.0Hz), 7.53(2H, d, J=8.0Hz), 7.87(1H, s), 7.98(1H, s) mp: 81–82° C. (colorless needles) |
| 35 | 4-OCF$_3$ | $^1$H-NMR(CDCl$_3$)δ: 1.64(3H, d, J=5.4Hz), 3.17(1H, q, J=5.4Hz), 4.46(1H, d, J=14.6Hz), 4.88(1H, d, J=14.6Hz), 7.11(2H, d, J=9Hz), 7.21(2H, d, J=9Hz), 7.89(1H, s), 7.97(1H, s) IR $v_{max}^{KBR}$ cm$^{-1}$: 1598, 1512, 1450, 1346, 1272, 1228, 1209 mp: 82–83° C. (colorless needles) |
| 36 | 2-Cl | $^1$H-NMR(CDCl$_3$)δ: 1.66(3H, d, J=5.6Hz), 3.22(1H, q, J=5.6Hz), 4.42(1H, d, J=14Hz), 4.99(1H, d, J=14Hz), 6.92–7.35(4H, m), 7.81 (1H, s), 7.90(1H, s) colorless crystals |
| 37 | 2-F | $^1$H-NMR(CDCl$_3$)δ: 1.65(3H, d, J=5.6Hz), 3.22(1H, q, J=5.6Hz), 4.46(1H, d, J=14Hz), 4.92(1H, d, J=14Hz), 6.98–7.29(4H, m), 7.82(1H, s), 7.93(1H, s) mp: 72–74° C. (colorless needles) |

REFERENCE EXAMPLE 38

Using (1S)-1-[(2R)-2-(2,4-difluorophenyl)-2-oxiranyl] ethanol (523 mg) and 6-methoxypurine ½ hydrate (415 mg), (2S)-2-(2,4-difluorophenyl)-2-[(1R)-1-[6-methoxy-7(7H)purinyl]ethyl]oxirane (205 mg) and (2S)-2-(2,4-difluorophenyl)-2-[(1R)-1-[6-methoxy-9(9H)-purinyl]ethyl] oxirane (183 mg) were obtained as a white powder respectively by the same way as in Reference Example 2.

(2S)-2-(2,4-difluorophenyl)-2-[(1R)-1-[6-methoxy-7(7H)purinyl]ethyl]oxirane $^1$H-NMR(CDCl$_3$) δ: 1.64 (3H,d,J=7.2 Hz), 2.41 (1H,d,J=4.4 Hz), 2.69 (1H,d,J=4.4 Hz), 4.21 (3H,s), 5.50 (1H, q, J=7.2 Hz), 6.81–6.98 (2H,m), 7.21–7.30 (1H,m), 7.95 (1H, s), 8.59 (1H,s)

IR $v_{max}^{KBr}$ cm$^{-1}$: 3060, 1614, 1556, 1477, 1396

SIMS: 333 (M+H)$^+$ (2S)-2-(2,4-difluorophenyl)-2-[(1R)-1-[6-methoxy-9(9H)purinyl]ethyl]oxirane $^1$H-NMR(CDCl$_3$) δ: 1.64 (3H,d,J=7.2 Hz), 2.91 (1H,d,J=4.6 Hz), 2.63 (1H,d,J=4.6 Hz), 4.20 (3H,s), 5.74 (1H,q,J=7.2 Hz), 6.81–6.99 (2H,m), 7.26–7.42 (1H,m), 8.14 (1H,s), 8.67 (1H,s)

IR $v_{max}^{KBr}$ cm$^{-1}$: 3060, 3000, 1614, 1556, 1477, 1396

REFERENCE EXAMPLE 39

Using (1S)-1-[(2R)-2-(2,4-difluorophenyl)-2-oxiranyl] ethanol (587 mg) and 6-methylpurine (353 mg), (2S)-2-(2,4-difluorophenyl)-2-[(1R)-1-[6-methyl-9(9H)-purinyl]ethyl] oxirane (383 mg) was obtained as a white powder by the same way as in Reference Example 2.

$^1$H-NMR(CDCl$_3$) δ: 1.65 (3H,d,J=7.2 Hz), 2.38 (1H,d,J=4.4 Hz), 2.69 (1H,d,J=4.4 Hz), 2.88 (3H,s), 5.54 (1H,q,J=7.2 Hz), 6.81–7.00 (2H,m), 7.24–7.42 (1H,m), 8.07 (1H,s), 8.88 (1H,s)

IR $v_{max}^{KBr}$ cm$^{-1}$: 3050, 1622, 1601, 1583, 1502

SIMS: 317 (M+H)$^+$

REFERENCE EXAMPLE 40

Using (1S)-1-[(2R)-2-(2,4-difluorophenyl)-2-oxiranyl] ethanol (607 mg) and 6-chloropurine (422 mg), (2S)-2-[(1R)-1-[6-chloro-9(9H)-purinyl]ethyl]-2-(2,4-difluorophenyl)oxirane (440 mg) was obtained as a white powder by the same way as in Reference Example 2.

$^1$H-NMR(CDCl$_3$) δ: 1.67 (3H,d,J=7.0 Hz), 2.39 (1H,d,J=4.4 Hz), 2.72 (1H,d,J=4.4 Hz), 5.55 (1H, q, J=7.0 Hz), 6.82–6.99 (2H,m), 7.25–7.40 (1H,m), 8.16 (1H,s), 8.79 (1H,s)

IR $v_{max}^{KBr}$ cm$^{-1}$: 3061, 3047, 1622, 1593, 1564, 1502

SIMS: 337 (M+H)$^+$

REFERENCE EXAMPLE 41

Using (1S)-[(2R)-2-(2,4-difluorophenyl)-2-oxiranyl]ethanol (578 mg) and 2,6-dichloropurine (490 mg), (2S)-2-[(1R)-1-[2,6-dichloro-9(9H)-purinyl]ethyl]-2-(2,4-difluorophenyl)oxirane (168 mg) was obtained by the same way as in Reference Example 2.

$^1$H-NMR(CDCl$_3$) δ: 1.65 (3H,d,J=7.2 Hz), 2.42 (1H,d,J=4.2 Hz), 2.74 (1H,d,J=4.2 Hz), 5.48 (1H,q,J=7.2 Hz), 6.72–6.98 (2H,m), 7.26–7.49 (1H,m), 8.16 (1H,s)

IR $v_{max}^{KBr}$ cm$^{-1}$: 2950, 1620, 1597, 1504, 1427

SIMS: 372 (M+H)$^+$

REFERENCE EXAMPLE 42

A mixture of 1H-1,2,4-triazole (1.17 g), (2R,3S)-2-(2-fluorophenyl)-3-methyl-2-[(1H-1,2,4-triazol-1-yl)methyl] oxirane (2 g), lithium carbonate (6.32 g) and dimethylformamide (40 ml) was stirred for 24 hours at 110° C. After cooling, to the mixture was added ethyl acetate (50 ml). The mixture was filtered to remove insoluble substances. The filtrate was distilled under reduced pressure. The residue was dissolved in ethyl acetate (100 ml). The mixture was washed with saturated saline (30 ml×2). The ethyl acetate layer was dried over anhydrous magnesium sulfate and distilled under reduced pressure. The residue was purified by silica gel chromatography (silica gel 50 g, eluent: ethyl acetate/acetone=4:1) to give (2R,3R)-1,3-bis(1H-1,2,4-triazol-1-yl)-2-(2-fluorophenyl)-2-butanol (1.32 g).

mp: 105°–106° C. (recrystallized from diisopropyl ether)

$^1$H-NMR(CDCl$_3$) δ: 1.39 (3H,d,J=7 Hz), 3.72 (1H,d,J=14 Hz), 4.96 (1H,d,J=14 Hz), 5.21 (1H,q,J=7 Hz), 5.39 (1H,s), 6.99–7.11 (1H,m), 7.22–7.33 (1H,m), 7.44–7.53 (1H,m), 7.72 (1H,s), 7.74 (1H,s), 8.01 (1H,s), 8.45 (1H,s)

$[\alpha]_D^{20}$ −52.5° (c=0.5, methanol)

Elemental Analysis for $C_{14}H_{15}FN_6O$: Calcd.: C, 55.62; H, 5.00; N, 27.80 Found: C, 55.43; H, 4.99; N, 27.83

EXAMPLE 1

(2R,3R)-2-(2,4-Difluorophenyl)-1-(1-imidazolyl)-3-(1-pyrazolyl)-2-butanol (Compound 1)

In dimethylformamide (2 ml) was dispersed 60% sodium hydride in oil (52 mg). Imidazole (89 mg) was added to the dispersion under ice-cooling and the mixture was stirred for 15 minutes at room temperature. To the mixture was added a solution of (2S)-2-(2,4-difluorophenyl)-2-[(1R)-1-(1H-pyrazol-1-yl)ethyl]oxirane (166 mg) in dimethylformamide (1 ml). The mixture was heated for 5 hours at 50° C. and cooled. To the reaction mixture were added cold water (5 ml) and ethyl acetate (30 ml). The separated aqueous layer was extracted twice with ethyl acetate. The combined ethyl acetate layers were washed with water and saturated saline, dried over magnesium sulfate and distilled under reduced pressure. The residue was allowed to stand to crystallize. The obtained crystals were recrystallized from ethyl acetate-hexane to form the title compound (Compound 1, 193 mg) as colorless prisms.

mp: 142°–143° C.

Elemental Analysis for $C_{16}H_{16}F_2N_4O$: Calcd.: C, 60.37; H, 5.07; N, 17.60 Found: C, 60.08; H, 5.25; N, 17.46

$^1$H-NMR (CDCl$_3$) δ: 1.13(3H,d,J=7.0 Hz), 3.30(1H,d,J=14.2 Hz), 4.37(1H,dd,J=14.2,2.2 Hz), 4.98(1H,q,J=7.0 Hz), 6.23(1H,s), 6.38(1H,t,J=2.2 Hz), 6.63(1H,s), 6.70–6.80 (2H, m), 7.15(1H,s), 7.46–7.65(1H,m), 7.60(1H,d,J=2.2 Hz), 7.69 (1H, d, J=2.2 Hz)

IR $v_{max}^{KBr}$ cm$^{-1}$: 3106, 1616, 1506, 1396, 1305

EXAMPLE 2

(2R,3R)-2-(2,4-Difluorophenyl)-3-(1-pyrazolyl)-1-(1H-1,2,4-triazol-1-yl)-2-butanol (Compound 2)

Using (2S)-2-(2,4-difluorophenyl)-2-[(1R)-1-(1-pyrazolyl)ethyl]oxirane (0.12 g) and 1H-1,2,4-triazole (0.1 g), the title compound (Compound 2, 81 mg, 53%) was obtained as a colorless oily substance by the same way in Example 1.

$^1$H-NMR(CDCl$_3$) δ: 1.34 (3H,d,J=7.0 Hz), 3.56 (1H,d,J=14.2 Hz), 4.80 (1H,d,J=14.2 Hz), 5.07 (1H, q, J=7.0 Hz), 5.98 (1H,bs), 6.37 (1H,t,J=2 Hz), 6.75–6.85 (2H,m), 7.44–7.53 (1H,m), 7.62 (1H,d,J=2 Hz), 7.65 (1H,s), 7.69 (1H,d,J=2 Hz), 7.86 (1H,s)

SIMS(m/z): 320 (MH$^+$)

EXAMPLE 3

(2R,3R)-2-(2,4-Difluorophenyl)-3-(1H-tetrazol-t-yl)-1-(1H-1,2,4-triazol-1-yl)-2-butanol (Compound 3)

1H-1,2,4-Triazole (34 mg) was added to a dispersion of 60% oily sodium hydride in oil (19 mg) in dimethylformamide (0.8 ml) under ice-cooling and the resulting mixture was stirred for 10 minutes at room temperature. To the mixture was added a solution of (2S)-2-(2,4-difluorophenyl)-2-[(1R)-1-(1H-tetrazolyl)ethyl]oxirane (62 mg) in dimethylformamide (0.5 ml), followed by heating for 5 hours at 50° C. After cooling, to the reaction mixture were added cold water (10 ml) and ethyl acetate (20 ml). The aqueous layer was extracted twice with ethyl acetate. The combined ethyl acetate layers were washed with water and saturated saline, dried over anhydrous magnesium sulfate and distilled under reduced pressure. The residue was subjected to silica gel column chromatography (ethyl acetate/hexane=1:1→2:1→ethyl acetate). The obtained oily substance was crystallized from a mixture of ethyl acetate and hexane to give the title compound (Compound 3, 12 mg, 15%) as colorless crystals.

$^1$H-NMR(CDCl$_3$) δ: 1.43 (3H,d,J=7.0 Hz), 3.56 (1H,d,J=14.2 Hz), 4.99 (1H,d,J=14.2 Hz), 5.58 (1H,q,J=7.0 Hz), 5.64 (1H,s), 6.75–6.95 (2H,m), 7.36–7.50 (1H,m), 7.71 (1H,s), 7.78 (1H,s), 9.01 (1H,s)

IR $v_{max}^{KBr}$ cm$^{-1}$: 3410, 3062, 1618, 1597

Elemental Analysis for $C_{13}H_{13}F_2N_7O$: Calcd.: C, 48.60; H, 4.08; N, 30.52 Found: C, 48.49; H, 4.40; N, 30.81.

Example 4

(2R,3R)-2-(2,4-Difluorophenyl)-3-(2H-tetrazol-2-yl)-1-(1H- 1,2,4-triazol-1-yl)-2-butanol (Compound 4)

1H-1,2,4-Triazole (48 mg) was added to a dispersion of 60% sodium hydride in oil (27 mg) in dimethylformamide (1.1 ml) under ice-cooling and the resulting mixture was stirred for 10 minutes at room temperature. After addition of a solution of (2S)-2-(2,4-difluorophenyl)-2-[(1R)-1-(2H-tetrazol- 2-yl)ethyl]oxirane (89 mg) in dimethylformamide (0.7 ml), the mixture was heated for 5 hours at 50° C. and cooled. Cold water (10 ml) and ethyl acetate (20 ml) were added to the reaction mixture. The separated aqueous layer was extracted twice with ethyl acetate. The combined organic layers were washed with water and saturated saline, dried over anhydrous magnesium sulfate and distilled under reduced pressure. The residue was purified by silica gel column chromatography (eluent: ethyl acetate/hexane=1:1→ 2:1→ethyl acetate) to give the title compound (Compound 4, 60 mg, 53%) as a colorless oily substance.

$^1$H-NMR (CDCl$_3$)δ: 1.58 (3H,d,J=7.0Hz), 3.79 (1H,d,J=14.2Hz), 5.04 (1H,d,J=14.2Hz), 5.19 (1H,s), 5.69 (1H,q,J=7.0Hz), 6.75–6.90 (2H,m), 7.45–7.61 (1H,m), 7.71 (1H,s), 7.82 (1H,s), 8.63 (1H,s).

IR $v_{max}^{neat}$cm$^{-1}$: 3400, 3050, 1621, 1616, 1597.

EI-MS (m/z): 321 (M$^+$).

This oily substance was dissolved in ethyl ether, followed by addition of hydrogen chloride—ethyl acetate solution. The precipitated white powder was collected by filtration and dried under reduced pressure to give the hydrochloride of Compound 4.

mp: 111°–130° C.

$^1$H-NMR (CDCl$_3$) δ: 1.58 (3H,d,J=7.0Hz), 4.10 (1H,d,J=14.2Hz), 5.11 (1H,d,J=14.2Hz), 5.73 (1H,q,J=7.0Hz), 6.78–6.91 (2H,m), 7.43–7.55 (1H,m), 7.88 (1H,s), 8.67 (1H,s), 8.86 (1H,bs).

IR $v_{max}^{KBr}$ cm$^{-1}$: 3400, 3060, 1620, 1500, 1140.

Elemental Analysis for $C_{13}H_{13}F_2N_7O$ HCl: Calcd.: C, 43.65; H, 3.94; N, 27.41, Found: C, 43.64; H, 3.90; N, 27.20.

Example 5

(2R,3R)-2-(2,4-Difluorophenyl)-1-(1-imidazolyl)-3-(2H-tetrazol- 2-yl)-2-butanol (Compound 5)

Using (2S)-2-(2,4-difluorophenyl)-2-[(1R)-1-(2H-2-tetrazolyl)ethyl] oxirane (101 mg) and imidazole (54 mg), the title compound (Compound 5, 79 mg, 62%) was obtained as colorless prisms by the same way as in Example 1.

mp: 158°–160° C.

$^1$H-NMR (CDCl$_3$) δ: 1.47 (3H,d,J=7.0Hz), 3.40 (1H,d,J=14.6Hz), 4.54 (1H,dd,J=14.6,1.6Hz), 5.15 (1H,s), 5.89 (1H, q,J=7.0Hz), 6.56 (1H,s), 6.69 (1H,s), 6.78–6.96 (2H,m), 7.15 (1H,s), 7.48–7.66 (1H,m), 8.67 (1H,s).

IR $v_{max}^{KBr}$ cm$^{-1}$: 3400, 3050, 1618, 1614, 1513, 1500.

Elemental Analysis for C$_{14}$H$_{14}$F$_2$N$_6$O: Calcd.: C, 52.50; H, 4.41; N, 26.24, Found: C, 52.26; H, 4.39; N, 26.23.

Example 6

(2R,3R)-2-(2,4-Difluorophenyl)-1-(1H-1,2,4-triazol-1-yl)-3 -(1H-1,2,3-triazol-1-yl)-2-butanol (Compound 6)

1H-1,2,4-Triazole (63 mg) was added under ice-cooling to a dispersion of 60% sodium hydride in oil (36 mg) in dimethylformamide (1.5 ml) and the resulting mixture was stirred for 10 minutes at room temperature. To the mixture was added a solution of (2S)-2-(2,4-difluorophenyl)-2-[(1R)-1-(1H-1,2,3-triazol-1-yl)ethyl] oxirane (116 mg) in dimethylformamide (0.8 ml), followed by heating for 5 hours at 50° C. and cooling. Cold water (10 ml) and ethyl acetate (20 ml) were added to the reaction mixture. The separated aqueous layer was extracted twice with ethyl acetate. The combined ethyl acetate layers were washed with water and saturated saline, dried over anhydrous magnesium sulfate and distilled under reduced pressure. The residue was purified by silica gel column chromatography (acetone/dichlormethane=1:2→1:1). The obtained crystals were recrystallized from diisopropyl ether to give the title compound (Compound 6, 66 mg, 45%) as colorless crystals.

$^1$H-NMR (CDCl$_3$) δ: 1.38 (3H,d,J=7.0Hz), 3.49 (1H,d,J=14.4Hz), 4.99 (1H,d,J=14.4Hz), 5.39 (1H,s), 5.52 (1H,q,J=7.0Hz), 6.75–6.90 (2H,m), 7.42–7.59 (1H,m), 7.74 (1H,s), 7.77 (1H,s), 7.81 (1H,s), 7.98 (1H,s).

IR $v_{max}^{KBr}$ cm$^{-1}$: 3315, 3124, 1618, 1599, 1500, 1421.

Elemental Analysis for C$_{14}$H$_{14}$F$_2$N$_6$O: Calcd.: C, 52.50; H, 4.41; N, 26.24, Found: C, 52.35; H, 4.29; N, 26.08.

Example 7

(2R, 3R)-2-(2,4-Difluorophenyl)-1-(1-imidazolyl)-3-(1H-1,2,3 -triazol-1-yl)-2-butanol (Compound 7)

Using (2-S)-2-(2,4-difluorophenyl)-2-[(1R )-1-(1H-1,2,3 -triazol-1-yl)ethyl]oxirane (89 mg) and imidazole (48 mg), the title compound (Compound 7, 96 mg, 85%) was obtained as colorless prisms by the same way as in Example 1.

mp: 150°–151° C.

$^1$H-NMR (CDCl$_3$) δ: 1.36 (3H,d,J=7.0Hz), 3.41 (1H,d,J=14.4Hz), 4.61 (1H,d,J=14.4Hz), 5.46 (1H,q,J=7.0Hz), 6.20 (1H,s), 6.34 (1H,s), 6.80–6.99 (2H,m), 7.01 (1H,s), 7.55–7.71 (1H,m), 7.77 (1H,d,J=1.0Hz), 7.91 (1H,d,J=1.0Hz).

IR $v_{max}^{KBr}$ cm$^{-1}$: 3350, 3077, 1616, 1596, 1502, 1461.

Example 8

(2R,3R)-2-(2,4-Difluorophenyl)-3-(2H-1,2,3-triazol-2-yl)-1-( 1H-1,2,4-triazol-1-yl)-2-butanol (Compound 8)

1H-1,2,4-Triazole (41 mg) was added an ice-cooled dispersion of 60% sodium hydride in oil (23 mg) in dimethylformamide (1 ml) and the resulting mixture was stirred for 10 minutes at room temperature. To the mixture was added a solution of (2S)-2-(2,4-difluorophenyl)-2-[ (1R)-1-(2H-1,2,3-triazol-2-yl)ethyl]oxirane (76 mg) in dimethylformamide (0.8 ml), followed by heating for 5 hours at 50° C. and cooling. To the reaction mixture were added cold water (5 ml) and ethyl acetate (15 ml). The separated aqueous layer was extracted twice with ethyl acetate. The combined ethyl acetate layers were washed with water and saturated saline, dried over anhydrous magnesium sulfate and distilled under reduced pressure. The residue was subjected to silica gel column chromatography (acetone/dichlormethane=1:2→1:1). The obtained oily substance was crystallized from isopropyl ether to give the title compound (Compound 8, 41 mg, 42%) as colorless crystals.

mp: 93°–95° C.

$^1$H-NMR (CDCl$_3$) δ: 1.43 (3H,d,J=7.0Hz), 3.57 (1H,d,J=14.4Hz), 4.91 (1H, dd, J=l 4.4,1.2Hz), 5.29 (1H,s), 5.54 (1H, q, J=7.0Hz), 6.75–6.92 (2H,m), 7.43–7.63 (1H,m), 7.65 (1H,s), 7.77 (2H,s), 7.85 (1H,s).

IR $v_{max}^{KBr}$ cm$^{-1}$: 3340, 3302, 1618, 1500, 1421.

Elemental Analysis for C$_{14}$H$_{14}$F$_2$N$_6$O: Calcd.: C, 52.50; H, 4.41; N, 26.24, Found: C, 52.33; H, 4.47; N, 26.22.

Example 9

(2R,3R)-2-(2,4-Difluorophenyl)-1-(1-imidazolyl)-3-(2H-1,2,3 -triazol-2-yl)-2-butanol (Compound 9)

Using (2S)-2-(2,4-difluorophenyl)-2-[(1R)-1-(2H-1,2,3 -triazol-2-yl)ethyl]oxirane (70 mg) and imidazole (38 mg), the title compound (Compound 9, 85 mg, 95%) was obtained as a colorless oily substance by the same way as in Example 1.

$^1$H-NMR (CDCl$_3$) δ: 1.36 (3H,d,J=7.0Hz), 3.22 (1H,d,J=14.4Hz), 4.46 (1H,dd,J=14.4,1.8Hz), 5.30 (1H,s), 5.60 (1H, q,J=7.0Hz), 6.62 (1H,s), 6.74 (1H,s), 6.75–6.91 (2H,m), 7.16 (1H,s), 7.50–7.66 (1H,m), 7.78 (2H,s).

IR $v_{max}^{neat}$cm$^{-1}$: 3400, 3302, 1616, 1506, 1489.

Example 10

(2R,3R)-2-(2,4-Difluorophenyl)-3-(1H-tetrazol-1-yl)-1-(1H- 1,2,4-triazol-1-yl)-2-butanol (Compound 3) and
(2R,3R)-2-(2,4-difluorophenyl)-3-(2H-tetrazol-2-yl)-1-(1H- 1,2,4-triazol-1-yl)-2-butanol (Compound 4)

A mixture of (2R,3S)-2-(2,4-difluorophenyl)-3-methyl-2 -[(1H-1,2,4-triazol-1-yl)methyl]oxirane (385 mg), tetrazole (129 mg), bis(tri-n-butyltin)oxide (0.05 ml) and toluene (10 ml) was heated for 48 hours at 110°–120° C. under argon atmosphere. The reaction mixture was concentrated and the residue was subjected to thin layer chromatography (Merck TLC plates: 20×20 cm, eluent: acetone/dichloromethane= 1:1) to give Compound 4 (86 mg) and Compound 3 (59 mg).

Example 11

(2R,3R)-2-(2,4-Difluorophenyl)-1-(1-imidazolyl)-3-(1H-tetrazol- 1-yl)-2-butanol (Compound 10) and
(2R,3R)-2-(2,4 -difluorophenyl)-1-(1-imidazolyl)-3-(2H-tetrazol-2-yl)-2-butanol (Compound 5)

Using (2R,3S)-2-(2,4-difluorophenyl)-3-methyl-2-[(1-imidazolyl)methyl] oxirane (375 mg) and tetrazole (129 mg) in the presence of bis(tri-n-butyltin)oxide (0.05 ml), Compound 5 (117 mg) and Compound 10 (86 mg) were obtained by the same way as in Example 10.

Compound 10: colorless powder mp: 172°–174° C.

$^1$H-NMR (CDCl$_3$) δ: 1.40 (3H,J=7.2Hz), 3.56 (1H,d,J=14.2Hz), 4.69 (1H,d,J=14.2Hz), 5.10 (1H,s), 5.56 (1H,q,J=7.2Hz), 6.07 (1H,s), 6.24 (1H,s), 6.85–7.06 (2H,m), 7.11 (1H,s), 7.59–7.77 (1H,m), 8.97 (1H,s).

IR $v_{max}^{KBr}$ cm$^{-1}$: 3157, 3140, 3056, 1618, 1597, 1513, 1500, 1471.

Example 12

(2R,3R)-1,3-Bis(1H-1,2,4-triazol-1-yl)-2-[2-fluoro-4-(1H-1-,2,4-triazol-1-yl)phenyl]-2-butanol (Compound 11)

1H-1,2,4-Triazole (0.3 mg) was added portionwise to a stirred dispersion of 60% sodium hydride in oil (0.16 g) in dimethylformamide (15 ml) under ice-cooling in a stream of nitrogen, followed by further stirring for 15 minutes. When the evolution of hydrogen (ceased), (2R,3R)-1,3-bis (1H-1, 2,4-triazol-1-yl)-2-(2,4-difluorophenyl)-2-butanol (0.64 g) was added to the mixture. The mixture was stirred for 3 hours at 150° C. After cooling, the reaction mixture was added into ice-water and extracted with ethyl acetate. The extract was washed with water and saturated saline and dried. The solvent was distilled off under reduced pressure. The residue was purified by silica gel column chromatography (silica gel 30 g, eluent: ethyl acetate/acetone/methanol= 5:4:1) to give the title compound (Compound 11, 92 mg) as colorless needles.

mp: 180°–182° C.

$^1$H-NMR (CDCl$_3$) δ: 1.42 (3H,d,J=7Hz), 3.76 (1H,d,J=14Hz), 4.97 (1H,d,J=14Hz), 5.25 (1H,q,J=7Hz), 5.61 (1H,s), 7.27–7.71 (3H,m), 7.74 (1H,s), 7.84 (1H,s), 8.03 (1H,s), 8.11 (1H,s), 8.45 (1H,s), 8.56 (1H,s).

Examples 13–17

The following compounds were obtained by the same way as in Example 12.

Example 13

(2R,3R)-1,3-Bis(1H-1,2,4-triazol-1-yl)-2-[2-fluoro-4-(1-imidazolyl)phenyl]-2-butanol (Compound 12)

Example 14

(2R,3R)-1,3-Bis(1H-1,2,4-triazol-1-yl)-2-[2-fluoro-4-(1-pyrazolyl)phenyl]-2-butanol (Compound 13) and (2R,3R)-1,3-bis(1H-1,2,4-triazol-1-yl)-2-[2,4-bis(1-pyrazolyl)-phenyl]-2-butanol (Compound 14)

Example 15

(2R,3R)-1,3-Bis(1H-1,2,4-triazol-1-yl)-2-[2-fluoro-4-(1-benzimidazolyl)phenyl]-2-butanol (Compound 15)

Example 16

(2R,3R)-1,3-Bis(1H-1,2,4-triazol-1-yl)-2-[2-fluoro-4-(3,5-dimethyl-1-pyrazolyl)phenyl]-2-butanol (Compound 16),
(2R,3R)-1,3-bis(1H-1,2,4-triazol-1-yl)-2-[4-fluoro-2-(3,5-dimethyl-1-pyrazolyl)phenyl]-2-butaneol (Compound 17) and (2R,3R)-1,3-bis(1H-1,2,4-triazol-1-yl)-2-[2,4-bis(3,5-dimethyl-1-pyrazolyl)phenyl]-2-butaneol (Compound 18)

Example 17

(2R,3R)-1,3-Bis(1H-1,2,4-triazol-1-yl)-2-[2-fluoro-4-(2-methyl-1-imidazolyl)phenyl]-2-butanol (Compound 19)

Table 5 shows physical constants of each compounds.

TABLE 5

| Example No. | Product |
|---|---|
| 13 | Compound 12 (0.17 g)<br>mp. 157—158° C.<br>$^1$H-NMR(CDCl$_3$)δ: 1.43(3H, d, J=Hz), 3.76(1H, d, J=14Hz), 4.96(1H, d, J=14Hz), 5.24(1H, q, J=7Hz), 5.65(1H, s), 7.09–7.28(4H, m), 7.61–7.70(1H, m), 7.74(1H, s), 7.85(1H, s), 8.03(1H, s) 8.45(1H, s) |
| 14 | Compound 13 (0.41 g)<br>mp. 178–180° C.<br>$^1$H-MNR(CDCl$_3$)δ: 1.42(3H, d, J=7Hz), 3.75(1H, d, J=14Hz), 4.96(1H, d, J=14Hz), 5.24(1H, q, J=7Hz), 5.51(1H, s), 6.49(1H, t, J=2.2Hz), 7.35–7.90(7H, m), 8.02(1H, s), 8.46(1H, s)<br>Compound 14 (0.23 g)<br>Colorless powder<br>$^1$H-MNR(CDCl$_3$)δ: 1.37(3H, d, J=7Hz), 3.45(1H, d, J=14Hz), 4.88–4.96(2H, m), 5.61(1H, s), 6.49(1H, t, J=2.2Hz), 6.66 (1H, t, J=2.2Hz), 7.57–7.97(10H, m), 8.29(1H, s) |
| 15 | Compound 15 (0.21 g)<br>mp. 108–110° C.<br>$^1$H-MNR(CDCl$_3$)δ: 1.47(3H, d, J=7.2Hz), 3.79(1H, d, J=14Hz), 5.00(1H, d, J=14Hz), 5.28(1H, q, J=7.2Hz), 5,68(1H, s), 7.25–7.41(4H, m), 7.48–7.55(1H, m), 7.71–7.91(2H, m), 7.80(1H, s), 7.89(1H, s), 8.04(1H, s), 8.10 (1H, s), 8.47(1H, s) |

TABLE 5-continued

| Example No. | Product |
|---|---|
| 16 | Compound 16 (0.33 g)<br>mp. 98–99° C.<br>$^1$H-MNR(CDCl$_3$)δ: 1.40(3H, d, J=7Hz), 2.27(2H, s), 2.32(3H, s) 3.74(1H, d, J=14Hz), 4.95(1H, d, J=14Hz), 5.24(1H, q, J=7Hz), 5.52(1H, s), 6.00(1H, s), 7.16–7.29 (2H, m), 7.57(1H, q, J=8.6Hz), 7.73(1H, s), 7.80(1H, s), 8.01 (1H, s), 8.45(1H, s)<br>Compound 17 (0.06 g)<br>Elemental Analysis for C$_{19}$H$_{21}$FN$_8$O:<br>Calcd.:   C. 57.57; H. 5.34; N. 28.27<br>Found:    C. 57.40; H. 5.40; N. 28.07<br>SIMS(m/z):   397(M + H)$^+$<br>Compound 18 (0.053 g)<br>mp. 95–96° C.<br>Elemental Analysis for C$_{24}$H$_{28}$N$_{10}$O.H$_2$O:<br>Calcd.:   C, 58.76; H, 6.16; N, 28.55<br>Found:    C, 58.82; H, 6.10; N, 28.30<br>SIMS (m/z):   473 (M + H)$^+$ |
| 17 | Compound 19 (0.1 g)<br>Colorless oil<br>$^1$H=NMR(CDCl$_3$)δ: 1.45(3H, d, J=7Hz), 2.35(3H, s), 3.81(1H, d, J=14Hz), 5.09(1H, d, J=14Hz), 5.27(1H, q, J=7Hz), 5.87(1H, s), 6.98–7.08(4H, m), 7.61–7.64(1H, m), 7.72(1H, s), 7.87(1H, s), 8.02(1H, s), 8.46(1H, s) |

Example 18

(2R,3R)-2-(2,4-Difluorophenyl)-1-(1H-1,2,4-triazol-1-yl)-3-( 4H-1,2,4-triazol-4-yl)-2-butanol (Compound 20)

A mixture of (2R,3S)-2-(2,4-difluorophenyl)-3-methyl-2-[(1H-1,2,4-triazol-1-yl)methyl]oxirane (1.40 g) and 1-trimethylsilyl-1H-1,2,4-triazole (7.8 ml) was stirred for 4 hours at 180° C. under argon atmosphere and then cooled. To the reaction mixture were added chloroform (100 ml) and water (50 ml). The separated aqueous layer was extracted with chloroform (20 ml). The combined extracts were washed with water and saturated saline and dried over magnesium sulfate. The solvent was distilled off under reduced pressure. The residue was purified by silica gel column chromatography (eluent: ethyl acetate/hexane=1:1→2:1→ ethyl acetate→ethyl acetate/methanol=20:1→10:1) to give (2R, 3R)-1,3-bis(1H-1,2,4-triazol-1-yl)-2-(2,4 -difluorophenyl)-2-trimethylsilyloxybutane (225 mg) and (2R, 3R)-2-(2,4-difluorophenyl)-1-(1H-1,2,4-triazol-1-yl)-3-(4H- 1,2,4-triazol-4-yl)-2-trimethylsilyloxybutane (750 mg).

(2R,3R)-2-(2,4-difluorophenyl)-1-(1H-1,2,4-triazol-1 -yl)-3-(4H-1,2,4-triazol-4-yl)-2-trimethylsilyloxybutane $^1$H-NMR (CDCl$_3$) δ: 0.18 (9H,s), 1.33 (3H,d,J=7.2Hz), 4.15 (1H,d,J=14.2Hz), 4.54 (1H,d,J=14.2Hz), 5.31 (1H,q,J=7.2Hz), 6.68–7.05 (2H,m), 7.26–7.50 (1H,m), 7.56 (1H,s), 7.97 (1H,s), 8.61 (2H,s).

IR $v_{max}^{neat}$cm$^{-1}$: 3105, 2960, 1620, 1600, 1590, 1500, 1420.

Tetrabutylammonium fluoride trihydrate (663 mg) was added to a solution of (2R,3R)-2-(2,4-difluorophenyl)-1-(1H-1,2,4-triazol-1-yl)-3-(4H-1,2,4-triazol-4-yl)-2-trimethylsilyloxybutane (750 mg) in tetrahydrofuran (50 ml). The mixture was stirred for 30 minutes at room temperature, and concentrated under reduced pressure. The residue was purified by silica gel chromatography (eluent: ethyl acetate/hexane=2:1→ethyl acetate→ethyl acetate/methanol= 10:1) to give Compound 20 (620 mg) as a white powder.

$^1$H-NMR (CDCl$_3$) δ: 1.37 (3H,d,J=7.0Hz), 4.09 (1H,d,J=14Hz), 4.89 (1H,d,J=14Hz), 4.97 (1H,q,J=7.0Hz), 6.70–6.91 (2H,m), 7.39–7.58 (1H,m), 7.76 (1H,s), 7.95 (1H,s), 8.46 (2H,s).

IR $v_{max}^{KBr}$cm$^{-1}$: 3390, 3110, 1610, 1500, 1460, 1420, 1370.

Elemental Analysis for C$_{14}$H$_{14}$F$_2$N$_6$O0.5H$_2$O: Calcd.: C, 51.06; H, 4.59; N, 25.52, Found: C, 51.39; H, 4.50; N, 25.68.

$[\alpha]_D^{25}$ –45.7° (c=0.42, methanol).

The compound obtained in Reference Example 6, (2R, 3R)-1,3-bis(1H-1,2,4-triazol-1-yl)-2-(2,4-difluorophenyl)-2-butanol (170 mg), was obtained as colorless needles by reaction of (2R,3R)-1,3-bis(1H-1,2,4-triazol-1-yl)-2-(2,4 -difluorophenyl)-2-trimethylsilyloxybutane (225 mg) with tetrabutylammonium fluoride trihydrate.

Example 19

(2R,3R)-2-(2,4-Difluorophenyl)-3-(2H-1,2,3-triazol-2-yl)-1-( 1H-1,2,4-triazol-1-yl)-2-butanol (Compound 8) and
(2R,3R)-2-(2,4-difluorophenyl)-3-(1H-1,2,3-triazol-1-yl)-1-( 1H-1,2,4-triazol-1-yl)-2-butanol (Compound 6)

To a stirred solution of 1H-1,2,3-triazole (2.06 g) in dimethylformamide (50 ml) was added portionwise 60% sodium hydride in oil (0.87 g) under ice-cooling. Ten minutes later, to the solution was added (2R,3S)-2-(2,4-difluorophenyl)- 3-methyl-2-[(1H-1,2,4-triazol-1-yl)methyl]oxirane (5 g), followed by stirring for 10 hours at 80° C. After cooling, the reaction mixture was poured into ice-water and extracted three times with ethyl acetate. The extract was washed with Saturated saline, dried and distilled under reduced pressure. The residue was subjected to silica gel column chromatography (silica gel 150 g, eluent: ethyl acetate+dichlormethane/acetone=1:1).

A first eluate afforded Compound 8 which was recrystallized from diisopropyl ether to give colorless crystals (1.66 g). Then a second eluate afforded Compound 6 which was recrystallized from diisopropyl ether to give colorless crystals (2.13 g).

Example 20

(2R,3R)-2-(2,4-Difluorophenyl)-3-(1H-1,2,3-triazol-1-yl)-1-( 1H-1,2,4-triazol-1-yl)-2-butanol (Compound 6)

1-[(1R,2R)-2-(2,4-Difluorophenyl)-2-hydroxy-1-methyl-3-(1H1,2,4-triazol-1-yl)propyl]-1H-1,2,3-triazol-4-carboxylic acid (Compound 33) or -5-carboxylic acid (Compound 32) was heated for 1.5 hours at 200° C. After cooling, the residue was purified by silica gel chromatography (eluent: dichloromethane/acetone=1:1), followed by recrystallization from diisopropyl ether to give Compound 6 as colorless crystals.

Examples 21–26

Substantially the same reaction as in the Example 1 was conducted to give the following compounds:

Example 21

(2R,3R)-2-(2,4-Difluorophenyl)-3-(9H-9-purinyl)-1-(1H-1,2,4-triazol-1-yl)-2-butanol (Compound 21)

Example 22

(2R,3R)-2-(2,4-Difluorophenyl)-1-(1-imidazolyl)-3-(9H-9-purinyl)-2-butanol (Compound 22)

Example 23

(2R,3R)-2-(2,4-Difluorophenyl)-3-(1H-1-imidazo[4,5-b]pyridyl)-1-(1H-1,2,4-triazol-1-yl)-2-butanol (Compound 23)

Example 24

(2R,3R)-2-(2,4-Difluorophenyl)-1-(1-imidazolyl)-3-(1H-1-imidazo[4,5-b]pyridyl)-2-butanol (Compound 24)

Example 25

(2R,3R)-2-(2,4-Difluorophenyl)-1-(3H-3-imidazo[4,5-b]pyridyl)-1-(1H-1,2,4-triazol-1-yl)-2-butanol (Compound 26)

Example 26

(2R,3R)-2-(2,4-Difluorophenyl)-1-(1-imidazolyl)-3-(3H-3-imidazo[4,5-b]pyridyl)-2-butanol (Compound 29)

Table 6 shows physical constants of the above compounds.

The numerical values in parentheses next to a compound No. each mean "an yield and its percentage (actually obtained of the amount theoretically)" of every compound.

TABLE 6

| Example No. | Product |
|---|---|
| 21 | Compound 21 (198 mg. 51%)<br>mp. 179–180° C.<br>$^1$H-NMR(CDCl$_3$)δ: 1.43(3H, d, J=7.2Hz), 3.60(1H, d, J=14.2Hz)5.00(1H, d, J=14.2Hz), 5.63(1H, q, J=7.2Hz), 5.65(1H, s), 6.78–6.96(2H, m), 7.45–7.60(1H, m), 7.73(1H, s), 7.76(1H, s), 8.59(1H, s), 9.08(1H, s), 9.22(1H, s)<br>Elemental Analysis for C$_{17}$H$_{15}$F$_2$N$_7$O:<br>Calcd.: C, 54.99; H, 4.07; N, 26.40<br>Found: C, 54.63; H, 4.05; N, 26.09 |
| 22 | Compound 22 (244 mg, 70%)<br>mp. 136–137° C.<br>$^1$H-NMR(CDCl$_3$)δ: 1.40(3H, d, J=7.0Hz), 3.50(1H, d, J=14.4Hz), 4.67(1H, d, J=14.4Hz), 5.51(1H, q, J=7.0Hz), 6.26 (1H, s), 6.40(1H, s), 6.85–7.04(2H, m), 7.07(1H, s), 7.62–7.80(1H, m), 8.44(1H, s), 9.06(1H, s), 9.21(1H, s)<br>Elemental Analysis for C$_{18}$H$_{16}$F$_2$N$_6$O:<br>Calcd.: C, 58.37; H, 4.35; N, 22.69<br>Found: C, 58.58; H, 4.14; N, 22.58 |
| 23 | Compound 23 (250 mg, 81%)<br>Colorless oil<br>$^1$H-NMR(CDCl$_3$)δ: 1.41(3H, d, J=7.0Hz), 3.73(1H, d, J=14.8Hz), 4.96(1H, d, J=14.8Hz), 5.59(1H, q, J=7.0Hz), 6.78–6.94(2H, m)7.33(1H, dd, J=8.0, 4.8Hz), 7.51–7.70(1H, m), 7.66(1H, s), 7.79(1H, s), 8.16(1H, dd, J=8.0, 1.4Hz), 8.46(1H, s), 8.47(1H, dd, J=4.8, 1.4Hz)<br>SIMS (m/z): 371(M + H)$^+$ |

TABLE 6-continued

| Example No. | Product |
|---|---|
| 24 | Compound 24 (230 mg, 78%)<br>mp. 115–116° C.<br>$^1$H-NMR(CDCl$_3$)δ: 1.40(3H, d, J=7.0Hz), 3.69(1H, d, J=14.8Hz), 4.54(1H, dd, J=14.8, 2.2Hz), 5.30(1H, q, J=7.0Hz), 6.63(1H, s), 6.68(1H, s), 6.79–6.94(2H, m), 7.19(1H, s), 7.39(1H, dd, J=8.2, 5.0Hz), 7.61–7.80(1H, m), 8.22(1H, dd, J=8.2, 1.4Hz), 8.22(1H, s), 8.46(1H, dd, J=5.0, 1.4Hz)<br>Elemental Analysis for C$_{19}$H$_{17}$F$_2$N$_5$O:<br>Calcd.: C, 61.78; H, 4.64; N, 18.96<br>Found: C, 61.53; H, 4.32; N, 19.01 |
| 25 | Compound 26 (140 mg, 74%)<br>pale yellow foam<br>$^1$H-NMR(CDCl$_3$)δ: 1.49(3H, d, J=7.0Hz), 4.50(1H, d, J=14.8Hz), 4.98(1H, d, J=14.8Hz), 5.21(1H, q, J=7.0Hz), 6.78–7.00(2H, m), 7.21(1H, dd, J=8.2, 4.8Hz), 7.43–7.60(1H, m), 7.65(1H, s), 7.88(1H, s), 8.03–8.30(2H, m), 8.47(1H, s)<br>SIMS (m/z): 371 (M + H)$^+$ |
| 26 | Compound 29 (83 mg, 55%)<br>mp. 149–150° C.<br>$^1$H-NMR(CDCl$_3$)δ: 1.46(3H, d, J=7.0Hz); 4.67(1H, d, J=14.0Hz), 4.83(1H, d, J=14.0Hz), 5.26(1H, q, J=7.0Hz), 6.58(2H, s), 6.81–7.02(2H, m), 7.25(1H, dd, J=8.2, 5.0Hz), 7.37(1H, s), 7.60–7.72(1H, m), 7.84(1H, dd, J=8.2, 1.4Hz), 8.09(1H, dd, J=5.0, 1.4Hz), 8.38(1H, s)<br>Elemental Analysis for C$_{19}$H$_{17}$F$_2$N$_5$O:<br>Calcd.: C, 61.78; H, 4.64; N, 18.96<br>Found: C, 61.62; H, 4.98; N, 18.84 |

Example 27

Ethyl 1-[(1R,2R)-2-(2,4-difluorophenyl)-2-hydroxy-1-methyl-3-(1H-1,2,4-triazol-1-yl)propyl]-1H-1,2,3-triazole-5-carboxylate (Compound 30) and ethyl 1-[(1R,2R)-2-(2,4-difluorophenyl)-2-hydroxy-1-methyl-3-(1H-1,2,4-triazol-1-yl)propyl]-1H-1,2,3-triazole-4-carboxylate (Compound 31)

A mixture of toluene (100 ml), ethyl propiolate (2 ml) and (2R,3R)-3-azido-2-(2,4-difluorophenyl)-1-(1H-1,2,4-triazol-1-yl)-2-butanol (4.2 g) was heated for 3 hours at 120° C. After cooling, toluene was distilled off under reduced pressure. The residue was purified by silica gel chromatography (silica gel 200 g, eluent: dichloromethane/acetone= 4:1→ 2:1) to give two kinds of isomers (Isomer A and Isomer B).

Isomer B (less polar substance: Compound 30 or 31, Yield: 2.95 g)

$^1$H-NMR(CDCl$_3$) δ: 1.37–1.49 (6H,m), 3.54 (1H, d, J=14Hz), 4.47 (2H,q,J=7Hz), 5.01 (1H,d,J=14Hz), 5.48 (1H, s), 5.56 (1H,q,J=7Hz), 6.79–6.90 (2H,m), 7.41–7.54 (1H,m), 7.76 (1H,s), 7.77 (1H,s), 8.52 (1H,s).

mp: 80°–82° C.

Isomer A (more polar substance: Compound 30 or 31, Yield: 2.11 g)

$^1$H-NMR(CDCl$_3$) δ: 1.43 (3H,t,J=7Hz), 1.53 (3H,d,J=7Hz), 3.85 (1H,d,J=14Hz), 4.44 (2H,q,J=7Hz), 4.96 (1H,d, J=14Hz), 5.31 (1H,s), 6.37 (1H,q,J=7Hz), 6.75–6.89 (2H, m), 7.52–7.61 (1H,s), 7.65 (1H,s), 7.92 (1H,s), 8.22 (1H,s).

mp: 125°–126° C.

Example 28

1-[(1R,2R)-2-(2,4-Difluorophenyl)-2-hydroxy-1-methyl-3-(1H-1,2,4-triazol-1-yl)propyl]-1H-1,2,3-triazole-5-carboxylic acid (Compound 32) and 1-[(1R,2R)-2-(2,4-difluorophenyl)-2-hydroxy-1-methyl-3-(1H-1,2,4-triazol-1-yl)propyl]-1H-1,2,3-triazole-4-carboxylic acid (Compound 33)

In methanol (5 ml) was dissolved the isomer B (less polar, 500 mg) obtained in Example 27. To the solution was added 1N sodium hydroxide aqueous solution (1.9 ml). The mixture was stirred for 30 minutes at room temperature, neutralized with 1N hydrochloric acid (1.9 ml). Methanol was distilled off under reduced pressure. Water (30 ml) was added to the residual mixture. The mixture was extracted with a mixture of ethyl acetate and tetrahydrofuran (1:1, 50 ml×2). The extract was dried over anhydrous sodium sulfate, and distilled off under reduced pressure. Diethyl ether (30 ml) was added to the residue. The precipitate was collected by filtration to give Compound 32 or 33 (320 mg) as a colorless powder.

$^1$H-NMR(DMSO-d6) δ: 1.44 (3H,d,J=7Hz), 3.99 (1H,d,J=14Hz), 4.87 (1H,d,J=14Hz), 6.17 (1H,q,J=7Hz), 6.84–6.95 (1H,m), 7.02–7.38 (2H,m), 7.60 (1H,s), 7.99 (1H,s), 8.25 (1H,s).

The Isomer A (more polar, 500 mg) prepared in Example 27 was hydrolyzed under the same condition as stated above to give Compound 32 or 33 (387 mg) as colorless powders.

$^1$H-NMR(DMSO-d6) δ: 1.34 (3H,d,J=7Hz), 3.96 (1H,d,J=14Hz), 4.85 (1H,d,J=14Hz), 5.45 (1H,q,J=7Hz), 6.22 (1H,bs), 6.91–7.01 (1H,m), 7.21–7.33 (2H,m), 7.63 (1H,s), 8.22 (1H,s), 8.72 (1H,s).

Example 29

(2R,3R)-2-(4-Chlorophenyl)-3-(2H-1,2,3-triazol-2-yl)-1-(1H-1,2,4-triazol-1-yl)-2-butanol (Compound 34) and (2R,3R)-2-(4-chlorophenyl)-3-(1H-1,2,3-triazol-1-yl)-1-(1H-1,2,4-triazol-1-yl)-2-butanol (Compound 35)

To a stirred solution of 1H-1,2,3-triazole (2.07 g) in dimethylformamide (50 ml) was added portionwise 60% sodium hydride in oil (0.96 g) under ice-cooling. Ten minutes later, to the mixture was added (2R,3S)-2-(4-chlorophenyl)- 3-methyl-2-[(1H-1,2,4-triazol-1-yl)methyl]oxirane (5.0 g), followed by stirring for 15 hours at 80° C. After cooling, the mixture was concentrated. The residue was partitioned with ethyl acetate (200 ml) and saline. The organic layer was washed with saturated saline and dried. The solvent was distilled off under reduced pressure. The residue was purified by silica gel column chromatography (silica gel 200 g, eluent: ethyl acetate/dichlormethane=4:1→ dichloromethane/acetone=1:1). The first eluate gave Compound 34 (2.05 g), which was recrystallized from dichloromethane-diisopropyl ether to give colorless needles (1.79 g), and a second eluate gave Compound 35 (1.6 g) which was recrystallized from acetone-diisopropyl ether to give colorless prisms.

Compound 34

$^1$H-NMR (CDCl$_3$) δ: 1.43 (3H,d,J=7Hz), 3.73 (1H,d,J=14.4Hz), 4.55 (1H,d,J=14.4Hz), 5.22 (1H,s), 5.26 (1H,q,J=7Hz), 7.27 (4H,m), 7.71 (1H,s), 7.74 (2H,s), 7.75 (1H,s).

mp: 148°–149° C.

$[α]_D^{20}$ –120° (c=0.5, MeOH).

Compound 35

$^1$H-NMR(CDCl$_3$) δ: 1.40 (3H,d,J=7Hz), 3.58 (1H,d,J=14.4Hz), 4.60 (1H,d,J=14.4Hz), 5.28 (1H,q,J=7Hz), 5.31 (1H,s), 7.28 (4H,m), 7.64 (1H,s), 7.78 (1H,s), 7.79 (1H,d,J=1Hz), 7.97 (1H,d,J=1Hz).

mp: 145°–147° C.

$[α]_D^{20}$ –90.8° (c=0.48, MeOH).

Example 30

(2R,3R)-2-(4-Fluorophenyl)-3-(2H-1,2,3-triazol-2-yl)-1-(1H-1,2,4-triazol-1-yl)-2-butanol (Compound 36) and (2R,3R)-2-(4-fluorophenyl)-3-(1H-1,2,3-triazol-1-yl)-1-(1H-1,2,4-triazol-1-yl)-2-butanol (Compound 37)

To a strred solution of 1H-1,2,3-triazole (1.49 g) in dimethylformamide (35 ml) was added portionwise 60% sodium hydride in oil (0.63 g) under ice-cooling. Ten minutes later, to the mixture was added (2R,3S)-2-(4-fluorophenyl)- 3-methyl-2-[(1H-1,2,4-triazol-1-yl)methyl]oxirane (3.34 g), followed by stirring for 4 hours at 80° C. After cooling, the mixture was concentrated. The residue was partitioned with ethyl acetate (300 ml) and saturated saline. The organic layer was washed with saturated saline, dried and distilled under reduced pressure. The residue was purified by silica gel column chromatography (silica gel 150 g, eluent: dichloro methane/acetone=3:2→1:1). The first eluate gave Compound 36 (1.02 g), followed by recrystallization from dichloromethane-diisopropyl ether to afford colorless prisms. Then a second eluate gave Compound 37 (1.05 g), followed by recrystallization from dichloromethane-diisopropyl ether to afford a colorless crystalline powder.

Compound 36 mp: 125°–127° C.

$^1$H-NMR(CDCl$_3$) δ: 1.43 (3H,d,J=7Hz), 3.73 (1H,d,J=14Hz), 4.55 (1H,d,J=14Hz), 5.21 (1H,s), 5.26 (1H,q,J=7Hz), 6.96–7.04 (2H,m), 7.29–7.34 (2H,m), 7.71 (1H,s), 7.75 (3H,s).

$[α]_D^{20}$ –90.4° (c=1, MeOH).

Compound 37

$^1$H-NMR(CDCl$_3$) δ: 1.40 (3H,d,J=7Hz), 3.58 (1H,d,J=14Hz), 4.62 (1H,d,J=14Hz), 5.25–5.39 (1H,m), 5.30 (1H,s), 6.96–7.05 (2H,m), 7.29–7.36 (2H,m), 7.66 (1H,s), 7.78 (1H,s), 7.80 (1H,s), 7.98 (1H,s).

Example 31

(2R,3R)-3-(2H-1,2,3-Triazol-2-yl)-1-(1H-1,2,4-triazol-1-yl)- 2-(4-trifluoromethylphenyl)-2-butanol (Compound 38) and (2R,3R)-3-(1H-1,2,3-triazol-1-yl)-1-(1H-1,2,4-triazol-1-yl) -2-(4-trifluoromethylphenyl)-2-butanol (Compound 39)

Using 1H-1,2,3-triazole and (2R,3S)-3-methyl-2-[1H-1,2,4-triazol-1-yl)methyl]-2-(4-trifluoromethylphenyl) oxirane, substantially the same reaction as in Example 30 was conducted to give Compound 38 (1.2 g, 24%) as colorless needles and Compound 39 (1.6 g, 32%) as a colorless powder.

Compound 38

$^1$H-NMR (CDCl$_3$) δ: 1.42 (3H,d,J=7.0Hz), 3.77 (1H,d,J=14Hz), 4.61 (1H,d,J=14Hz), 5.31 (1H,q,J=7.0Hz), 5.35 (1H, s), 7.46 (2H, d, J=8.4Hz), 7.57 (2H,d,J=8.4Hz), 7.69 (1H,s), 7.75 (2H,s), 7.78 (1H,s).

mp: 118°–119° C.

Elemental Analysis for C$_{15}$H$_{15}$F$_3$N$_6$O: Calcd.: C, 51.14; H, 4.29; N, 23.85, Found: C, 51.08; H, 4.25; N, 23.64.

[α]$_D^{20}$ −88.0° (c=1.0, MeOH).

Compound 39

$^1$H-NMR (CDCl$_3$) δ: 1.40 (3H,d,J=7.0Hz), 3.62 (1H,d,J=14Hz), 4.70 (1H,d,J=14Hz), 5.36 (1H,q,J=7.0Hz), 5.49 (1H, s), 7.51 (2H,d,J=8.6Hz), 7.60 (2H, d,J=8.6Hz), 7.68 (1H,s), 7.79 (2H,s), 7.82 (1H,s), 8.00 (1H,s).

mp: 106°–107° C.

Elemental Analysis for C$_{15}$H$_{15}$F$_3$N$_6$O: Calcd.: C, 51.14; H, 4.29; N, 23.85, Found: C, 51.04; H, 4.40; N, 23.45.

[α]$_D^{20}$ −65.7° (c=1.1, MeOH).

Example 32

(2R,3R)-3-(2H-1,2,3-Triazol-2-yl)-1-(1H-1,2,4-triazol-1-yl)-2-(4-trifluoromethoxylphenyl)-2-butanol (Compound 40) and
(2R,3R)-3-(1H-1,2,3-triazol-1-yl)-1-(1H-1,2,4-triazol-1-yl)-2-(4-trifluoromethylphenyl)-2-butanol (Compound 41)

Using 1H-1,2,3-triazole and (2R,3S)-3-methyl-2-[(1H-1,2,4-triazol-1-yl)methyl]-2-(4-trifluoromethoxyl phenyl)oxirane, substantially the same reaction as in Example 30 was conducted to give Compound 40 as colorless prisms and Compound 41 as colorless needles.

Compound 40

$^1$H-NMR (CDCl$_3$) δ: 1.43 (3H,d,J=7Hz), 3.75 (1H,d,J=14.2Hz), 4.57 (1H,d,J=14.2Hz), 5.29 (1H,q,J=7Hz), 5.30 (1H,s), 7.16 (2H,d,J=9Hz), 7.37 (2H,d,J=9Hz), 7.71 (1H,s), 7.76 (2H,s), 7.78 (1H,s).

IR ν$_{max}^{KBr}$ cm$^{-1}$: 3250, 1598 1510, 1466, 1417, 1353, 1277, 1257, 1213.

Elemental Analysis for C$_{15}$H$_{15}$F$_3$N$_6$O$_2$: Calcd.: C, 48.92; H, 4.10; N, 22.82, Found: C, 49.27; H, 4.19; N, 22.87.

mp: 126°–127° C.

[α]$_D^{20}$ −84.8° (c=0.5, MeOH).

Compound 41

$^1$H-NMR (CDCl$_3$) δ: 1.40 (3H,d,J=7Hz), 3.60 (1H,d,J=14.2Hz), 4.63 (1H,d,J=14.2Hz), 5.32 (1H,q,J=7Hz), 5.40 (1H,s), 7.17 (2H,d,J=9Hz), 7.40 (2H,d,J=9Hz), 7.66 (1H,s), 7.80 (1H,s), 7.81 (1H,s), 7.99 (1H,s).

IR ν$_{max}^{KBr}$ cm$^{-1}$: 3450, 1598, 1512, 1416, 1280, 1222, 1147.

Elemental Analysis for C$_{15}$H$_{15}$F$_3$N$_6$O$_2$: Calcd.: C, 48.92; H, 4.10; N, 22.82, Found: C, 49.10; H, 4.14; N, 22.75.

mp: 119°–121° C.

[α]$_D^{20}$ −64.1° (c=0.5, MeOH).

Example 33

(2R,3R)-2-(2-Chlorophenyl)-3-(2H-1,2,3-triazol-2-yl)-1-(1H- 1,2,4-triazol-1-yl)-2-butanol (Compound 42) and
(2R,3R)-2-(2-chlorophenyl)-3-(1H-1,2,3-triazol-1-yl)-1-( 1H-1,2,4-triazol-1-yl)-2-butanol (Compound 43)

Using 1H-1,2,3-triazole and (2R,3S)-2-(2-chlorophenyl)-3-methyl-2-[(1H-1,2,4-triazol-1-yl)methyl]oxirane, Compound 42 and Compound 43 were obtained by the same way as in Example 30.

Compound 42

$^1$H-NMR (CDCl$_3$) δ: 1.40 (3H,d,J=7Hz), 3.51 (1H,d,J=14Hz), 5.26 (1H,s), 5.53 (1H,d,J=14Hz), 6.13 (1H,q,J=7Hz), 7.18–7.39 (3H,m), 7.39 (1H,s), 7.64–7.76 (1H,m), 7.77 (2H,s), 7.80 (1H,s).

Compound 42 hydrochloride (colorless crystalline powder)

$^1$H-NMR (CDCl$_3$) δ: 1.30 (3H,d,J=7Hz), 3.83 (1H,d,J=14Hz), 5.44 (1H,d,J=7Hz), 6.01 (1H,q,J=7Hz), 7.16–7.52 (4H,m), 7.76 (1H,s), 7.96 (2H,s), 8.50 (1H,s).

Compound 43 (colorless crystals)

$^1$H-NMR (CDCl$_3$) δ: 1.34 (3H,d,J=7Hz), 3.42 (1H,d,J=14Hz), 5.36 (1H,s), 5.66 (1H,d,J=14Hz), 6.13 (1H, q, J=7Hz), 7.16–7.39 (3H,m), 7.65–7.74 (1H,m), 7.71 (1H,s), 7.79 (1H,s), 7.82 (1H,s), 8.02 (1H,s).

Example 34

(2R,3R)-2-(2-Fluorophenyl)-3-(2H-1,2,3-triazol-2-yl)-1-(1H-1,2,4-triazol-1-yl)-2-butanol (Compound 44) and (2R,3R)-2-(2-fluorophenyl)-3-(1H-1,2,3-triazol-1-yl)-1-(1H-1,2,4-triazol-1-yl)-2-butanol (Compound 45)

Using 1H-1,2,3-triazole and (2R,3S)-2-(2-fluorophenyl)-3-methyl-2-[(1H-1,2,4-triazol-1-yl)methyl]oxirane, Compound 44 and Compound 45 were obtained by the same way as in Example 30.

Compound 44

$^1$H-NMR (CDCl$_3$) δ: 1.43 (3H,d,J=7Hz), 3.60 (1H,d,J=14Hz), 4.96 (1H,d,J=14Hz), 5.20 (1H,s), 5.59 (1H,q,J=7Hz), 7.00–7.11 (2H,m), 7.23–7.58 (2H,m), 7.64 (1H,s), 7.75 (2H,s), 7.78 (1H,s).

Compound 44.hydrochloride (colorless powder)

mp: 164°–166° C.

$^1$H-NMR (d$_6$-DMSO) δ: 1.36 (3H,d,J=7Hz), 3.90 (1H,d, J=14Hz), 4.93 (1H,d,J=14Hz), 5.41 (1H,q,J=7Hz), 7.01–7.32 (4H,m), 7.74 (1H,s), 7.92 (2H,s), 8.46 (1H,s).

[α]$_D^{20}$ −83.9° (c=0.5, MeOH).

Compound 45 (colorless powder)

$^1$H-NMR (CDCl$_3$) δ: 1.38 (3H,d,J=7Hz), 3.49 (1H,d,J=14Hz), 5.03 (1H,d,J=14Hz), 5.28 (1H,s), 5.58 (1H,q,J=7Hz), 6.99–7.12 (2H,m), 7.21–7.51 (2H,m), 7.72 (2H,s), 7.80 (1H,s), 8.00 (1H,s).

Example 35

(2R,3R)-2-(2,4-Difluorophenyl)-3-[6-methoxy-7(7H)-purinyl-[ -1-(1H-1,2,4-triazol-1-yl)-2-butanol (Compound 46)

Using 1H-1,2,4-triazole (84 mg) and (2S)-2-(2,4 -difluorophenyl)-2-[(1R)-1-[6-methoxy-7(7H)-purinyl] ethyl]oxirane (205 mg), Compound 46 (213 mg) was obtained as colorless prisms by the same way as in Example 1.

mp: 116°–118° C.

$^1$H-NMR (CDCl$_3$) δ: 1.40 (3H,d,J=7Hz), 3.64 (1H,d,J=14Hz), 4.22 (3H,s), 4.97 (1H,d,J=14Hz), 5.53 (1H,q,J=7Hz), 5.79 (1H,s), 6.75–6.94 (2H,m), 7.45–7.61 (1H,m), 7.70 (1H,s), 7.77 (1H,s), 8.36 (1H,s), 8.62 (1H,s).

IR $v_{max}^{KBr}$ cm$^{-1}$: 3224, 3133, 1601, 1579, 1500, 1477.

Elemental Analysis for C$_{18}$H$_{17}$F$_2$N$_7$O$_2$: Calcd.: C, 53.86; H, 4.27; N, 24.43, Found: C, 54.17; H, 4.52; N, 24.79.

Example 36

(2R,3R)-2-(2,4-Difluorophenyl)-3-[6-methoxy-9(9H)-purinyl] -1-(1H-1,2,4-triazol-1-yl)-2-butanol (Compound 47)

Using 1H-1,2,4-triazole (74 mg) and (2S)-2-(2,4 -difluorophenyl)-2-[(1R)-1-[6-methoxy-9(9H)-purinyl]ethyl] oxirane (183 mg), Compound 47 (171 mg) was obtained as colorless prisms by the same way as in Example 1.

mp: 124°–125° C.

$^1$H-NMR (CDCl$_3$) δ: 1.43 (3H,d,J=7.2Hz), 3.95 (1H,d,J=14Hz), 4.31 (3H,s), 5.04 (1H,d,J=14Hz), 5.74 (1H,q,J=7.2Hz), 5.83 (1H,s), 6.75–6.92 (2H,m), 7.40–7.54 (1H,m), 7.71 (1H,s), 7.87 (1H,s), 8.54 (1H,s), 8.59 (1H,s).

IR $v_{max}^{KBr}$ cm$^{-1}$: 3126, 3082, 1610, 1564, 1500, 1479.

Elemental Analysis for C$_{18}$H$_{17}$F$_2$N$_7$O$_2$: Calcd.: C, 53.86; H, 4.27; N, 24.43, Found: C, 54.09; H, 4.44; N, 24.19.

Example 37

(2R,3R)-2-(2,4-Difluorophenyl)-3-[6-methyl-9(9H)-purinyl] -1-(1H-1,2,4-triazol-1-yl)-2-butanol (Compound 48)

Using 1H-1,2,4-triazole (167 mg) and (2S)-2-(2,4 -difluorophenyl)-2-[(1R)-1-[6-methyl-9(9H)-purinyl]ethyl] oxirane (388 mg), Compound 48 (79 mg) was obtained as colorless prisms by the same way as in Exmaple 1.

mp: 200°–201° C.

$^1$H-NMR (CDCl$_3$) δ: 1.41 (3H,d,J=7.4Hz), 2.91 (3H,s), 3.60 (1H,d,J=14.2Hz), 4.98 (1H,d,J=14.2Hz), 5.57 (1H,q,J=7.4Hz), 6.75–6.96 (2H,m), 7.45–7.62 (1H,m), 7.71 (1H,s), 7.75 (1H,s), 8.48 (1H,s), 8.93 (1H,s).

IR $v_{max}^{KBr}$ cm$^{-1}$: 3105, 3045, 1614, 1603, 1581, 1500.

Elemental Analysis for C$_{18}$H$_{17}$F$_2$N$_7$O: Calcd.: C, 56.10; H, 4.45; N, 25.44, Found: C, 55.86; H, 4.18; N, 25.64.

Example 38

(2R,3R) -2-(2,4-Difluorophenyl)-1-(1H-1,2,4-triazol-1-yl)-3 -[6-(1H-1,2,4-triazol-1-yl)-9 (9H)-purinyl]-2-butanol (Compound 49)

Using 1H-1,2,4-triazole (167 mg) and (2S)-2-[(1R)-1-[ 6-chloro-9(9H)-purinyl]ethyl]-2-(2,4-difluorophenyl) oxirane (430 mg), Compound 49 (399 mg) was obatined as a white powder by the same way as in Example 1.

$^1$H-NMR (CDCl$_3$) δ: 1.46 (3H,d,J=7.2Hz), 3.61 (1H,d,J=14.2Hz), 5.01 (1H,d,J=14.2Hz), 5.67 (1H,s), 5.69 (1H,q,J=7.2Hz), 6.77–6.95 (2H,m), 7.42–7.60 (1H,m), 7.73 (1H,s), 7.75 (1H,s), 8.33 (1H,s), 8.69 (1H,s), 8.98 (1H,s), 9.74 (1H,s).

IR $v_{max}^{KBr}$ cm$^{-1}$: 3122, 2998, 1603, 1578, 1500, 1466.

SIMS (m/z): 439 (M+H)$^+$

Example 39

(2R, 3R )-3-[2,6-Bis(1H-1,2,4-triazol-1-yl)-9 (9H)-purinyl] -2-(2,4-difluorophenyl)-1-(1H-1,2,4-triazol-1-yl)- 2-butanol (Compound 50)

Using 1H-1,2,4-triazole (59 mg) and (2S)-2-[(1R)-1-[2,6-dichloro-9 (9H)-purinyl]ethyl]-2-(2,4-difluorophenyl) oxirane (168 mg), Compound 50 (21 mg) was obtained as a white powder by the same way as in Example 1.

$^1$H-NMR (CDCl$_3$) δ: 1.49 (3H,d,J=7.2Hz), 3.67 (1H,d,J=13.8Hz), 5.01 (1H,d,J=13.8Hz), 5.69 (1H,q,J=7.2Hz), 5.75 (1H,s), 6.78–6.98 (2H,m), 7.42–7.65 (1H,m), 7.74 (1H,s), 7.76 (1H,s), 8.29 (1H,s), 8.39 (1H,s), 8.76 (1H,s), 9.40 (1H,s), 9.75 (1H,s).

IR $v_{max}^{KBr\ cm-1}$: 3105, 2998, 1602, 1582, 1500, 1467.

SIMS (m/z): 506 (M+H)$^+$

Example 40

(2R,3R)-2-(4-Chlorophenyl)-3-(2H-tetrazol-2-yl)-1-(1H-1,2,4 -triazol-1-yl)-2-butanol (Compound 51) and (2R, 3R)-2-(4-chlorophenyl)-3-(1H-tetrazol-1-yl)-1-(1H-1,2,4 -triazol-1-yl)-2-butanol (Compound 52)

A mixture of (2R,3S)-2-(4-chlorophenyl)-3-methyl-2-[ (1H-1,2,4-triazol-1-yl)methyl]oxirane (3 g), tetrazole (1.68 g), lithium carbonate (8.8 g) and dimethylformamide (56 ml) was stirred for 8 hours at 110° C. After cooling, ethyl acetate (100 ml) was added to the mixture. The mixture was filtered to remove insoluble substances. The filtrate was distilled under reduced pressure. The residue was dissolved in ethyl acetate (200 ml) and the solution was washed with saturated saline (100 ml×2). The ethyl acetate layer was dried over anhydrous magnesium sulfate and distilled under reduced pressure. The residue was purified by silica gel chromatography (silica gel 300 g, eluent: dichloromethane/acetone= 3:1→2:1) to give Compound 51 (1.81 g) from the first eluate and Compound 52 (0.8 g) from a second eluate.

Compound 51 (colorless powder recrystallized from diisopropyl ether)

mp: 118°–120° C.

$^1$H-NMR(CDCl$_3$) δ: 1.59 (3H,d,J=7Hz), 3.96 (1H,d,J=14Hz), 4.73 (1H,d,J=14Hz), 5.13 (1H,s), 5.47 (1H,q,J=7Hz), 7.21–7.32 (4H,m), 7.74 (2H,s), 8.60 (1H,s).

$[α]_D^{20}$ −73.1° (c=0.5, MeOH).

Compoun 52 (colorless oily)

$^1$H-NMR(CDCl$_3$) δ: 1.43 (3H,d,J=7Hz), 3.64 (1H,d,J=14Hz), 4.64 (1H,d,J=14Hz), 5.33 (1H,q,J=7Hz), 5.50 (1H,s), 7.24–7.34 (4H,m), 7.66 (1H,s), 7.79 (1H,s), 8.99 (1H,s).

The above oily substance was dissolved in ethyl acetate, followed by addition of 4N hydrochloric acid-ethyl acetate solution. The precipitated colorless powder was collected by filtration, and dried under reduced pressure to give the hydrochoride of Compound 52.

mp: 174°–176° C.

¹H-NMR(d₆-DMSO) δ: 1.46 (3H,d,J=7Hz), 4.43 (1H,d, J=14Hz), 4.86 (1H,d,J=14Hz), 5.31 (1H,q,J=7Hz), 7.21–7.46 (4H,m), 7.99 (1H,s), 8.51 (1H,s), 9.32 (1H,s).
[α]$_D^{20}$ −50.6° (c=0.5, MeOH).

Example 41

(2R,3R)-2-(4-Fluorophenyl)-3-(2H-tetrazol-2-yl)-1-(1H-1,2,4-triazol-1-yl)-2-butanol (Compound 53)
and
(2R,3R)-2-(4-fluorophenyl)-3-(1H-tetrazol-1-yl)-1-(1H-1,2,4-triazol-1-yl)-2-butanol (Compound 54)

Using tetrazole (2.46 g) and (2R,3S)-2-(4-fluoro phenyl)-3-methyl-2-[(1H-1,2,4-triazol-1-yl)methyl]oxirane (4.1 g), substantially the same reaction as in Example 40 was conducted to give Compound 53 (2.35 g) and Compound 54 (1.05 g) each as a white powder.
compound 53 (recrystallized from diisopropyl ether)
mp: 98°–99° C.
¹H-NMR (CDCl₃) δ: 1.59 (3H,d,J=7Hz), 3.96 (1H,d,J=14Hz), 4.73 (1H,d,J=14Hz), 5.10 (1H,s), 5.51 (1H,q,J=7Hz), 6.96–7.04 (2H,m), 7.26–7.32 (2H,m), 7.73 (1H,s), 7.74 (1H,s), 8.60 (1H,s).
[α]$_D^{20}$ −51.6° (c=0.5, MeOH).
Compound 54 (recrystallized from diisopropyl ether)
mp: 143°–144° C.
¹H-NMR (CDCl₃) δ: 1.43 (3H,d,J=7Hz), 3.64 (1H,d,J=14Hz), 4.62 (1H,d,J=14Hz), 5.32 (1H,q,J=7Hz), 5.47 (1H,s), 6.98–7.09 (2H,m), 7.25–7.37 (2H,m), 7.64 (1H,s), 7.80 (1H,s), 9.00 (1H,s).
[α]$_D^{20}$ −33.2° (c=0.5, MeOH).

Example 42

(2R,3R)-2-(2,4-Difluorophenyl)-3-(5-hydroxymethyl-1H-1,2,3-triazol-1-yl)-1-(1H-1,2,4-triazol-1-yl)-2-butanol (Compound 55) and
(2R,3R)-2-(2,4-difluorophenyl)-3-(4-hydroxymethyl-1H-1,2,3-triazol-1-yl)-1-(1H-1,2,4-triazol-1-yl)-2-butanol (Compound 56)

A mixture of toluene (150 ml), 2-propynyl alcohol (5.2 ml) and (2R,3R)-3-azido-2-(2,4-difluorophenyl)-1-(1H-1,2,4-triazol-1-yl)-2-butanol (3.5 g) was heated for 20 hours at 130° C. After cooling, toluene was distilled off under reduced pressure. The residue was purified by silica gel chromatography (silica gel 100 g, eluent: ethyl acetate/acetone=3:1→2:1) to give two isomers (Compound 55 and Compound 56).
Compound 55 (less polar substance, Yield: 2.95 g, colorless powder)
¹H-NMR(CDCl₃) δ: 1.44 (3H,d,J=7Hz), 3.83 (1H, t, J=6Hz), 3.92 (1H,d,J=14Hz), 4.77–4.87 (3H,m), 5.61 (1H, q, J=7Hz), 5.91 (1H,s), 6.75–6.91 (2H,m), 7.59–7.67 (1H, m), 7.65 (1H,s), 7.70 (1H,s), 7.91 (1H,s).
mp: 107°–108° C. (recrystallized from diisopropyl ether).
Compound 56 (more polar substance, Yield: 1.6 g, colorless powder)
¹H-NMR(CDCl₃) δ: 1.36 (3H,d,J=7Hz), 2.74 (1H,t,J=6Hz), 3.59 (1H,d,J=14Hz), 4.85 (2H,d,J=6Hz), 4.97 (1H,d, J=14Hz), 5.41 (1H,s), 5.46 (1H,q,J=7Hz), 6.78–6.88 (2H, m), 7.42–7.55 (1H,m), 7.75 (1H,s), 7.77 (1H,s), 7.95 (1H,s).
mp: 82°–83° C. (recrystallized from diisopropyl ether).

Example 43

(2R,3R)-2-(2,4-Difluorophenyl)-1-(1H-1,2,4-triazol-1-yl)-3-[4-(1H-1,2,4-triazol-1-yl)methyl-1H-1,2,3-triazol-1-yl]-2-butanol (Compound 57)

Triethylamine (0.26 ml) was added dropwise to a solution of (2R,3R)-2-(2,4-difluorophenyl)-3-(4-hydroxy methyl-1H-1,2,3-triazol-1-yl)-1-(1H-1,2,4-triazol-1-yl)- 2-butanol (Compound 56, 0.6 g) and methanesulfonyl chloride (0.14 ml) in dichloromethane (20 ml) under ice-cooling. The mixture was stirred for 30 minutes at room temperature. After addition of dichloromethane (20 ml), the mixture was washed with water (20 ml) and 5% sodium hydrogen carbonate aqueons solution (20 ml). The organic layer was dried over anhydrous magnesium sulfate and distilled under reduced pressure to give (2R,3R)-2-(2,4 -difluorophenyl)-3-(4-methanesulfonyloxymethyl-1H-1,2,3 -triazol-1-yl)-1-(1H-1,2,4-triazol-1-yl)-2-butanol as colorless oil.

1H-1,2,4-Triazole (0.19 g) was added to a dispersion of 60% sodium hydride in oil (0.1 g) in N,N-dimethyl formamide (15 ml) under ice-cooling. The mixture was stirred until the generation of hydrogen ceased and a homogenous solution was obtained. To the resulting solution was added a solution of the above methane sulfonate compound in N,N-dimethylformamide (5 ml), followed by heating for 2 hours at 50° C. After cooling, the mixture was diluted with ethyl acetate (50 ml) and then washed with water (25 ml). The organic layer was dried over anhydrous magnesium sulfate and distilled under reduced pressure. The residue was purified by silica gel chromatography (silica gel: 30 g, eluent: ethyl acetate/methanol=4/1) to give Compound 57 (0.08 g) as colorless powder.
mp: 162°–163° C. (recrystallized from diisopropyl ether)
¹H-NMR(CDCl₃) δ: 1.35 (3H,d,J=7Hz), 3.53 (1H,d,J=14Hz), 4.97 (1H,d,J=14Hz), 5.41–5.48 (2H,m), 5.54 (2H, m), 6.77–6.86 (2H,m), 7.41–7.56 (1H,m), 7.73 (1H,s), 7.74 (1H,s), 7.98 (2H,s), 8.25 (1H,s).

Example 44

(2R,3R)-2-(2,4-Difluorophenyl)-3-(4-phenyl-1H-1,2,3-triazol-1-yl)-t-(1H-1,2,4-triazol-1-yl)-2-butanol (Compound 58)

A mixture of toluene (80 ml), phenylacetylene (6.7 ml) and (2R,3R)-3-azido-2-(2,4-difluorophenyl)-1-(1H- 1,2,4-triazol-1-yl)-2-butanol (2 g) was heated for 8 hours at 130° C. After cooling, toluene was distilled off under reduced pressure. The residue was purified by silica gel chromatography (silica gel 50 g, eluent: ethyl acetate) to give Compound 58 (0.85 g) as a colorless powder.
mp: 148°–149° C. (recrystallized from diisopropyl ether)
¹H-NMR(CDCl₃) δ: 1.52 (3H,d,J=7Hz), 3.68 (1H,d,J=14Hz), 4.66 (1H,d,J=14Hz), 5.31 (1H,q,J=7Hz), 5.57 (1H,s), 6.63–6.78 (2H,m), 7.35–7.60 (7H,m), 7.84 (1H,s), 8.00 (1H,s).

Example 45

(2R,3R)-2-(2,4-Difluorophenyl)-1-(1H,1,2,4-triazol-1-yl)- 3-(1H-1,2,3-triazol-1-yl)-2-butanol
(Compound 6)

A mixture of propiolic acid (0.84 ml), mesitylene (20 ml) and (2R,3R)-3-azido-2-(2,4-difluorophenyl)-1-(1H- 1,2,4-triazol-1-yl)-2-butanol (1 g) was heated for 3 hours at 120°

C. After cooling, the mixture was concentrated under reduced pressure. The residue was purified by silica gel chromatography (silica gel 30 g, eluent: ethyl acetate/methanol=10:1) to give the Compound 6 (0.11 g) as a colorless powder.

Example 46

(2R,3R)-2-(2-Fluorophenyl)-3-(2H-tetrazol-2-yl)-1-(1H-1,2,4-triazol-1-yl)-2-butanol (Compound 61) and (2R,3R)-2-(2-fluorophenyl)-3-(1H-tetrazol-1-yl)-1-(1H-1,2,4-triazol-1-yl)-2-butanol (Compound 62)

Using tetrazole (1.2 g) and (2R,3S)-2-(2-fluorophenyl)-3-methyl-2-[(1H-1,2,4-triazol-1-yl)methyl]oxirane (2.0 g), Compound 61 (0.85 g) and Compound 62 (0.59 g) were obtained each as a colorless powder by the same way as in Example 40.

Compound 61 (recrystallized from diisopropyl ether)
mp: 98°–99° C.
$^1$H-NMR (CDCl$_3$) δ: 1.58 (3H,d,J=7Hz), 3.80 (1H,d,J=14Hz), 5.09 (1H,d,J=14Hz), 5.12 (1H,s), 5.72 (1H,q,J=7Hz), 7.00–7.12 (2H,m), 7.24–7.35 (1H,m), 7.48–7.57 (1H,m), 7.69 (1H,s), 7.77 (1H,s), 8.62 (1H,s).
$[α]_D^{20}$ −46.2° (c=0.5, MeOH).

Compound 62 (recrystallized from diisopropyl ether)
mp: 107°–108° C.
$^1$H-NMR (CDCl$_3$) δ: 1.42 (3H,d,J=7Hz), 3.57 (1H,d,J=14Hz), 5.03 (1H,d,J=14Hz), 5.53 (1H,s), 5.64 (1H,q,J=7Hz), 7.02–7.12 (2H,m), 7.24–7.48 (2H,m), 7.74 (1H,s), 7.75 (1H,s), 9.02 (1H,s).
$[α]_D^{20}$: −40.6° (c=0.5, MeOH).

Example 47

(2R,3R)-2-(2,4-Difluorophenyl)-3-(2H-tetrazol-2-yl)-1-(1H-1,2,4-triazol-1-yl)-2-butanol (Compound 4) and (2R,3R)-2-(2,4-difluorophenyl)-3-(1H-tetrazol-1-yl)-1-(1H-1,2,4-triazol-1-yl)-2-butanol (Compound 3)

A mixture of tetrazole (5.6 g), lithium carbonate (29.54 g), dimethylformamide (200 ml) and (2R,3S)-2-(2,4-difluorophenyl)-3-methyl-2-[(1H-1,2,4-triazol-1-yl)methyl]oxirane (10.04 g) was stirred for 29 hours at 110° C. After cooling, to the mixture was added ethyl acetate (200 ml). The mixture was filtered to remove the insoluble substances. The filtrate was distilled off the solvent under reduced pressure. The residue was dissolved in ethyl acetate (300 ml). The solution was washed with saturated saline (100 ml×2). The ethyl acetate layer was dried over anhydrous magnesium sulfate and distilled under reduced pressure. The residue was purified by silica gel chromatography (silica gel 1 kg, eluent: ethyl acetate→ dichloromethane/acetone=3:2).

The first eluate gave an oily substance (4.45 g) of Compound 4. It was crystallized from diisopropyl ether to give a colorless crystalline powder.
mp: 73°–74° C.
$[α]_D^{20}$: −45.9° (c=0.5, methanol).

Then, a second eluate gave Compound 3 (3.73 g). It was crystallized from a mixture of ethyl acetate and n-hexane to give a colorless crystalline powder.
mp: 113°–114° C.

Then, the latter was recrystallized from aqueous ethanol solution to give a colorles crystalline powder having mp. 136°–137° C.

$[α]_{D20}$: −47.5° (c=1, methanol).

Example 48

(2R,3R)-2-(2-Fluorophenyl)-3-(2H-1,2,3-triazol-2-yl)-1-(1H- 1,2,4-triazol-1-yl)-2-butanol (Compound 44) and (2R,3R)-2-(2-fluorophenyl)-3-(1H-1,2,3-triazol-1-yl)-1-(1H- 1,2,4-triazol-1-yl)-2-butanol (Compound 45)

A mixture of (2R,3S)-2-(2-fluorophenyl)-3-methyl-2-[ (1H-1,2,4-triazol-1-yl)methyl]oxirane (20 g), 1H-1,2,3-triazole (8.8 g), potassium carbonate (35.2 g) and dimethylformamide (200 ml) was stirred for 23 hours at 80° C. After cooling, to the mixture was added ethyl acetate (200 ml). The mixture was filtered to remove insoluble substances. The filtrate was distilled under reduced pressure. The residue was dissolved in ethyl acetate (700 ml). The solution was washed with saturated saline (200 ml×2). The ethyl acetate layer was dried over anhydrous magnesium sulfate and distilled under reduced pressure. The residue was purified by silica gel chromatography (silica gel 1 kg, eluent: ethyl acetate→ dichloromethane/acetone=2:1) to give a colorless oily substance of Compound 44 (9.64 g) from the first eluate and Compound 45 (9.75 g) from the second eluate. The latter was recrystallized from mixture of diethyl ether and diisopropyl ether to give colorless crystalline powder.
Compound 45
mp: 119°–120° C.
$[α]_{D20}$: −76.7° (c=1.0, methanol).

Example 49

(2R,3R)-2-(2,4-Difluorophenyl)-3-(2H-1,2,3-triazol-1-yl)- 1-(1H-1,2,4-triazol-1-yl)-2-butanol (Compound 8) and (2R,3R)-2-(2,4-difluorophenyl)-3-(1H-1,2,3-triazol-1-yl)-1-( 1H-1,2,4-triazol-1-yl)-2-butanol (Compound 6)

A mixture of (2R,3S)-2-(2,4-difluorophenyl)-3-methyl-2-[(1H-1,2,4-triazol-1-yl)methyl]oxirane (4 g), 1H-1,2,3-triazole (2.21 g), potassium carbonate (22 g) and dimethylformamide (80 ml) was stirred for 17 hours at 80° C. After cooling, to the mixture was added ethyl acetate (100 ml). The mixture was filtered to remove the insoluble substances. The filtrate was distilled under reduced pressure. The residue was dissolved in ethyl acetate (200 ml). The solution was washed with saturated saline (50 ml× 2). The ethyl acetate layer was dried over anhydrous magnesium sulfate and distilled under reduced pressure. The residue was purified by silica gel chromatography (silica gel 200 g, eluent: ethyl acetate→dichloromethane/acetone= 1:1) to give a colorless crystalline powder of Compound 8 (1.86 g) from the first eluate. Compound 6 (2.4 g) was obtained from the second eluate. The latter was recrystallized from mixture of methylene chloride and diethyl ether to give a colorless crystalline powder.
Compound 8
mp: 93°–95° C. (crystallized from diisopropyl ether)
$[α]_D^{20}$: −70.5° (c=0.5, methanol).
Compound 6
mp: 119°–120° C.
$[a]_D^{20}$: −69.4° (c=1.0, methanol).

Example 50

(2R,3R)-2-(4-Fluorophenyl)-3-(2H-1,2,3-triazol-2-yl)-1-(1H- 1,2,4-triazol-1-yl)-2-butanol (Compound 36) and
(2R,3R)-2-(4-fluorophenyl)-3-(1H-1,2,3-triazol-1-yl)-1-(1H- 1,2,4-triazol-1-yl)-2-butanol (Compound 37)

A mixture of (2R,3S)-2-(4-fluorophenyl)-3-methyl-2-[(1H-1,2,4-triazol-1-yl)methyl]oxirane (10.4 g), 1H-1,2,3-triazole (4.77 g), potassium carbonate (18.5 g) and dimethylformamide (100 ml) was stirred for 18 hours at 80° C. After cooling, to the mixture was added ethyl acetate (80 ml). The mixture was filtered to remove the insoluble substance. The filtrate was distilled under reduced pressure. The residue was dissolved in ethyl acetate (120 ml). The solution was washed with saturated saline (100 ml× 2). The ethyl acetate layer was dried over anhydrous magnesium sulfate and distilled under reduced pressure. The residue was purified by silica gel chromatography (silica gel 150 g, eluent: methylene chloride/acetone=2:1→ 1:1) to give Compound 36 (6.9 g) from the first eluate. Compound 37 (4.8 g) was obtained from the second eluate. The latter was recrystallized from ethyl acetate to give a colorless crystalline powder.

Compound 37
mp: 157°–158° C.
$[\alpha]_D^{20}$: −74.5° (c=1, methanol).

Example 51

(2R,3R)-2-(2,4-Difluorophenyl)-3-(1H-1,2,3-triazol-1-yl)-1-(1H-1,2,4-triazol-1-yl)-2-butanol (Compound 6)

A mixture of (2R,3S)-3-azido-2-(2,4-difluorophenyl)-1-(1H-1,2,4-triazol-1-yl)-2-butanol (3.5 g), toluene (80 ml) and ethyl propiolate (1.66 ml) was heated for 5 hours at 120° C. After cooling, toluene was distilled off under reduced pressure. The residue was purified by silica gel chromatography (silica gel 100 g, eluent: dichloromethane/acetone= 3:1→2:1) to give a mixture of Compound 30 and Compound 31 as a colorless oily substance (4.28 g).

This substance was dissolved in methanol (60 ml), followed by addition of 1N sodium hydroxide aqueons solution (7.2 ml). The mixture was stirred for 20 minutes at room temperature. To the mixture was added 1N hydrochloric acid (7.2 ml) to neutralize. The mixture was distilled under reduced pressure. Water (50 ml) was added to the resulting solution. The mixture was extracted with a mixture of ethyl acetate and tetrahydrofuran (1:1, 50 ml× 3). The extract was dried over anhydrous magnesium sulfate and distilled under reduced pressure to give a mixture (3.3 g) of Compound 32 and Compound 33.

This substance was dissolved in mesitylene (25 ml), followed by heating for 2 hours at 170° C. After cooling, the mixture was distilled under reduced pressure. The residue was purified by silica gel chromatography (silica gel 100 g, eluent: dichloromethane/acetone=5:2) to give Compound 6 (1.65 g) as a colorless crystalline powder.

Example 52

(2R,3R)-2-(2,4-Difluorophenyl)-3-(4-formyl-1H-1,2,3-triazol-1-yl)-1-(1H-1,2,4-triazol-1-yl)-2-butanol (Compound 71)

Dimethylsulfoxide (1.08 ml) was added dropwise at −78° C. to a solution of oxalyl chloride (1 ml) in dichloromethane (30 ml), followed by stirring for 10 minutes. To the mixture was added dropwise over the period of 5 minutes a solution of (2R,3R)-2-(2,4-difluorophenyl)-3-(4 -hydroxymethyl-1H-1,2,3-triazol-1-yl)-1-(1H-1,2,4-triazol-1 -yl)-2-butanol (2 g) in dichloro-methane (30 ml), followed by stirring for 15 minutes at −78° C. and then for 1 hour at −45° C. To the mixture was added triethylamine (5 ml), followed by stirring for 20 minutes at 0° C. To the mixture was added a saturated aqueous ammonium chloride solution (20 ml). The mixture was extracted with dichloromethane (40 ml). The extract was dried over anhydrous magnesium sulfate and distilled under reduced pressure. The residue was purified by silica gel chromatography (silica gel: 200 g, eluent: ethyl acetate/dichloromethane=3:1) to give Compound 71 (1.49 g), which was crystallized from diisopropyl ether to yield a colorless crystalline powder.

mp: 120°–121° C.
$^1$H-NMR(CDCl$_3$) δ: 1.39 (3H,d,J=7Hz), 3.54 (1H,d,J= 14Hz), 5.00 (1H,d,J=14Hz), 5.51 (1H,s), 5.57 (1H,q,J=7Hz), 6.79–6.89 (2H,m), 7.41–7.53 (1H,m), 7.76 (2H,s), 8.53 (1H,s), 10.20 (1H,s).

Example 53

(2R,3R)-2-(2,4-Difluorophenyl)-1-(1H-1,2,4-triazol-1-yl)-3-[(E)-4-(4-trifluoromethylstyryl)-1H-1,2,3-triazol-1-yl]- 2-butanol (Compound 72) and
(2R,3R)-2,(2,4-difluorophenyl)-1-(1H-1,2,4-triazol-1-yl)-3-[(Z)-4-(4-trifluoromethyl styryl)-1H-1,2,3-triazol-1-yl]-2-butanol (Compound 73)

In dimethylsulfoxide (20 ml) was dissolved 4-trifluoro methylbenzyl triphenylphosphonium bromide (1.02 g). To the solution was added 60% sodium hydride in oil (80 mg) under ice-cooling. The mixture was stirred for 15 minutes at room temperature. To the mixture was added (2R,3R)-2-( 2,4-difluorophenyl)-3-(4-formyl-1H-1,2,3-triazol-1-yl)-1-( 1H-1,2,4-triazol-1-yl)-2-butanol (0.52 g), followed by stirring for 30 minutes at room temperature. The mixture was poured into ice-water (50 ml), which was extracted with ethyl acetate (50 ml×3). The extract was washed with water (25 ml×3), dried over magnesium sulfate and concentrated under reduced pressure. The residue was subjected to silica gel chromatography (silica gel: 50 g, eluent: ethyl acetate/hexane=1:1→2:1) to give two isomers (Compound 72 and Compound 73).

Compound 72 (less polar substance, 45 mg, colorless powder)
mp: 143°–144° C. (from diisopropyl ether)
$^1$H-NMR(CDCl$_3$) δ: 1.40 (3H,d,J=7Hz), 3.60 (2H,d,J= 14Hz), 5.02 (1H,d,J=14Hz), 5.44 (1H,s), 5.49 (1H, q, J=7Hz), 6.78–6.87 (2H,m), 7.22 (1H,d,J=16Hz), 7.42 (1H, d,J=16Hz), 7.40–7.70 (5H,m), 7.77 (1H,s), 7.75 (1H,s), 8.05 (1H,s).

Compound 73 (more polar substance, 125 mg, colorless oil)
$^1$H-NMR(CDCl$_3$) δ: 1.23 (3H,d,J=7Hz), 3.49 (1H,d,J= 14Hz), 4.94 (1H,d,J=14Hz), 5.24 (1H,s), 5.37 (1H,q,J=7Hz), 6.75–6.85 (2H,m), 7.38–7.72 (7H,m), 7.46 (1H,s), 7.75 (1H,s), 7.77 (1H,s).

Example 54

(2R,3R)-2-(2,4-Difluorophenyl)-3-[(E)-4-[4-(2,2,3,3-tetra fluoropropoxy)styryl]-1H-1,2,3-triazol-1-yl]-1-(1H-1,2,4 -triazol-1-yl)-2-butanol (Compound 74) and (2R,3R)-2-(2,4 -difluorophenyl)-3-[(Z)-4-[4-(2,2,3,3-tetrafluoropropoxy) styryl]-1H-1,2,3-triazol-1-yl]-1-(1H-1,2,4-triazol-1-yl)-2-butanol (Compound 75)

In dimethylsulfoxide (36 ml) was dissolved 4-(2,2,3,3-tetrafluoropropoxy)benzyl triphenylphosphonium chloride (1.6 g). To the solution was added 60% sodium hydride in oil (144 mg) under ice-cooling. The mixture was stirred for 15 minutes at room temperature. To the mixture was added (2R,3R)-2-(2,4-difluorophenyl)-3-(4-formyl- 1H-1,2,3-triazol-1-yl)-1-(1H-1,2,4-triazol-1-yl)-2-butanol (0.94 g), followed by stirring for 30 minutes at room temperature. The reaction mixture was poured into ice water (100 ml) and extracted with ethyl acetate (100 ml×3). The extract was washed with water (50 ml×3), dried (MgSO$_4$) and concentrated under reduced pressure. The residue was purified by silica gel chromatography (silica gel: 150 g, eluent: ethyl acetate/hexane=2:1) to give two isomers (Compound 74 and Compound 75).

Compound 74 (less polar substance, 98 mg, colorless oil)
$^1$H-NMR(CDCl$_3$) δ: 1.39 (3H,d,J=7Hz), 3.59 (1H,d,J=14Hz), 4.37 (2H,t,J=12Hz), 5.00 (1H,d,J=14Hz), 5.43 (1H, s), 5.48 (1H,q,J=7Hz), 6.08 (1H,tt, J=52Hz, 40Hz), 6.67–7.08 (5H,m), 6.99 (1H,d,J=16Hz), 7.29–7.55 (2H,m), 7.33 (1H,d,J=16Hz), 7.74 (1H,s), 7.78 (1H,s), 7.99 (1H,s).

Compound 75 (more polar substance, 320 mg, colorless oil)
$^1$H-NMR (CDCl$_3$) δ: 1.25 (3H, d, J=7Hz), 3.52 (1H, d, J=14Hz), 4.40 (2H,t,J=12Hz), 4.53 (1H,d,J=14Hz), 5.22 (1H,s), 5.39 (1H,q,J=7Hz), 6.11 (1H,tt, J=52Hz, 40Hz), 6.69–6.96 (6H,m), 7.36–7.48 (3H,m), 7.56 (1H,s), 7.76 (2H,s).

Example 55

(2R,3R)-2-Acetoxy-(2,4-fluorophenyl)-3-(1H-1,2,3-triazol-1 -yl)-1-(1H-1,2,4-triazol-1-yl)butane (Compound 76)

A mixture of (2R,3R)-2-(2,4-difluorophenyl)-3-(1H- 1,2,3-triazol-1-yl)-1-(1H-1,2,4-triazol-1-yl)-2-butanol (Compound 6, 0.64 g), acetic anhydride (1.42 ml), pyridine (3 ml) and dimethylaminopyridine (0,243 mg) was stirred for 17 hours at 80° C. After cooling, to the mixture was added water (80 ml). The mixture was extracted with ethyl acetate (80 ml×2). The extract was washed with water (40 ml×2), dried over anhydrous sodium sulfate and distilled under reduced pressure. The residue was purified by silica gel chromatography (silica gel 100 g, eluent: methylene chloride/acetone=3:1→2:1) to give Compound 76 (0,302 g) as a colorless crystalline powder which was recrystallized from diethyl ether.

mp: 134°–135° C.

$^1$H-NMR(CDCl$_3$)δ: 1.81 (3H,dd,J=2Hz,7Hz), 2.03 (3H, s), 5.38 (1H,dd,J=3Hz,15Hz), 5.51 (1H,d,J=15Hz), 5.65 (1H,q,J=7Hz), 6.34–6.46 (1H,m), 6.70–6.94 (2H,m), 7.25 (1H,s), 7.60 (1H,s), 7.98 (2H,s).

Example 56

(2R,3R)-2-Acetoxy-2-(2,4-fluorophenyl)-3-(1H-tetrazol-1 -yl)-1-(1H-1,2,4-triazol-1-yl)butane (Compound 77)

Using (2R,3R)-2-(2,4-difluorophenyl)-3-(1H-tetrazol-1-yl)-1-(1H-1,2,4-triazol-1-yl)-2-butanol (Compound 3), substantially the same reaction as in the Example 55 was conducted to give Compound 77.

mp: 202°–203° C. (recrystallized from diethyl ether )

$^1$H-NMR(CDCl$_3$) δ: 1.88 (3H,d,J=7Hz), 1.99 (3H,s), 5.32 (1H,dd,J=3Hz,15Hz), 5.55 (1H,d,J=15Hz), 5.71 (1H,q,J=7Hz), 6.29–6.43 (1H,m), 6.76–6.95 (2H,m), 8.01 (1H,s), 8.05 (1H,s), 8.40 (1H,s).

Example 57

(2R,3R)-2-Acetoxy-2-(2-fluorophenyl)-3-(1H-1,2,3-triazol-1 -yl)-1-(1H-1,2,4-triazol-1-yl)butane (Compound 78)

Using (2R,3R)-2-(2-fluorophenyl)-3-(1H-1,2,3-triazol-1-yl)-1-(1H-1,2,4-triazol-1-yl)-2-butanol (Compound 45), substantially the same reaction as in the Example 55 was conducted to give Compound 78.

mp: 133°–134° C. (recrystallized from diethyl ether)

$^1$H-NMR(CDCl$_3$)δ: 1.79 (3H,dd,J=2Hz,7Hz), 2.04 (3H, s), 5.42 (1H,dd,J=3Hz,15Hz), 5.54 (1H,d,J=15Hz), 5.68 (1H,q,J=7Hz), 6.42–6.50 (1H,m), 6.97–7.42 (3H,m), 7.18 (1H,s), 7.57 (1H,s), 7.97 (2H,s).

Example 58

(2R,3R)-2-Acetoxy-2-(4-fluorophenyl)-3-(1H-1,2,3-triazol-1 -yl)-1-(1H-1,2,4-triazol-1-yl)butane (Compound 79)

Using (2R,3R)-2-(4-fluorophenyl)-3-(1H-1,2,3-triazol-1-yl)-1-(1H-1,2,4-triazol-1-yl)-2-butanol (Compound 37), substantially the same reaction as in the Example 55 was conducted to give Compound 79.

$^1$H-NMR(CDCl$_3$) δ: 1.74 (3H,d,J=7Hz), 2.08 (3H,s), 5.28 (1H,d,J=15Hz), 5.47 (1H,d,J=15Hz), 5.56 (1H, q, J=7Hz), 6.75–6.82 (2H,m), 6.99–7.09 (2H,m), 7.06 (1H,s), 7.58 (1H,s), 7.98 (2H,s).

Example 59

(2R,3R)-2-Acetoxy-2-(4-chlorophenyl)-3-(1H-1,2,3-triazol-1 -yl)-1-(1H-1,2,4-triazol-1-yl)butane (Compound 80)

Using (2R,3R)-2-(4-chlorophenyl)-3-(1H-1,2,3-triazol-1-yl)-1-(1H-1,2,4-triazol-1-yl)-2-butanol (Compound 35), substantially the same reaction as in the Example 55 was conducted to give Compound 80.

$^1$H-NMR(CDCl$_3$)δ: 1.74 (3H,d,J=7Hz), 2.07 (3H,s), 5.26 (1H,d,J=15Hz), 5.46 (1H,d,J=15Hz), 5.54 (1H,q,J=7Hz), 6.74 (2H,d,J=8.8Hz), 7.12 (1H,s), 7.30 (2H,d,J=8.8Hz), 7.59 (1H,s), 7.99 (2H,s).

Preparation 1

Compound 6 obtained in Example 6 and the components (2), (3) and (4) in the following ratio were mixed and packed in gelatin capsule so as to contain Compound 6 in an amount of 50 mg for each capsule.

| | |
|---|---|
| (1) Compound 6 (obtained in Example 6) | 50 mg |
| (2) lactose | 100 mg |
| (3) cornstarch | 40 mg |
| (4) magnesium stearate | 10 mg |
| total | 200 mg |

Preparation 2

Compound 37 obtained in Example 30, and magnesium stearate were granulated into soluble starch solution, dried and then mixed with lactose and cornstarch. The mixture was subjected to compression molding to obtain a tablet containing the ratio stated below.

| | |
|---|---|
| (1) Compound 37 (obtained in Example 30) | 50 mg |
| (2) lactose | 65 mg |
| (3) cornstarch | 30 mg |
| (4) soluble starch | 35 mg |
| (5) magnesium stearate | 20 mg |
| total | 200 mg |

Preparation 3

Using Compound 3 obtained in Example 3, 0.1% solution of Compound 3 in physiological saline was prepared, sterilized and filtered. Every 50 ml of the solution was poured into a vial to obtain an intravenous injection solution containing 50 mg of the Compound 3.

The compounds of the present invention are shown in Tables 7, 8, 9, 10, 11, 12, 13, 14 and 15. It should be understood, however, that the invention is not limited to the compounds.

TABLE 7

[Structure: Q-N(imidazolyl/triazolyl ring)–CH$_2$–C(OH)(R)(phenyl with R$^1$ at position 2, R$^2$ at position 4)–CH(CH$_3$)(R)–N(A ring)]

| Compd. No. | R$^1$, R$^2$ | Q-N ring | -N A ring |
|---|---|---|---|
| 1 | 2-F, 4-F | imidazol-1-yl | pyrazol-1-yl |
| 2 | 2-F, 4-F | 1,2,4-triazol-1-yl | pyrazol-1-yl |
| 3 | 2-F, 4-F | imidazol-1-yl | 1,2,3-triazol-2-yl |
| 4 | 2-F, 4-F | imidazol-1-yl | 1,2,3-triazol-1-yl |
| 5 | 2-F, 4-F | imidazol-1-yl | 1,2,4-triazol-1-yl |
| 6 | 2-F, 4-F | 1,2,4-triazol-1-yl | 1,2,4-triazol-1-yl |
| 7 | 2-F, 4-F | imidazol-1-yl | 1,2,3-triazol-1-yl |
| 8 | 2-F, 4-F | imidazol-1-yl | pyrazol-1-yl |
| 9 | 2-F, 4-F | imidazol-1-yl | pyrazol-1-yl |
| 10 | 2-F, 4-F | imidazol-1-yl | tetrazol-2-yl |
| 11 | 2-F, 4-N(1,2,4-triazol-1-yl) | imidazol-1-yl | 1,2,4-triazol-1-yl |
| 12 | 2-F, 4-N(1,2,4-triazol-1-yl) | imidazol-1-yl | 1,2,4-triazol-1-yl |

TABLE 8

| Compd. No. | R¹, R² | (Q/N ring) | -N⟨A⟩ |
|---|---|---|---|
| 13 | 2-F, 4-N(pyrazol-1-yl) | 1,2,4-triazol-1-yl | 1,2,4-triazol-1-yl |
| 14 | 2-N(pyrazol-1-yl), 4-N(pyrazol-1-yl) | 1,2,4-triazol-1-yl | 1,2,4-triazol-1-yl |
| 15 | 2-F, 4-N(benzotriazol-1-yl) | 1,2,4-triazol-1-yl | 1,2,4-triazol-1-yl |
| 16 | 2-F, 4-N(3,5-dimethylpyrazol-1-yl) | 1,2,4-triazol-1-yl | 1,2,4-triazol-1-yl |
| 17 | 2-N(3,5-dimethylpyrazol-1-yl), 4-F | 1,2,4-triazol-1-yl | 1,2,4-triazol-1-yl |
| 18 | 2-N(3,5-dimethylpyrazol-1-yl), 4-N(3,5-dimethylpyrazol-1-yl) | 1,2,4-triazol-1-yl | 1,2,4-triazol-1-yl |
| 19 | 2-F, 4-N(2-methylimidazol-1-yl) | 1,2,4-triazol-1-yl | 1,2,4-triazol-1-yl |
| 20 | 2-F, 4-F | 1,2,4-triazol-1-yl | pyrazol-1-yl |
| 21 | 2-F, 4-F | 1,2,4-triazol-1-yl | purin-9-yl (imidazo[4,5-d]pyrimidin-yl) |
| 22 | 2-F, 4-F | imidazol-1-yl | imidazo[4,5-b]pyridin-yl |

TABLE 8-continued

| Compd. No. | R¹, R² | (Q/N ring) | —N A |
|---|---|---|---|
| 23 | 2-F, 4-F | triazole | imidazo-pyridine |

TABLE 9

| Compd. No. | R¹, R² | (Q/N ring) | —N A |
|---|---|---|---|
| 24 | 2-F, 4-F | imidazole | imidazo-pyridine |
| 26 | 2-F, 4-F | triazole | imidazo-pyridine |
| 29 | 2-F, 4-F | imidazole | imidazo-pyridine |
| 30 | 2-F, 4-F | triazole | triazole-COOC₂H₅ |
| 31 | 2-F, 4-F | triazole | triazole-COOC₂H₅ |
| 32 | 2-F, 4-F | triazole | triazole-COOH |
| 33 | 2-F, 4-F | triazole | triazole-COOH |

TABLE 10

| Compd. No. | R¹, R² | (Q/N ring) | —N A |
|---|---|---|---|
| 34 | 4-Cl | triazole | pyrazole |
| 35 | 4-Cl | triazole | triazole |
| 36 | 4-F | triazole | tetrazole |
| 37 | 4-F | triazole | triazole |
| 38 | 4-CF₃ | triazole | pyrazole |
| 39 | 4-CF₃ | triazole | triazole |
| 40 | 4-OCF₃ | triazole | pyrazole |
| 41 | 4-OCF₃ | imidazole | triazole |
| 42 | 2-Cl | imidazole | pyrazole |

TABLE 10-continued

| Compd. No. | R¹, R² | (triazole-Q group) | —N⟨A⟩ |
|---|---|---|---|
| 43 | 2-Cl | triazole | triazole (N-linked) |

TABLE 11

| Compd. No. | R¹, R² | (triazole-Q group) | —N⟨A⟩ |
|---|---|---|---|
| 44 | 2-F | triazole | pyrazole |
| 45 | 2-F | triazole | 1,2,3-triazole |
| 46 | 2-F, 4-F | triazole | imidazo-pyrazine with H₃CO |
| 47 | 2-F, 4-F | triazole | imidazo-pyrazine with OCH₃ |
| 48 | 2-F, 4-F | triazole | imidazo-pyrazine with CH₃ |
| 49 | 2-F, 4-F | triazole | imidazo-pyrazine with triazolyl |
| 50 | 2-F, 4-F | triazole | imidazo-pyrazine with bis-triazolyl |

TABLE 11-continued

| Compd. No. | R¹, R² | (triazole-Q group) | —N⟨A⟩ |
|---|---|---|---|
| 51 | 4-Cl | triazole | tetrazole |
| 52 | 4-Cl | triazole | tetrazole (isomer) |
| 53 | 4-F | triazole | tetrazole |

TABLE 12

| Compd. No. | R¹, R² | (triazole-Q group) | —N⟨A⟩ |
|---|---|---|---|
| 54 | 4-F | triazole | tetrazole |
| 55 | 2-F, 4-F | triazole | triazole-CH₂OH |
| 56 | 2-F, 4-F | triazole | triazole-CH₂OH |
| 57 | 2-F, 4-F | triazole | triazole-CH₂-N(triazole) |
| 58 | 2-F, 4-F | triazole | triazole-phenyl |
| 59 | 2-Cl, 4-Cl | triazole | triazole |
| 60 | 2-Cl, 4-Cl | triazole | triazole |

TABLE 12-continued

| Compd. No. | R¹, R² | ⟨Q/N-N⟩ | -N⟨A⟩ |
|---|---|---|---|
| 61 | 2-F | triazole | tetrazole (1,2,3,4-N) |
| 62 | 2-F | triazole | tetrazole (1,2,3,4-N isomer) |
| 63 | 2-Cl, 4-Cl | triazole | tetrazole |

TABLE 13

| Compd. No. | R¹, R² | ⟨Q/N-N⟩ | -N⟨A⟩ |
|---|---|---|---|
| 64 | 2-Cl, 4-Cl | triazole | tetrazole (1,2,3,4-N) |
| 65 | 2-Cl | triazole | tetrazole |
| 66 | 2-Cl | triazole | tetrazole |
| 67 | 4-CF₃ | triazole | tetrazole |
| 68 | 4-CF₃ | triazole | tetrazole |
| 69 | 4-OCF₃ | triazole | tetrazole |
| 70 | 4-OCF₃ | triazole | tetrazole |

TABLE 14

| Compd. No. | R¹, R² | ⟨Q/N-N⟩ | -N⟨A⟩ |
|---|---|---|---|
| 71 | 2-F, 4-F | triazole | -N-triazole-CHO |
| 72 | 2-F, 4-F | triazole | -N-triazole-CH=CH-C₆H₄-CF₃ (trans) |
| 73 | 2-F, 4-F | triazole | -N-triazole-CH=CH-C₆H₄-CF₃ (cis) |

TABLE 14-continued

| Compd. No. | R¹, R² | (Q/N-N group) | -N A |
|---|---|---|---|
| 74 | 2-F, 4-F | imidazole-N | triazole-CH=CH-C₆H₄-OCH₂CF₂CF₂H (trans) |
| 75 | 2-F, 4-F | imidazole-N | triazole-CH=CH-C₆H₄-OCH₂CF₂CF₂H (cis) |

TABLE 15

Structure: H₃CC(O)O-C(CH₂-N(triazole))(phenyl-R¹,R²)-CH(CH₃)-N A, (R),(R) configuration

| Compd. No. | R¹, R² | -N A |
|---|---|---|
| 76 | 2-F, 4-F | 1,2,3-triazole |
| 77 | 2-F, 4-F | tetrazole |
| 78 | 2-F | 1,2,3-triazole |
| 79 | 4-F | 1,2,3-triazole |
| 80 | 4-Cl | 1,2,4-triazole |

ACTIVITY

Experiment 1

The antifungal activity of the Compound (I) was evaluated by the following method: A paper disk (manufactured by TOYO SEISAKUSHO, 8 mm in diameter) dipped into methanol solution containing Compound (I) in an amount of 1000 µg/ml was placed on an agar plate containing various fungi. After the cultivation of said fungi at 28° C. for 2 days, measurement was made as to the diameter of the growth inhibition zone produced around the paper disk.

The media used for the evaluation are as follows:

A: yeast-nitrogen-base agar medium (pH 7.0)

B: peptone-yeast extract-glucose agar medium (pH 7.0)

The antifungal spectra of Compound (I) are shown in Table 16.

TABLE 16

| Test microorganism | | Diameter of growth inhibition zone (mm) | | |
|---|---|---|---|---|
| | | cpd. 2 | cpd. 2 | cpd. 13 |
| Candida albicans IFO 0583 | A | 40 | 45 | 35 |
| Candida utilis IFO 0619 | A | 15 | 45 | 13 |
| Aspergillus niger IFO 4066 | A | 37 | 18 | + |
| Aspergillus fumigatus IFO 6344 | A | 44 | 20 | 0 |
| Cryptococcus neoformans IFO 0410 | A | 20 | 28 | 19 |
| Trichophyton rubrum IFO 6467 | B | 50 | 50 | 35 |
| Trichophyton mentagrophytes IFO 7522 | B | 50 | 38 | 0 |
| Microsporum gypseum IFO 6075 | B | 50 | 43 | 0 |

Table 17 shows the antifungal activities of the compounds (I) against *Candida albicans*.

TABLE 17

| Cpd. No. | Diameter of growth-inhibition zone (mm) Candida albicans IFO 0583 (Medium A, 28° C., two-day culture) |
|---|---|
| 3 | 38 |
| 4 | 40 |
| 5 | 30 |
| 6 | 50 |
| 7 | 28 |
| 8 | 55 |
| 9 | 45 |
| 10 | 25 |
| 11 | 25 |
| 12 | 23 |
| 14 | 25 |
| 15 | 28 |
| 16 | 33 |
| 17 | 20 |
| 18 | 20 |
| 20 | 20 |
| 21 | 38 |
| 22 | 15 |
| 23 | 42 |
| 24 | 33 |
| 26 | 25 |
| 34 | 37 |
| 35 | 35 |
| 36 | 38 |
| 37 | 35 |
| 38 | 43 |
| 39 | 40 |
| 40 | 43 |
| 41 | 42 |
| 42 | 43 |
| 43 | 45 |
| 44 | 48 |
| 45 | 47 |
| 46 | 33 |
| 47 | 25 |
| 48 | 25 |
| 49 | 33 |
| 50 | 18 |
| 51 | 24 |
| 52 | 12 |
| 54 | 30 |
| 55 | 17 |
| 57 | 20 |
| 58 | 26 |
| 61 | 36 |
| 62 | 20 |
| 71 | 38 |
| 72 | 24 |
| 73 | 29 |
| 74 | 20 |
| 75 | 24 |
| 76 | 15 |
| 78 | 26 |

Experiment 2

Method: 5-Week-old Crj:CDF$_1$ mice were inoculated with the minimum lethal dose of *Candida albicans* into the vein. A test compound was administered orally once immediately after infection. The activity was shown in terms of ED$_{50}$ values calculated by the Reed and Muench method from the survival rate on day 7 after infection.

The protective effect of Compound (I) evaluated in the experimental infection in mice is shown in Table 18.

TABLE 18

| Cpd. No. | ED$_{50}$ (mg/kg; p.o.) |
|---|---|
| 1 | 8.0 |
| 3 | 0.35 |
| 4 | 0.18 |
| 5 | 8.0 |
| 6 | 0.28 |
| 8 | 0.39 |
| 9 | 8.0 |
| 12 | 8.0 |
| 13 | 11.3 |
| 21 | 8.0 |
| 34 | 2.0 |
| 35 | 0.18 |
| 36 | 2.0 |
| 37 | 0.45 |
| 38 | 0.71 |
| 39 | 0.18 |
| 41 | 0.32 |
| 42 | 0.71 |
| 43 | 0.39 |
| 44 | 1.41 |
| 45 | 0.35 |
| 46 | 8.0 |
| 47 | 11.3 |
| 49 | 2.0 |
| 50 | 8.0 |
| 51 | 0.35 |
| 52 | 0.77 |
| 53 | 1.5 |
| 54 | 2.0 |
| 61 | 0.32 |
| 62 | 0.35 |
| 72 | 0.65 |
| 74 | 2.0 | p.o.: Oral administration

As can be seen from the above results, Compound (I) of the present invention and a salt thereof have excellent antifungal activities, also less toxicity and side-effects. The compounds are useful for the treatment of fungal infections in humans and other animals.

What we claim is:

1. A compound of the formula (I):

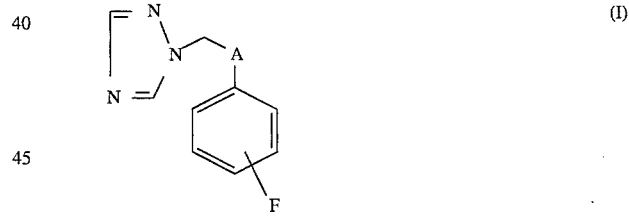

wherein A is a moiety selected from

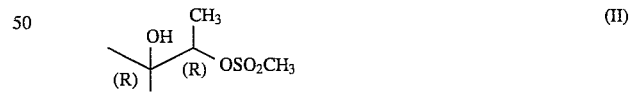

OR

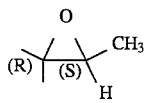

wherein (R) shows that the carbon atom has R-configuration; and (S) shows that the carbon atom has S-configuration, or a physiological acceptable salt thereof.

2. The compound of claim 1 which is (2R,3S)-2-(2-fluorophenyl)-3-methyl-2-(1H-1,2,4-triazol-1-yl-methyl)oxirane, or its salt.

3. The compound of claim 1 which is (2R,3S)-2-(4-fluorophenyl)-3-methyl-2-(1H-1,2,4-triazol-1-methyl)-oxirane, or its physiologically acceptable salt.

4. A process for preparing a compound of the formula (I'):

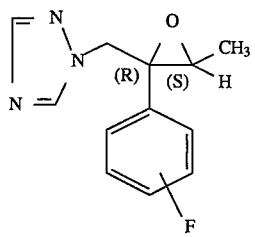

or its physiologically acceptable salt, wherein (R) and (S) refer to a carbon having R-configuration and S-configuration respectively, which comprises (A) reacting a compound of the formula (IV):

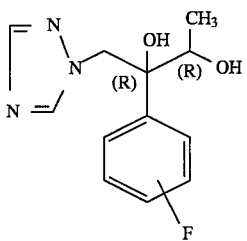

or its physiologically acceptable salt, wherein (R) is as defined above, with methanesulfonyl chloride in the presence of triethyl-amine to give a compound of the formula (I"):

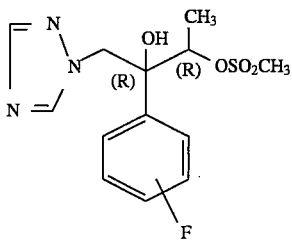

or its physiologically acceptable salt, wherein (R) is as defined above, (B) then reacting a compound of the formula (I") obtained as above with sodium methylate to give a compound of the formula (I'), or its physiologically acceptable salt.

* * * * *